(12) United States Patent
Martin et al.

(10) Patent No.: US 7,196,085 B2
(45) Date of Patent: Mar. 27, 2007

(54) PHTHALAZINONE DERIVATIVES

(75) Inventors: Niall Morrison Barr Martin, Cambridge (GB); Graeme Cameron Murray Smith, Cambridge (GB); Penny Jane Eversley, Launceston (GB); Xiao-Ling Cockcroft, Horsham (GB); Frank Kerrigan, Tintagel (GB); Janet Hoare, Tintagel (GB); Lesley Dixon, Tintagel (GB)

(73) Assignees: KuDOS Pharmaceuticals Limited, Cambridge (GB); Maybridge plc, Cornwall (GB)

( * ) Notice: Subject to any disclaimer, the term of this patent is extended or adjusted under 35 U.S.C. 154(b) by 11 days.

(21) Appl. No.: 10/426,147

(22) Filed: Apr. 29, 2003

(65) Prior Publication Data
US 2004/0023968 A1 Feb. 5, 2004

Related U.S. Application Data

(60) Provisional application No. 60/376,497, filed on Apr. 30, 2002.

(51) Int. Cl.
| | |
|---|---|
| *A01N 43/60* | (2006.01) |
| *A01N 43/58* | (2006.01) |
| *A61K 31/50* | (2006.01) |
| *A61K 31/495* | (2006.01) |
| *C07D 487/00* | (2006.01) |

(52) U.S. Cl. .................. 514/248; 544/236; 544/237
(58) Field of Classification Search ................ 514/248, 514/236, 237
See application file for complete search history.

(56) References Cited

U.S. PATENT DOCUMENTS

| | | | |
|---|---|---|---|
| 3,813,384 | A | 5/1974 | Vogelsang et al. |
| 4,665,181 | A | 5/1987 | Thomas et al. |
| 4,841,047 | A | 6/1989 | Engel et al. |
| 5,032,617 | A | 7/1991 | Lee et al. |
| 5,041,653 | A | 8/1991 | Lee et al. |
| 5,215,738 | A | 6/1993 | Lee et al. |
| 5,556,856 | A | 9/1996 | Engel et al. |
| 5,587,384 | A | 12/1996 | Zhang et al. |
| 5,648,355 | A | 7/1997 | Theoharides |
| 5,874,444 | A | 2/1999 | West |
| 5,886,178 | A | 3/1999 | Allen et al. |
| 6,197,785 | B1 | 3/2001 | Jackson et al. |
| 6,340,684 | B1 | 1/2002 | Napoletano et al. |
| 6,426,415 | B1 | 7/2002 | Jackson et al. |
| 6,476,048 | B1 | 11/2002 | Szabo et al. |
| 6,498,160 | B2 | 12/2002 | Napoletano et al. |
| 6,514,983 | B1 | 2/2003 | Li |
| 6,514,984 | B1 | 2/2003 | Watanabe |
| 6,635,642 | B1 | 10/2003 | Jackson et al. |
| 6,677,333 | B1* | 1/2004 | Seko et al. ............ 514/218 |
| 2002/0183325 | A1 | 12/2002 | Martin et al. |
| 2005/0059663 | A1 | 3/2005 | Martin et al. |
| 2005/0080096 | A1 | 4/2005 | Ishida et al. |
| 2005/0227919 | A1 | 10/2005 | Kudos |

FOREIGN PATENT DOCUMENTS

| | | |
|---|---|---|
| DE | 2143745 | 3/1973 |
| DE | 3813531 | 4/1988 |
| DE | 287 032 | 2/1991 |
| EP | 0030861 | 6/1981 |
| EP | 0269968 | 6/1988 |
| EP | 0 355 570 | 2/1990 |
| EP | 0389995 | 10/1990 |
| EP | 0502575 | 9/1992 |
| EP | 0 590 551 | 6/1994 |

(Continued)

OTHER PUBLICATIONS

Hawley's Condensed Chemical Dictionary, 13th ed. pp. 716 and 825 © 1997 by Van Nostrand Reinhold.*
Virag and Szabo, "The Therapeutic Potential of Poly(ADP-Ribose) Polymerase Inhibitors" Pharmacological Reviews, vol. 54(3) pp. 375-429 (2002).*

(Continued)

*Primary Examiner*—Zachary C. Tucker
(74) *Attorney, Agent, or Firm*—Michael Best & Friedrich LLP

(57) ABSTRACT

A compound of formula:

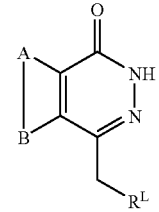

or an isomer, salt, solvate, chemically protected form, or prodrug thereof, wherein A and B together represent an optionally substituted, fused aromatic ring; $R^L$ is a $C_{5-7}$ aryl group substituted in the meta position by the group $R^2$, and optionally further substituted; wherein $R^2$ is selected from:

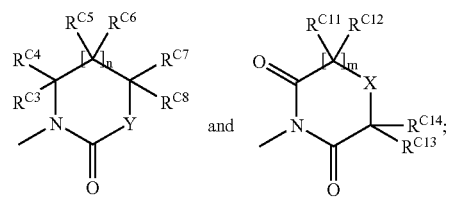

and its use as a pharmaceutical, in particular for the treatment of diseases ameliorated by inhibiting the activity of PARP.

29 Claims, No Drawings

FOREIGN PATENT DOCUMENTS

| | | |
|---|---|---|
| EP | 0634404 A1 | 1/1995 |
| EP | 699754 | 3/1996 |
| EP | 705903 | 4/1996 |
| EP | 0 792 643 | 9/1997 |
| FR | 2 262 513 * | 9/1975 |
| GB | 721286 | 1/1955 |
| GB | 2384776 | 3/2004 |
| IT | MI98A001671 | 4/1999 |
| JP | 54156526 | 12/1979 |
| JP | 58164577 | 9/1983 |
| JP | 62252774 | 11/1987 |
| WO | WO 91/18591 | 12/1991 |
| WO | WO 93/14086 | 7/1993 |
| WO | WO 94/10151 | 5/1994 |
| WO | WO 95/24379 | 9/1995 |
| WO | WO 96/19225 | 6/1996 |
| WO | WO 98/43477 | 10/1998 |
| WO | WO 98/51308 | 11/1998 |
| WO | WO 99/08680 | 2/1999 |
| WO | WO 99/11624 | 3/1999 |
| WO | WO 99/11645 | 3/1999 |
| WO | WO 99/11649 | 3/1999 |
| WO | WO 99/44612 | 9/1999 |
| WO | WO 99/47494 | 9/1999 |
| WO | WO 00/05219 | 2/2000 |
| WO | WO 00/42040 | 7/2000 |
| WO | WO 00/44726 | 8/2000 |
| WO | WO 00/67734 | 11/2000 |
| WO | WO 01/12199 | 2/2001 |
| WO | WO 01/16136 | 3/2001 |
| WO | WO 01/16137 | 3/2001 |
| WO | WO 01/21615 | 3/2001 |
| WO | WO 01/23390 | 4/2001 |
| WO | WO 01/57038 | 8/2001 |
| WO | WO 01/79184 | 10/2001 |
| WO | WO 01/85686 | 11/2001 |
| WO | WO 01/85687 | 11/2001 |
| WO | WO 01/87845 | 11/2001 |
| WO | WO 01/90077 | 11/2001 |
| WO | WO 02/36576 | 5/2002 |
| WO | WO 03/070726 | 5/2002 |
| WO | WO 02/44157 | 6/2002 |
| WO | WO 02/068407 | 9/2002 |
| WO | WO 02/090334 | 11/2002 |
| WO | WO 02/094790 | 11/2002 |
| WO | WO 03/007959 | 1/2003 |
| WO | WO 03/051879 | 6/2003 |
| WO | WO 03/055865 | 7/2003 |
| WO | WO 03/057145 | 7/2003 |
| WO | WO 03/063874 | 8/2003 |
| WO | WO 03/070707 | 8/2003 |
| WO | WO 03/080581 | 10/2003 |
| WO | WO 03/093261 | 11/2003 |
| WO | WO 2004/080976 | 9/2004 |
| WO | WO 2005/053662 | 6/2005 |

OTHER PUBLICATIONS

Bowman et al, "Differential effects of the poly (ADP-ribose) polymerase (PARP) inhibitor NU1025 on topoisomerase I and II inhibitor cytotoxicity in L1210 cells in vitro" British Journal of Cancer, vol. 84(1), pp. 106-112 (2001).*

Griffin et al, "The role of inhibitors of poly (ADP-ribose) polymerase as resistance-modifying agents in cancer therapy" Biochim vol. 77, pp. 408-422 (1995).*

Richard B. Silverman, The Organic Chemistry of Drug Design and Drug Action, pp. 352-400. © 1992 Academic Press, Inc.*

Hans Bundgaard, Design of Prodrugs, p. 1. © 1985 Elsevier Science Publishers.*

Al-Dabbagh and Smith, "Species differences in oxidative drug metabolism: some basic considerations." Archives of toxicology. Supplement. Archiv fur Toxikologie. supplement, vol. 7, pp. 219-231 (1984).*

West, Anthony R. "Solid State Chemistry and its Applications" Wiley, New York, pp. 358 and 365 (1988).*

Gaken et al, "Efficient Retroviral Infection of Mamallian Cells Is Blocked by Inhibition of Poly(ADP-Ribose) Polymerase Activity" Journal of Virology, vol. 70(6), pp. 3992-4000 (1996).*

Banasik, Marek, et al., "Specific Inhibitors of Poly (ADP-Ribose) Synthetase and Mono(ADP-Ribosyl) transferase," J. Biol. Chem., 1569-1575 (1992).

Ben-Hur, E., et al.., British J. Cancer, 49 (Suppl. VI), 39-42 (1984).

Berge, Stephen M., et al., "Pharmaceutical Salts," J. Pharma. Sci., 66:1, 1-19 (Jan. 1977).

Berger, Nathan A., "Poly(ADP-ribose) in the cellular response to DNA damage," Radiation Research., 101, 4-14 (1985).

Bold, Guido, et al., "New anilinophtalazines as potent and orally well absorbed inhibitors of the FEBF receptor tyrosine kinases useful as antagonists of tumor-driven angiogenesis," J. Med. Chem., 43:12, 2310-2323 (2000).

Burzio, Luis, et al., "Poly (adnenosine diphosphoribose) synthase activity of isolated nuclei of normal and leukemic leukocytes (38930)," Proceed. Soc. Exp. Biol. Med., 149, 933-938 (1975).

Cantoni, Orazio, et al., "Hydrogen peroxide insult in cultured mammalian cells: relationships between DNA single-strand breakage, poly (ADP-ribose) metabolism and cell killing," Biochimica et Biophysica Acta., 1014, 1-7 (1989).

Cosi, C., "Poly (ADP-ribose) polymerase: early involvement in glutamate-induced neurotoxicity in cultured cerebellar granule cells," J. Neurosci. Research, 39, 38-46 (1994).

D'Adda Di Fagagna, Fabrizio, et al., "Functions of poly (ADP-ribose) polymerase in controlling telomere length and chromosomal stability," Nature Genetics, 23(1), 76-80 (Sep. 1999).

D'Amours, Damien, et al., "Poly (ADP-ribosyl)ation reactions in the regulation of nuclear functions," Biochem. J., 342, 249-268 (1999).

Durkacz, Barbara W., et al., "(ADP-ribose)$_n$ participates in DNA excision repair," Nature, 283:7.

El-Tamaty, El-Sayed H., et al., "Synthesis and biological activity of some 4-benzyl-192H)-phthalazinone derivatives," Indian J. of Chem. (and abstract), 35B, 1067-1072 (Oct. 1996).

Fuska, J., et al., "New Cytotoxic and antitumor agents," Chemical Abstracts, 104:102050 (1986).

Gäken, Joop A., et al., "Efficient retroviral infection of mammalian cells is blocked by inhibition of poly (ADP-ribose) polymerase activity," J. Virology, 70:6, 3992-4000 (Jun. 1986).

Hall, Iris H., et al., "Cytotoxicity of imides-N-alkyl semicarbazones, thiosemiicarbazones, acetylhydrazones and related derivatives," Anti-Cancer Drugs (and abstract 122:204573), V.6, 147-153 (1995).

Hirai, Kiyoshi, et al., "Aberration of poly (adenosine diphosphate-ribose) metabolism in human colon adenomatous polyps and cancers," Cancer Research 43, 3441-3446 (Jul. 1983).

Kawamura, Ikuo, et al., "Ponalrestat, an aldose reductase inhibitor," Chemical Abstract 132:273943.

Liaudet, Lucas, et al., "Protection against hemorrhagic shock in mice genetically deficient in poly (ADP-ribose) polymerase," Proc. Natl. Acad. Sci., 97:18, 10203-10208 (Aug. 29, 2000).

Martin, Niall, et al., "Phthalazinone derivatives as potent PARP-1 inhibitors," Abstract 107, ADPR 2001 13th Int'l Symposium on ADP-ribosylation, (Jun. 8-11, 2001).

Ménissier De Murcia, Josiane, et al, "Requirement of poly (ADP-ribose) polymerase in recovery from DNA damage in mice and in cells," Proc. Natl. Acad. Sci. USA, 94, 7303-7307 (Jul. 1997).

Miwa, Masanao, et al., "Cell densiity-dependent increase in chromatin-associated ADP-ribosyltransferase activity in simian virus 40-transformed cells," Arch. Biochem. Biophys., 181, 313-321 (1977).

Perkins, Ed, et al., "Novel inhibitors of poly (ADP-ribose) polymerase/PARP1 and PARP2 identified using a cell-based screen in yeast," Cancer Research, 61, 4175-4183 (May 15, 2001).

Rattan, Suresh I., and Clark, Brian F., "Kinetin delays the onset of ageing characteristics in human fibroblasts," *Biochem. Biophys. Research Comm.*, 201:2, 665-672 (Jun. 15, 1994).

(Le) Rhun, Yves, et al., "Cellular responses to DNA damage in the absence of poly (ADP-ribose) polymerase," *Biochem. Biophys. Research Comm.*, Article No. RC988257, 245, 1-10 (1998).

Said, Sami I., et al., "Excitotoxicity in the lung: N-methyl-D-aspartate-induced, nitric oxide-dependent, pulmonary edema is attenuated by vasoactive intestinal peptide and by inhibitors of poly (ADP-ribose) polymerase," *Proc. Natl. Acad. Sci. USA*, 93, 4688-4692 (May 1996).

Schlicker, A., "4-Amino-1,8-naphthalimide: a novel inhibitor of poly (ADP-ribose) polymerase and radiation sensitizer," *Int. J. Radiat. Biol.*, 75:1, 91-100 (1999).

Shimizu, T., et al., "Inhibitory effects of azelastine and tranilast on leukotriene $B_4$ and leukotriene $C_4$ generation by rat coolonic mucose," *Prostaglandins Leukotrienes and Essential Fatty Acids*, 53, 355-358 (1995).

Skehan, Philip, et al., "New colorimetric cytotoxicity assay for anticancer-drug screening," *J. Natl. Cancer Inst.*, 82:13, 1107-1112 (Jul. 4, 1990).

Southan, Garry J. and Szabo, Csaba, "Poly (ADP-ribose) polymerase inhibitors," *Current Medicinal Chemistry*, 10:4, 321-340 (2003).

Szabo, Csaba, et al., "Endothelial dysfunction in a rat model of endotoxic shock," *American Soc., Clin. Investigation.*, 100:3, 723-735 (1997)..

Tracey, W., et al., "Aldose reductase inhibition alone or combined with an adenosine A3 agonist reduces ischemic myocardial injury," *Chemical Abstract* 134:65983.

Wang, Zhao-Qi, et al., "Mice lacking ADPRT and poly (ADP-ribosyl)ation develop normally but are susceptible to skin disease," *Genes & Dev.*, 9, 509-520 (1995).

Yamaguchi, Masahisa, et al., "Novel antiasthmatic agents with dual activities of thromboxane $A_2$ synthetase inhibition and bronchodilation. 1. 2-[2-(I-Imidazolyl)alkyl]-1(2$H$)-phthalazinones," *J. Med. Chem.*, 36:25,4052-4060 (1993).

Yamaguchi, Masahisa, et al., "Novel antiasthmatic agents with dual activities of thromboxane $A_2$ synthetase inhibition and bronchodilation. 2. 4-(3-Pyridyl)-1(2$H$)-phthalazinones," *J. med. Chem.*, 36:25, 4061-4068 (1993).

Cosi, Cristina, "New inhibitors of poly(ADP-ribose) polymerase and their potential therapeutic targets," *Expert Opin. Ther. Patents* (2002) 12(7):1047-1071.

Pacher, et al., "The Role of Poly(ADP-Ribose) Polymerase Activation in the Development of Myocardial and Endothelial Dysfunction in Diabetes," *Diabetes*, 51:514-521 (2002).

Tutt, A. and Ashworth, A., "The relationship between the roles of BRCA genes in DNA repair and cancer predisposition," *TRENDS in Molecular Medicine*, (2002) 8(12):571-576.

Dusemund, "Isochino [3,2-a]phthalazin-5,8-dione", *Arch. Pharm.*, (Weinhein) 1982, pp. 925-930. (English Abstract).

Dillon, K. J., et al., *J. Biomolecular Screening*, 2003, vol. 8, No. 3, pp. 347-352.

Martin, N., et al., *J. Photochem. and PhotoBiol. B: Biology*, 2001, vol. 63, pp. 162-170.

Thompson, L. H., et al., *Mutat. Res.*, 2002, vol. 509, pp. 49-78.

Ame, Bioessays (2004) 26(8):882-893.

Calabrese, Clin. Cancer Res. (2003) 9:2711-2718.

Caldecott, Cell (2003) 112:7-10.

Chalmers, Clin. Oncol. (2004) 16(1):29-39.

Chiarugi, Trends Pharmacol. Sci. (2002) 23:122-129.

D'Amours, Nat. Rev. Mol. Cell Biol. (2002) 3:317-327.

Dantzer, Biochimie (1999) 81:69-75.

Dusemund, Arch. Pharm. (1988) 321(1):41-44.

Egawa, Int. J. Cancer (2001) 95(4):255-259.

Egawa, Oncology (2001) 61(4):293-298.

El-Tamaty, Chem. Abs. (1996) 125(23):300924j.

Ferraris, J. et al., Med. Chem. (2003) 46:3138-3151.

Griffin, et al., Nat. Cell Biol. (2000) 2:757-761.

Grube, et al., Anal. Biochem. (1991) 193:236-239.

Halldorsson, et al., FEBS Lett. (1978) 85:349-352.

Herceg, Mutat. Res. (2001) 477:97-110.

Jackson, Carcinogenesis (2002) 23:687-696.

Jijon, et al., Am. J. Phsiol. Gastrointest. Liver Physiol. (2000) 279:G641-G651.

Johnson, et al., Nature (1999) 401:397-399.

Kanaar, et al., Trends Cell Biol. (1998) 8:483-489.

Kuperstein et al., Clin. Genet. (2000) 57(3):213-220.

Kupper et al., Cancer Res. (1996) 56:2715-2717.

Lindahl, Science (1999) 286:1897-1905.

Lindahl, Trends Biochem. Sci. (1995) 20:405-411.

Lundin et al., Mol. Cell Biol. (2002) 22:5869-5878.

Lundin et al., J. Mol. Biol. (2003) 328:521-535.

Magnusson et al., Mutagenesis (1990) 5:511-514.

McNealy et al., Anticancer Res. (2003) 23:1473-1478.

Menissier De Murcia, Embo J. (2003) 22(9):2255-2263.

Morrison et al., Nature Gen. (1997) 17:479-482.

Nakamura et al., Nucleic Acids Res. (2003) 31:e104.

Pierce et al., Genes Dev. (1999) 13:2633-2638.

Samper et al., J. Cell. Biol. (2001) 154:49-60.

Satoh et al., Nature (1992) 356:356-358.

Schreiber, PNAS USA (1995) 92:4753-4757.

Schreiber et al., J. Biol. Chem. (2002) 277:23028-23036.

Seminov et al., Nucleic Acids Res. (1999) 27:4526-4531.

Shah et al., Biochim. Biophys. Acta. Mol. Cell Res. (1996) 1312:1-7.

Simbulan-Rosenthal, PNAS USA (1999) 96:13191-13196.

Szabo, "PARP as a Therapeutic Target," Zhang, Ed. CRC Press (2002) 169-204.

Tebbs, PNAS USA (1995) 92:6354-6358.

Tentori, Pharmacol. Res. (2002) 45:73-85.

Van Gent, Nat. Rev. Genet. (2001) 2:196-206.

Waldman, Nucleic Acids Res. (1991) 19:5943-5947.

Zhang, Portland Press Proc. (1999) 15:125.

Zingarelli, Immunology (2004) 113(4):509-517.

* cited by examiner

PHTHALAZINONE DERIVATIVES

This application claims the benefit to provisional application No. 60/376,497, filed Apr. 30, 2002, which is incorporated by reference herein.

The present invention relates to phthalazinone derivatives, and their use as pharmaceuticals. In particular, the present invention relates to the use of these compounds to inhibit the activity of the enzyme poly (ADP-ribose)polymerase, also known as poly(ADP-ribose)synthase and poly ADP-ribosyltransferase, and commonly referred to as PARP.

The mammalian enzyme PARP (a 113-kDa multidomain protein) has been implicated in the signalling of DNA damage through its ability to recognize and rapidly bind to DNA single or double strand breaks (D'Amours, et al., 1999, Biochem. J. 342: 249–268).

Several observations have led to the conclusion that PARP participates in a variety of DNA-related functions including gene amplification, cell division, differentiation, apoptosis, DNA base excision repair and also effects on telomere length and chromosome stability (d'Adda di Fagagna, et al., 1999, Nature Gen., 23(1): 76–80).

Studies on the mechanism by which PARP modulates DNA repair and other processes has identified its importance in the formation of poly (ADP-ribose) chains within the cellular nucleus (Althaus, F. R. and Richter, C., 1987, ADP-Ribosylation of Proteins: Enzymology and Biological Significance, Springer-Verlag, Berlin). The DNA-bound, activated PARP utilizes NAD to synthesize poly (ADP-ribose) on a variety of nuclear target proteins, including topoisomerase, histones and PARP itself (Rhun, et al., 1998, Biochem. Biophys. Res. Commun., 245: 1–10)

Poly (ADP-ribosyl)ation has also been associated with malignant transformation. For example, PARP activity is higher in the isolated nuclei of SV40-transformed fibroblasts, while both leukemic cells and colon cancer cells show higher enzyme activity than the equivalent normal leukocytes and colon mucosa (Miwa, et al., 1977, Arch. Biochem. Biophys. 181: 313–321; Burzio, et al., 1975, Proc. Soc. Exp. Bioi. Med. 149: 933–938; and Hirai, et al., 1983, Cancer Res. 43: 3441–3446).

A number of low-molecular-weight inhibitors of PARP have been used to elucidate the functional role of poly (ADP-ribosyl)ation in DNA repair. In cells treated with alkylating agents, the inhibition of PARP leads to a marked increase in DNA-strand breakage and cell killing (Durkacz, et al., 1980, Nature 283: 593–596; Berger, N. A., 1985, Radiation Research, 101: 4–14).

Subsequently, such inhibitors have been shown to enhance the effects of radiation response by suppressing the repair of potentially lethal damage (Ben-Hur, et al., 1984, British Journal of Cancer, 49 (Suppl. VI): 34–42; Schlicker, et al., 1999, Int. J. Radiat. Bioi., 75: 91–100). PARP inhibitors have been reported to be effective in radio sensitising hypoxic tumour cells (U.S. Pat. No. 5,032,617; U.S. Pat. No. 5,215,738 and U.S. Pat. No. 5,041,653).

Furthermore, PAPP knockout (PARP −/−) animals exhibit genomic instability in response to alkylating agents and γ-irradiation (Wang, et al., 1995, Genes Dev., 9: 509–520; Menissier de Murcia, et al., 1997, Proc. Natl. Acad. Sci. USA, 94: 7303–7307).

A role for PARP has also been demonstrated in certain vascular diseases, septic shock, ischaemic injury and neurotoxicity (Cantoni, et al., 1989, Biochim. Biophys. Acta, 1014: 1–7; Szabo, et al., 1997, J. Clin. Invest., 100: 723–735). Oxygen radical DNA damage that leads to strand breaks in DNA, which are subsequently recognised by PARP, is a major contributing factor to such disease states as shown by PARP inhibitor studies (Cosi, et al., 1994, J. Neurosci. Res., 39: 38–46; Said, et al., 1996, Proc. Natl. Acad. Sci. U.S.A., 93: 4688–4692). More recently, PARP has been demonstrated to play a role in the pathogenesis of haemorrhagic shock (Liaudet, et al., 2000, Proc. Natl. Acad. Sci. U.S.A., 97(3): 10203–10208). Many of these diseases arise from massive cell loss and tissue damage caused by PARP activation.

It has also been demonstrated that efficient retroviral infection of mammalian cells is blocked by the inhibition of PARP activity. Such inhibition of recombinant retroviral vector infections was shown to occur in various different cell types (Gaken, et al., 1996, J. Virology, 70(6): 3992–4000). Inhibitors of PARP have thus been developed for the use in anti-viral therapies and in cancer treatment (WO91/18591).

Moreover, PAPP inhibition has been speculated to delay the onset of aging characteristics in human fibroblasts (Rattan and Clark, 1994, Biochem. Biophys. Res. Comm., 201 (2): 665–672). This may be related to the role that PARP plays in controlling telomere function (d'Adda di Fagagna, et al., 1999, Nature Gen., 23(1): 76–80).

U.S. Pat. No. 5,874,444 discloses a number of PARP inhibitors, amongst which is 1(2H)-phthalazinone (100):

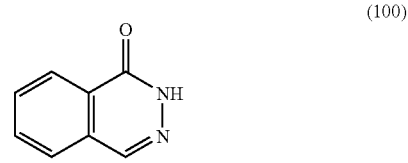

(100)

The research team which includes the present inventors have previously discovered that certain derivatives of 1(2H)-phthalazinone and related compounds exhibit inhibition of the activity of PARP, and these compounds are described in PCT/GB01/04729, filed 25 Oct. 2001 and U.S. patent application Ser. No. 10/021,506, filed on Oct. 30, 2001, which are hereby incorporated by reference.

Following further study, the present inventors have discovered that the following classes of derivatives of 1(2H)-phthalazinone and related compounds also exhibit inhibition of the activity of PARP.

The first aspect of the present invention provides a compound of formula:

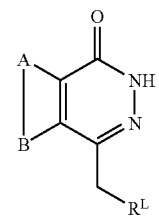

or an isomer, salt, solvate, chemically protected form, or prodrug thereof, wherein:

A and B together represent an optionally substituted, fused aromatic ring;

$R^L$ is a $C_{5-7}$ aryl group substituted in the meta position by the group $R^2$, and optionally further substituted; wherein $R^2$ is selected from:

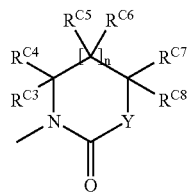

a)

wherein:

n is 0 or 1;

Y is selected from $NR^{N1}$ and $CR^{C1}R^{C2}$;

$R^{N1}$ is selected from H, optionally substituted $C_{1-10}$ alkyl, optionally substituted $C_{5-6}$ aryl and optionally substituted $C_{1-10}$ alkylacyl;

$R^{C1}$, $R^{C2}$, $R^{C3}$, $R^{C4}$, $R^{C5}$, $R^{C6}$, $R^{C7}$ and $R^{C8}$ are independently selected from H, R, SR and NHC(=O)OR, where R is optionally substituted $C_{1-10}$ alkyl or optionally substituted $C_{5-6}$ aryl;

$R^{C4}$ and $R^{C6}$ and $R^{C6}$ and $R^{C8}$ or $R^{C8}$ and $R^{C2}$ may optionally together form a double bond;

$R^{C1}$ and $R^{C2}$, $R^{C5}$ and $R^{C6}$ or $R^{C7}$ and $R^{C8}$ together with the carbon atom to which they are attached may optionally form a spiro-fused $C_{5-7}$ carbocylic or heterocyclic ring; and $R^{C5}$ and $R^{C7}$ or $R^{C7}$ and $R^{C1}$ together with the carbon atoms to which they are attached form an optionally substituted ring system;

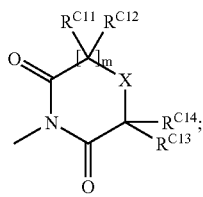

b)

wherein m is 0 or 1;

X is selected from $NR^{N2}$ and $CR^{C9}R^{C10}$;

$R^{N2}$ is selected from H, optionally substituted $C_{1-10}$ alkyl, optionally substituted $C_{5-6}$ aryl and optionally substituted $C_{1-10}$ alkylacyl;

$R^{C9}$, $R^{C10}$, $R^{C11}$, $R^{C12}$, $R^{C13}$ and $R^{C14}$ are independently selected from H, R, SR and NHC(=O)OR, where R is as defined above;

$R^{C12}$ and $R^{C10}$ or $R^{C10}$ and $R^{C14}$ may optionally together form a double bond;

$R^{C11}$ and $R^{C12}$, $R^{C9}$ and $R^{C10}$ or $R^{C13}$ and $R^{C14}$ together with the carbon atom to which they are attached may optionally form a spiro-fused $C_{5-7}$ carbocylic or heterocyclic ring; and $R^{C11}$ and $R^{C9}$ or $R^{C9}$ and $R^{C13}$ together with the carbon atoms to which they are attached may form an optionally substituted ring system.

The options for the structure of $R^2$ under a) above when n is 0 or 1 and Y is $NR^{N1}$ or $CR^{C1}R^{C2}$ are as follows:

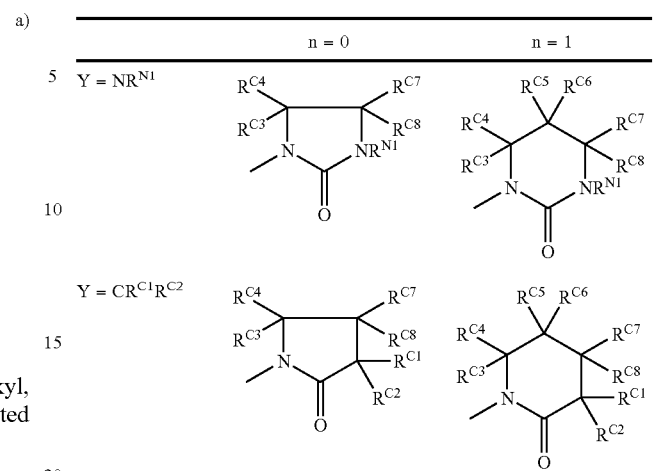

The options for the structure of $R^2$ under b) above when m is 0 or 1 and X is $NR^{N2}$ or $CR^{C9}R^{C10}$ are as follows:

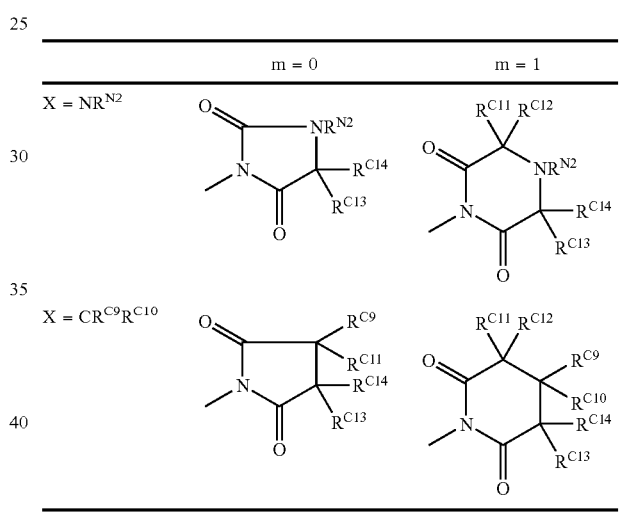

A second aspect of the present invention relates to a pharmaceutical composition comprising a compound of the first aspect and a pharmaceutically acceptable carrier or diluent.

A third aspect of the present invention provides a method of treatment of a disease of the human or animal body mediated by PARP comprising administering to such a subject a therapeutically effective amount of a compound according to the first aspect of the invention.

Diseases treatable in accordance with this aspect include: vascular disease; septic shock; haemorraghic shock; ischaemic injury, both cerebral and cardiovascular; reperfusion injury, both cerebral and cardiovascular neurotoxicity, including acute and chronic treatments for stroke and Parkinsons disease; inflammatory diseases, such as arthritis; multiple sclerosis; secondary effects of diabetes; as well as the acute treatment of cytotoxicity following cardiovascular surgery or diseases ameliorated by the inhibition of the activity of PARP;

A further aspect of the present invention relates to treatment of the human or animal body in order to inhibit the activity of PARP (PARP-1 and PARP-2), preferably in order to maximise DNA repair inhibition, comprising administering to such a subject a therapeutically effective amount of a compound according to the first aspect of the invention.

The compounds of the first aspect of the invention may also be used as adjuncts in cancer therapy or for potentiating tumour cells for treatment with ionizing radiation or chemotherapeutic agents.

In particular, compounds as defined in the first aspect of the invention can be used in anti-cancer combination therapies (or as adjuncts) along with alkylating agents, such as methyl methanesulfonate (MMS), temozolomide and dacarbazine (DTIC), also with topoisomerase-1 inhibitors like Irinotecan, Rubitecan, Exatecan, Lurtotecan, Gimetecan, Diflomotecan (homocamptothecins); as well as 7-substituted non-silatecans; the 7-silyl camptothecins, BNP 1350; and non-camptothecin topoisomerase-I inhibitors such as indolocarbazoles also dual topoisomerase-I and II inhibitors like the benzophenazines, XR 11576/MLN 576 and benzopyridoindoles. Such combinations could be given, for example, as intravenous preparations or by oral administration as dependent on the preferred method of administration for the particular agent.

Definitions

The term "fused ring system" as used herein pertains either to a system comprising in addition to the ring already defined in the formula, one or more aromatic rings, or one or more aliphatic rings.

The term "aromatic ring" is used herein in the conventional sense to refer to a cyclic aromatic structure, that is, a cyclic structure having delocalised π-electron orbitals.

The aromatic ring fused to the core rings, i.e. that formed by -A-B—, $R^{C5}$ and $R^{C7}$, $R^{C7}$ and $R^{C1}$, $R^{C11}$ and $R^{C9}$ and $R^{C9}$ and $R^{C13}$ may bear further fused aromatic rings (resulting in, e.g. naphthyl or anthracenyl groups). The aromatic ring(s) may comprise solely carbon atoms, or may comprise carbon atoms and one or more heteroatoms, including but not limited to, nitrogen, oxygen, and sulfur atoms. The aromatic ring(s) preferably have five or six ring atoms.

The aromatic ring(s) may optionally be substituted. If a substituent itself comprises an aryl group, this aryl group is not considered to be a part of the aryl group to which it is attached. For example, the group biphenyl is considered herein to be a phenyl group (an aryl group comprising a single aromatic ring) substituted with a phenyl group. Similarly, the group benzylphenyl is considered to be a phenyl group (an aryl group comprising a single aromatic ring) substituted with a benzyl group.

In one group of preferred embodiments, the aromatic group comprises a single aromatic ring, which has five or six ring atoms, which ring atoms are selected from carbon, nitrogen, oxygen, and sulfur, and which ring is optionally substituted. Examples of these groups include benzene, pyrazine, pyrrole, thiazole, isoxazole, and oxazole. 2-pyrone can also be considered to be an aromatic ring, but is less preferred.

If the aromatic ring has six atoms, then preferably at least four, or even five or all, of the ring atoms are carbon.

The other ring atoms are selected from nitrogen, oxygen and sulphur, with nitrogen and oxygen being preferred. Suitable groups include a ring with: no hetero atoms (benzene); one nitrogen ring atom (pyridine); two nitrogen ring atoms (pyrazine, pyrimidine and pyridazine); one oxygen ring atom (pyrone); and one oxygen and one nitrogen ring atom (oxazine).

If the aromatic ring has five ring atoms, then preferably at least three, or even four or all, of the ring atoms are carbon. The remaining ring atoms are selected from nitrogen, oxygen and sulphur. Suitable rings include a ring with: one nitrogen ring atom (pyrrole); two nitrogen ring atoms (imidazole, pyrazole); one oxygen ring atom (furan); one sulphur ring atom (thiophene); one nitrogen and one sulphur ring atom (isothiazole or thiazole); one nitrogen and one oxygen ring atom (isoxazole or oxazole); two nitrogen and one oxygen (oxadiazole); and four nitrogen (tetrazole).

The aromatic ring may bear one or more substituent groups at any available ring position. These substituents are selected from halo, nitro, hydroxy, ether, thiol, thioether, amino, $C_{1-10}$ (preferably $C_{1-7}$) alkyl, $C_{3-20}$ heterocyclyl and $C_{5-20}$ aryl. The aromatic ring may also bear one or more substituent groups which together form a ring. In particular these may be of formula —$(CH_2)_q$— or —O—$(CH_2)_r$—O—, where q is 2, 3, 4 or 5 and r is 1, 2 or 3.

The term "aliphatic ring" is used herein in the conventional sense to refer to a cyclic aliphatic structure, that is, a cyclic structure which is not aromatic.

The aliphatic ring fused to the core ring, i.e. that formed by $R^{C5}$ and $R^{C7}$, $R^{C7}$ and $R^{C1}$, $R^{C11}$ and $R^{C9}$ and $R^{C9}$ and $R^{C13}$ may bear further fused rings.

The aliphatic ring(s) may comprise solely carbon atoms (a carbocyclic ring), or may comprise carbon atoms and one or more heteroatoms, including but not limited to, nitrogen, oxygen, and sulfur atoms. The aliphatic ring(s) preferably have five to seven ring atoms, but may have more or less ring atoms than this.

The aliphatic ring(s) may be optionally substituted, and preferably the substituent groups are selected from halo, nitro, hydroxy, ether, thiol, thioether, amino, $C_{1-10}$ (preferably $C_{1-7}$) alkyl, $C_{3-20}$ heterocyclyl and $C_{5-20}$ aryl. In one group of preferred embodiments, the aliphatic group comprises a single aliphatic ring, which has five or six ring atoms, which ring atoms are selected from carbon, nitrogen, oxygen and sulphur, and which ring is optionally substituted. Examples of these groups include, cyclohexane, cyclohexene, cyclopentane. Further examples are described with reference to the groups from which $C_{3-7}$ heterocyclic groups are derived below.

Spiro-fused rings: The term "spiro-fused rings" as used herein pertains to a carbocyclic or heterocyclic ring which is fused to the remainder of the molecule at a single carbon atom. The ring itself may contain only carbon ring atoms, and hence be a carbocyclic ring, or may contain one or more heteroatoms and thus be a heterocyclic ring. Examples of $C_{5-7}$ carbocyclic and heterocyclic rings are given herein.

Alkyl: The term "alkyl" as used herein, pertains to a monovalent moiety obtained by removing a hydrogen atom from a hydrocarbon compound having a specified number of carbon atoms, which may be aliphatic or alicyclic, or a combination thereof, and which may be saturated, partially unsaturated, or fully unsaturated.

In the context of alkyl groups, the prefixes (e.g. $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl. Note that the first prefix may vary according to other limitations; for example, for unsaturated alkyl groups, the first prefix must be at least 2; for cyclic alkyl groups, the first prefix must be at least 3; etc.

Examples of saturated linear $C_{1-7}$ alkyl groups include, but are not limited to, methyl, ethyl, n-propyl, n-butyl, and n-pentyl (amyl).

Examples of saturated branched $C_{1-7}$ alkyl groups include, but are not limited to, iso-propyl, iso-butyl, sec-butyl, tert-butyl, and neo-pentyl.

Examples of saturated alicyclic (carbocyclic) $C_{1-7}$ alkyl groups (also referred to as "$C_{3-7}$ cycloalkyl" groups) include, but are not limited to, unsubstituted groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, cyclopropylmethyl and cyclohexylmethyl.

Examples of unsaturated $C_{1-7}$ alkyl groups which have one or more carbon-carbon double bonds (also referred to as "$C_{2-7}$ alkenyl" groups) include, but are not limited to, ethenyl (vinyl, —CH=CH$_2$), 2-propenyl (allyl, —CH$_2$—CH=CH$_2$), isopropenyl (—C(CH$_3$)=CH$_2$), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-7}$ alkyl groups which have one or more carbon-carbon double bonds (also referred to as "$C_{3-7}$ cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$ heterocyclyl: The term "$C_{3-20}$ heterocyclyl" as used herein, pertains to a monovalent moiety obtained by removing a hydrogen atom from a ring atom of a non-aromatic $C_{3-20}$ heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, azetine, pyrrolidine, pyrroline, piperidine, dihydropyridine, tetrahydropyridine, and dihydropyrrole (azoline).

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, and pyran. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulfur ring atom include, but are not limited to, those derived from thiolane (tetrahydrothiophene, thiane) and tetrahydrothiopyran.

Examples of $C_{3-20}$ heterocyclyl groups having two oxygen ring atoms include, but are not limited to, those derived from dioxane, for example 1,3-dioxane and 1,4-dioxane.

Examples of $C_{3-20}$ heterocyclyl groups having two nitrogen ring atoms include, but are not limited to, those derived from diazolidine (pyrazolidine), pyrazoline, imidazolidine, imidazoline, and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroiosoxazole, morpholine, tetrahydrooxazine, dihydrooxazine, and oxazine.

Examples of $C_{3-20}$ heterocyclyl groups having one oxygen ring atom and one sulfur ring atom include, but are not limited to, those derived from oxathiolane and oxathiane.

Examples of $C_{3-20}$ heterocyclyl groups having one nitrogen ring atom and one sulfur ring atom include, but are not limited to, those derived from thiazoline, thiazolidine, and thiomorpholine.

Other examples of $C_{3-20}$ heterocyclyl groups include, but are not limited to, oxadiazine.

If the $C_{3-20}$ heterocyclyl is substituted, the substituents are on carbon, or nitrogen (if present), atoms.

Nitrogen-containing $C_{3-20}$ heterocyclyl: The term "nitrogen-containing $C_{3-20}$ heterocyclyl" as used herein, pertains to a $C_{3-20}$ heterocyclyl group as defined above having at least one nitrogen ring atom.

$C_{5-20}$ aryl: The term "$C_{5-20}$ aryl" as used herein, pertains to a monovalent moiety obtained by removing a hydrogen atom from an aromatic ring atom of a $C_{5-20}$ aromatic compound, said compound having one ring, or two or more rings (e.g. fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups" in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, oxatriazole and tetrazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

The heteroaryl group may be bonded via a carbon or nitrogen ring atom.

Examples of $C_{5-20}$ heteroaryl groups which comprise fused rings, include, but are not limited to, $C_9$ heteroaryl groups derived from benzofuran, isobenzofuran, benzothiophene, indole, isoindole; $C_{10}$ heteroaryl groups derived from quinoline, isoquinoline, benzodiazine, pyridopyridine; $C_{14}$ heteroaryl groups derived from acridine and xanthene.

$C_{5-7}$ aryl: The term "$C_{5-7}$ aryl" as used herein, pertains to a monovalent moiety obtained by removing a hydrogen atom from an aromatic ring atom of a single $C_{5-7}$ aromatic ring having from 5 to 7 ring atoms.

If the ring atoms are all carbon, then the $C_{5-7}$ aryl group is derived from benzene, i.e. phenyl. Alternatively, the ring atoms may include one or more heteroatoms, including but not limited to oxygen, nitrogen, and sulfur, as in "heteroaryl groups". In this case, the group may conveniently be referred to as a "$C_{5-7}$ heteroaryl" group, wherein "$C_{5-7}$" denotes ring atoms, whether carbon atoms or heteroatoms. Upto 4 ring atoms may be heteroatoms.

Examples of $C_{5-7}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, oxatriazole, and tetrazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

The heteroaryl group may be bonded via a carbon or nitrogen ring atom.

Substituted in the meta position: The term "substituted in the meta position" as used herein, pertains to the substitution of the $C_{5-7}$ aryl group in a position 2 atoms away from where the group is bonded to the central moiety by —$CH_2$—. The following groups, which are given by way of example only, illustrate this position by the use of an asterix:

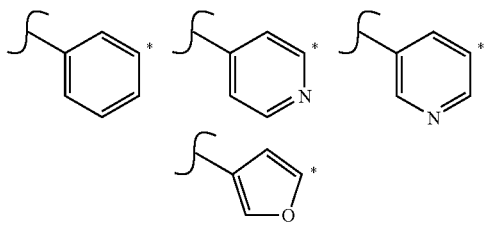

$C_{1-6}$ alkylene: The term "$C_{1-6}$ alkylene" as used herein, pertains to a bidentate moiety obtained by removing two hydrogen atoms from separate carbon atoms of an aliphatic (i.e. non-cyclic) hydrocarbon compound having from 1 to 6 carbon atoms and which may be saturated, partially unsaturated, or fully unsaturated. Thus, the term "alkylene" includes the sub-classes alkenylene and alkynylene. Examples of these groups can be derived from the examples of alkyl groups given above, and thus include: saturated alkylene groups (e.g. methylene ($C_1$), propylene ($C_3$)); saturated linear alkylene groups (e.g. methylene ($C_1$), n-propylene ($C_3$)); saturated branched alkylene groups (e.g. isopropylene ($C_3$), tert-butylene ($C_4$)); unsaturated alkenylene groups (e.g. ethenylene (—CH=CH—), isopropenylene (—C(CH_3)=CH—); unsaturated alkynylene groups (e.g. ethynylene (—C≡C—), 2-propynylene (—$CH_2$—C≡C—).

The above $C_{1-7}$ alkyl, $C_{1-4}$ alkyl, $C_{1-6}$ alkylene, $C_{3-20}$ heterocyclyl, nitrogen-containing $C_{3-20}$ heterocyclyl, $C_{5-20}$ aryl and $C_{5-7}$ aryl groups, whether alone or part of another substituent, may themselves optionally be substituted with one or more monovalent groups selected from themselves (unless otherwise stated) and the additional substituents listed below.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.
Nitro: —$NO_2$.
Cyano (nitrile, carbonitrile): —CN.
Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3$)$_3$ (butyryl), and —C(=O)Ph (benzoyl, phenone).
Carboxy (carboxylic acid): —COOH.
Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)O$CH_3$, —C(=O)O$CH_2CH_3$, —C(=O)OC($CH_3$)$_3$, and —C(=O)OPh.
Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)$NH_2$, —C(=O)NH$CH_3$, —C(=O)N($CH_3$)$_2$, —C(=O)NH$CH_2CH_3$, and —C(=O)N($CH_2CH_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinylcarbonyl.
Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —$NH_2$, —NH$CH_3$, —NHCH($CH_3$)$_2$, —N($CH_3$)$_2$, —N($CH_2CH_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. The cylic amino groups may be substituted on their ring by any of the substituents defined here, for example carboxy, carboxylate and amido. A particular form of amino group is where one of R$^1$ and R$^2$ is a sulfone (—S(=O)$_2$R), where R is a sulfone substituent, and this group can be termed a sulfonamido group. Examples of sulfonamido groups include, but are not limited to, —NHS(=O)$_2CH_3$, —NHS(=O)$_2$Ph and —NHS(=O)$_2C_6H_4$F.
Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and R$^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)$CH_3$, —NHC(=O)$CH_2CH_3$, and —NHC(=O)Ph.
One particular form of acylamido group is where R$^2$ is an amino group (—NR$^3$R$^4$), where R$^3$ and R$^4$ are independently amino substituents, as this group can be termed an ureido group. Example of ureido groups include, but are not limited to —NHC(=O)NH$CH_3$, —NHC(=O)NH$CH_2CH_3$, and —NHC(=O)NHPh.
Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$alkylthio groups include, but are not limited to, —SCH$_3$ and —SCH$_2$CH$_3$.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

In many cases, substituents are themselves substituted. For example, a $C_{1-7}$ alkyl group may be substituted with, for example, hydroxy (also referred to as a hydroxy-$C_{1-7}$ alkyl group) (e.g. —CH$_2$OH), alkoxy (also referred to as an alkoxy-$C_{1-7}$ alkyl group) (e.g. —CH$_2$OMe), amino (also referred to as a amino-$C_{1-7}$ alkyl group) (e.g. —CH$_2$NHMe), halo (also referred to as a halo-$C_{1-7}$ alkyl group) (e.g. —CF$_3$, —C$_2$F$_5$), acyloxy (also referred to as an acyloxy-$C_{1-7}$ alkyl group), acylamido (also referred to as an acylamido-$C_{1-7}$ alkyl group), and thioether (also referred to as a thioether-$C_{1-7}$ alkyl group).

Further Preferences

The following preferences can apply to each aspect of the present invention, where applicable.

In the present invention, the fused aromatic ring(s) represented by -A-B— preferably consist of solely carbon ring atoms, and thus may be benzene, naphthalene, and is more preferably benzene. As described above, these rings may be substituted, but in some embodiments are preferably unsubstituted. If a substituent is present, it is preferably in the 5-position.

$R^L$ is preferably a phenyl group, and preferably has up to one further substituent in addition to the substituent defined as $R^2$ above.

This substituent is preferably selected from halo and ether (more preferably $C_{1-4}$ alkoxy). Halo groups are more preferred, with fluoro being most preferred. This further substituent is preferably in the para position, i.e. adjacent $R^2$, and in a position 3 atoms away from where the group is bonded to the central moiety by —CH$_2$—.

$R^2$ is preferably of formula b).

$R^2$=a)

Y is preferably $CR^{C1}R^{C2}$.

n is preferably 0.

$R^{N1}$ is preferably selected from H and optionally substituted $C_{1-10}$ alkyl, more preferably H and optionally substituted $C_{1-4}$ alkyl and most preferably from H and unsubstituted $C_{1-4}$ alkyl.

$R^{C1}$ and $R^{C2}$ are preferably independently selected from H and R (more optionally substituted $C_{1-10}$ alkyl), more preferably H and optionally substituted $C_{1-4}$ alkyl and are most preferably H.

It is preferred that none of $R^{C2}$, $R^{C4}$, $R^{C6}$ and $R^{C8}$ form a double bond, and that there are no spiro-fused rings.

It is also preferred that $R^{C5}$ and $R^{C7}$ and $R^{C7}$ and $R^{C1}$ do not form an optionally substituted ring system. If there is an optionally substituted ring system, it is preferably non-aromatic and carbocyclic.

$R^{C3}$, $R_{C4}$, $R^{C5}$, $R^{C6}$, $R^{C7}$ and $R^{C8}$ are preferably independently selected from H and R (more preferably optionally substituted $C_{1-10}$ alkyl), more preferably H and optionally substituted $C_{1-4}$ alkyl and are most preferably H.

$R^2$=b)

X is preferably $CR^{C9}R^{C10}$.

m is preferably 0.

$R^{N2}$ is preferably selected from H and optionally substituted $C_{1-10}$ alkyl, more preferably H and optionally substituted $C_{1-4}$ alkyl and most preferably from H and unsubstituted $C_{1-4}$ alkyl.

$R^{C9}$ and $R^{C10}$ are preferably independently selected from H and R (more optionally substituted $C_{1-10}$ alkyl), more preferably H and optionally substituted $C_{1-4}$ alkyl and are most preferably H.

It is preferred that none of $R^{C10}$, $R^{C12}$ and $R^{C14}$ form a double bond, and that there are no spiro-fused rings. If there is a double bond it is preferably formed by $R^{C10}$ and $R^{C14}$. If there is a spiro fused ring it is preferably carbocyclic, and is preferably formed by $R^{C9}$ and $R^{C10}$.

It is also preferred that $R^{C11}$ and $R^9$ and $R^{C9}$ and $R^{C13}$ do not form an optionally substituted ring system. If there is an optionally substituted ring system, it is preferably non-aromatic and carbocyclic, and it is preferably formed by $R^{C9}$ and $R^{C13}$.

$R^{C11}$, $R^{C12}$, $R^{C13}$ and $R^{C14}$ are preferably independently selected from H and R (more preferably optionally substituted $C_{1-10}$ alkyl and optionally substituted $C_{5-7}$ aryl) and more preferably from H, optionally substituted $C_{1-4}$ alkyl and phenyl.

It is preferred that at least two of $R^{C11}$, $R^{C12}R^{C13}$ and $R^{C14}$ are H, and it is more preferred that three or four of them are H.

Compounds

Preferred compounds include, but are not limited to:

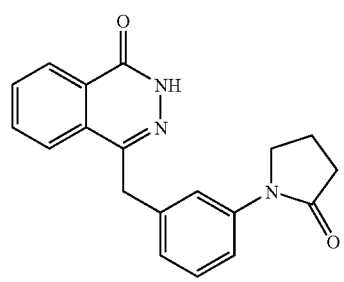

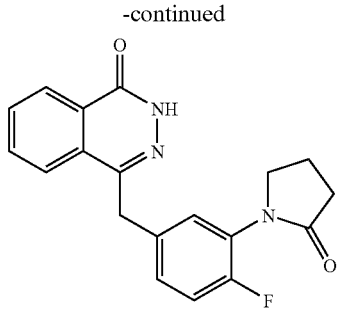
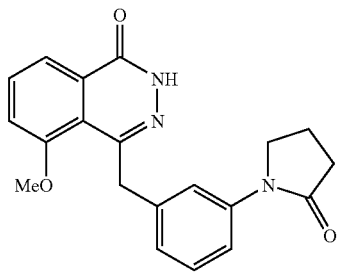
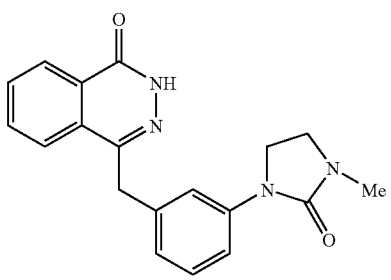
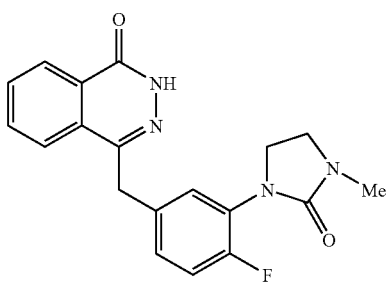
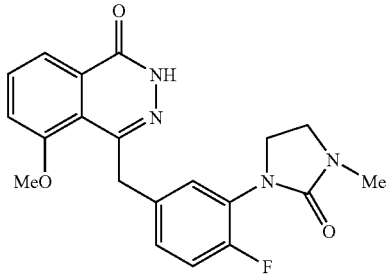
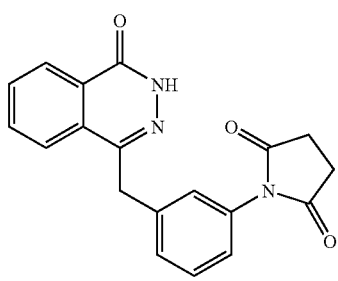

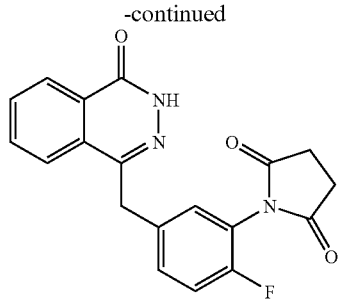
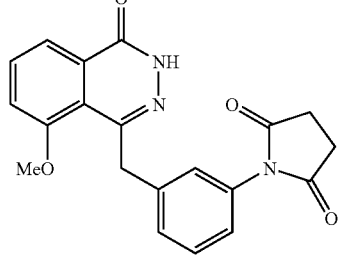

Further preferred compounds are exemplified below.

Where appropriate, the above preferences may be taken in combination with each other.

Includes other Forms

Included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms.

Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

If the compound is in crystalline form, it may exist in a number of different polymorphic forms.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Particularly relevant to the present invention is the tautomeric pair that exists when $R_N$ is H, illustrated below:

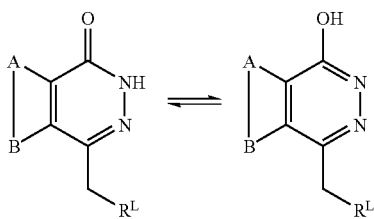

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below, as well as its different polymorphic forms.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1–19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1991).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH₃, —OAc).

For example, an aldehyde or ketone group may be protected as an acetal or ketal, respectively, in which the carbonyl group (>C=O) is converted to a diether (>C(OR)₂), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH₃) ; a benzyloxy amide (—NHCO—OCH₂C₆H₅, —NH-Cbz); as a t-butoxy amide (—NHCO—OC(CH₃)₃, —NH-Boc); a 2-biphenyl-2propoxy amide (—NHCO—OC(CH₃)₂C₆H₄C₆H₅, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO$).

For example, a carboxylic acid group may be protected as an ester for example, as: an $C_{1-7}$ alkyl ester (e.g. a methyl ester; a t-butyl ester); a $C_{1-7}$ haloalkyl ester (e.g. a $C_{1-7}$ trihaloalkyl ester); a tri$C_{1-7}$ alkylsilyl-$C_{1-7}$ alkyl ester; or a $C_{5-20}$ aryl-$C_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-7}$ alkyl (e.g. -Me, -Et); $C_{1-7}$aminoalkyl (e.g. aminoethyl; 2-(N,N-diethylamino)ethyl; 2-(4-morpholino) ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexylcarbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(=O)(OH)$_2$. Such a group can be cleared by phosphatase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (HeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis

Compounds of the present invention in which $R^L$ is a $C_{5-7}$ aryl group substituted in the meta-position by the group $R^2$, and optionally further substituted, wherein $R^2$ is the group (a), and Y is $CR^{C1}R^{C2}$ and which can therefore be represented by Formula 1:

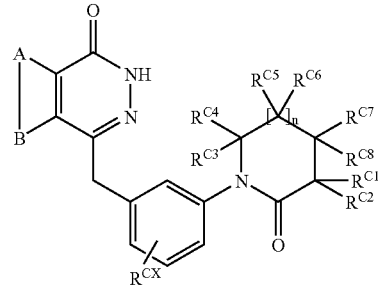

Formula 1 in which $R^{C1}$, $R^{C2}$, $R^{C3}$, $R^{C4}$, $R^{C5}$, $R^{C6}$, $R^{C7}$, $R^{C8}$, A, B and n are as defined previously and RCx is an optional substituent, for example a halogen such as fluorine, may be synthesised by reaction of a compound of Formula 2:

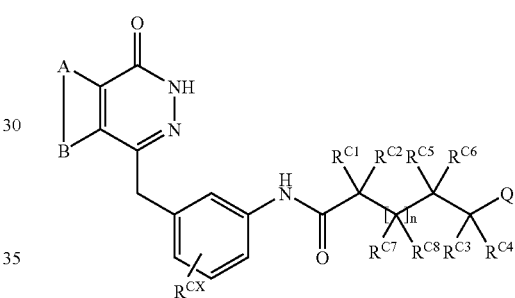

Formula 2 in which $R^{C1}$, $R^{C2}$, $R^{C3}$, $R^{C4}$, $R^{C5}$, $R^{C6}$, $R^{C7}$, $R^{C8}$, $R^{CX}$, A, B and n are as previously defined and Q is a leaving group, for example a halogen such as chlorine, with a base, for example sodium ethoxide, in a solvent, for example ethanol, at a temperature in the range of 0° C. to the boiling point of the solvent used.

Compounds of Formula 2 may be synthesised by reaction of a compound of Formula 3:

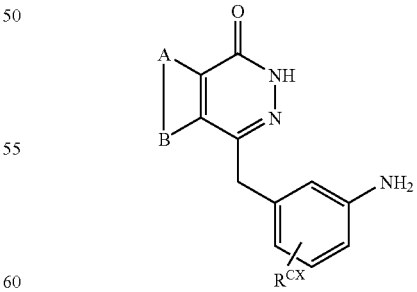

Formula 3 in which $R^{CX}$, A and B are as previously defined, with a commercially available or readily accessible compound of formula $QCR^{C3}R^{C4}CR^{C5}R^{C6}(CR^{C7}R^{C8})_nCR^{C1}R^{C2}COZ$, in which $R^{C1}$, $R^{C2}$, $R^{C3}$, $R^{C4}$, $R^{C5}$, $R^{C6}$, $R^{C7}$, $R^{C8}$ and Q are as previously defined and Z is a leaving group, for example a halogen such as chlorine, optionally in the presence of a base, for example triethylamine, in the presence of a solvent, for example dichloromethane or dioxane, at a temperature in the range of 0° C. to the boiling point of the solvent used.

Compounds of Formula 2 may also be synthesised by reaction of a compound of Formula 3 with a commercially available or readily accessible compound of formula $QCR^{C3}R^{C4}CR^{C5}R^{C6}(CR^{C7}R^{C8})_nCR^{C1}R^{C2}CO_2H$ in the presence of a coupling reagent system, for example (dimethylaminopropyl)ethylcarbodiimide hydrochloride/hydroxybenzotriazole or O-benzotriazol-1-yl-N,N,N'N'-tetramethyluronium tetrafluoroborate, in the presence of a solvent, for example dichloromethane, dimethylformamide or dimethylacetamide, in the presence of a base, for example diisopropylethylamine, at a temperature in the range of 0° C. to the boiling point of the solvent used.

Compounds of the present invention in which $R_L$ is a $C_{5-7}$ aryl group substituted in the meta-position by the group $R^2$, and optionally further substituted, wherein $R^2$ is the group (a) and Y is $NR^{N1}$, and which can therefore be represented by Formula 4:

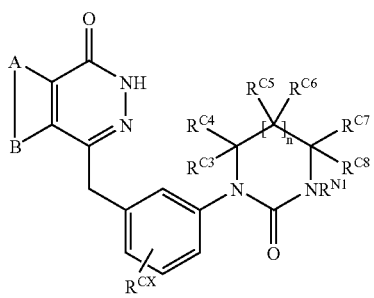

Formula 4 in which $R^{C3}$, $R^{C4}$, $R^{C5}$, $R^{C6}$, $R^{C7}$, $R^{C8}$, $R^{N1}$, $R^{CX}$, A, B and n are as defined previously, may be synthesised by reaction of a compound of Formula 5:

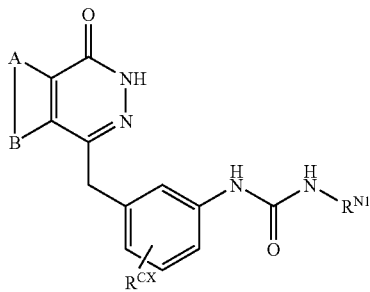

Formula 5 in which $R^{N1}$, $R^{CX}$, A and B are as previously defined, with a compound of formula $QCR^{C7}R^{C8}(CR^{C5}R^{C6})_nCR^{C3}R^{C4}Z$, in which $R^{C3}$, $R^{C4}$, $R^{C5}$, $R^{C6}$, $R^{C7}$, $R^{C8}$, n are as previously defined and Q and Z are leaving groups, for example halogens such as bromine, with a base, for example sodium hydride, in a solvent, for example tetrahydrofuran, at a temperature in the range of 0° C. to the boiling point of the solvent used.

Compounds of Formula 5 in which $R^{N1}$ is an optionally substituted $C_{1-10}$ alkyl, or optionally substituted $C_{5-7}$ aryl group, may be synthesised by reaction of a compound of Formula 3 with a compound of formula $R^{N1}NCO$ in a solvent, for example dioxane, at a temperature in the range of 0° C. to the boiling point of the solvent used.

Compounds of Formula 4 in which $R^{N1}$ is an optionally substituted $C_{1-10}$ alkyl or optionally substituted $C_{5-7}$ aryl group may also be synthesised by reaction of a compound of Formula 6:

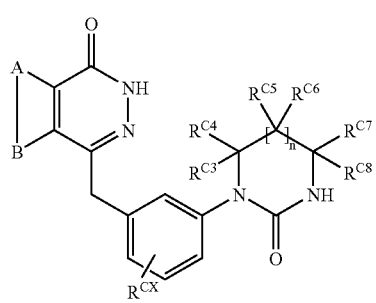

Formula 6 in which $R^{C3}$, $R^{C4}$, $R^{C5}$, $R^{C6}$, $R^{C7}$, $R^{C8}$, $R^{CX}$, A, B and n are as defined previously, with a compound of formula $R^{N1}X$, in which X is a leaving group, for example a halogen such as iodine, with a base, for example sodium hydride or potassium carbonate, in a solvent, for example tetrahydrofuran or dimethylformamide, at a temperature in the range of 0° C. to the boiling point of the solvent used.

Compounds of Formula 4 in which $R^{N1}$ is an optionally substituted $C_{1-10}$ alkylacyl group may also be synthesised by reaction of a compound of Formula 6 with a compound of formula $R^{N1}Q$, in which Q is a leaving group, for example an alkoxy group or a halogen such as chlorine, optionally in the presence of a solvent, for example dioxane, optionally in the presence of a base, for example triethylamine or pyridine, at a temperature in the range of 0° C. to the boiling point of the solvent used. They may also be synthesised by reaction of a compound of Formula 6 with a compound of formula $R^{N1}OH$, in the presence of a coupling reagent system, for example (dimethylaminopropyl)ethylcarbodiimide hydrochloride/hydroxybenzotriazole or O-benzotriazol-1-yl-N,N,N'N'-tetramethyluronium tetrafluoroborate, in the presence of a solvent, for example dichloromethane, dimethylformamide or dimethylacetamide, in the presence of a base, for example diisopropylethylamine, at a temperature in the range of 0° C. to the boiling point of the solvent used.

Compounds of Formula 6 may be synthesised by reaction of a compound of Formula 7:

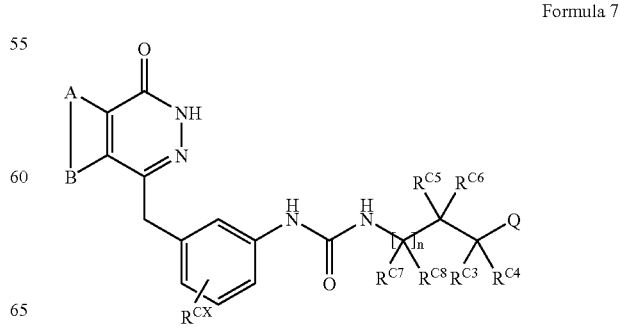

Formula 7 in which $R^{C3}$, $R^{C4}$, $R^{C5}$, $R^{C6}$, $R^{C7}$, $R^{C8}$, $R^{CX}$, A, B and n are as defined previously and Q is a leaving group, for example a halogen such as chlorine, with a base, for example sodium hydride, in a solvent, for example tetrahydrofuran, at a temperature in the range of 0° C. to the boiling point of the solvent used.

Compounds of Formula 7 may be synthesised by reaction of a compound of Formula 3 with a commercially available or readily accessible compound of formula $QCR^{C3}R^{C4}CR^{C5}R^{C6}(CR^{C7}R^{C8})_n NCO$, in which $R^{C3}$, $R^{C4}$, $R^{C5}$, $R^{C6}$, $R^{C7}$, $R^{C8}$, n and Q are as defined above, in a solvent, for example dioxane, at a temperature in the range of 0° C. to the boiling point of the solvent used.

Compounds of the present invention in which $R^L$ is a $C_{5-7}$ aryl group substituted in the meta-position by the group $R^2$, and optionally further substituted, wherein $R^2$ is the group (b), m is 0 and X is $NR^{N2}$, and which can therefore be represented by Formula 8:

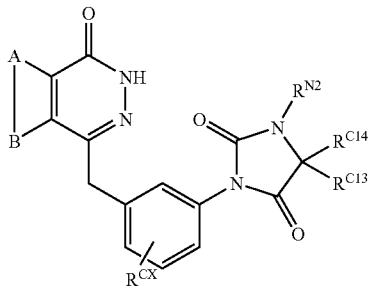

Formula 8 in which $R^{C13}$, $R^{C14}$, $R^{CX}$, A and B are as previously defined and $R^{N2}$ is optionally substituted $C_{1-10}$ alkyl or optionally substituted $C_{5-7}$ aryl, may be synthesised by reaction of a compound of Formula 8 in which $R^{N2}$ is H with an alkylating agent of formula $R^{N2}Q$, in which Q is a leaving group, for example a halogen such as bromine, in the presence of a base, for example sodium hydride, in a solvent, for example tetrahydrofuran or dimethylformamide, at a temperature in the range of 0° C. to the boiling point of the solvent used.

Compounds of Formula 8 in which $R^{CX}$, $R^{C13}$, $R^{C14}$, A and B are as previously defined and $R^{N2}$ is a $C_{1-10}$ alkylacyl group, and which may therefore be represented by Formula 9:

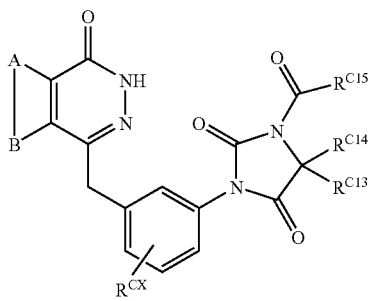

Formula 9 in which $R^{CX}$, $R^{C13}$, $R^{C14}$, A and B are as previously defined and $R^{C15}$ is an optionally substituted $C_{1-10}$ alkyl group may be synthesised by reaction of a compound of Formula 8 in which $R^{N2}$ is H with a compound of formula $R^{C15}COQ$, in which Q is a leaving group, for example an alkoxy group or a halogen such as chlorine, optionally in the presence of a solvent, for example dioxane, optionally in the presence of a base, for example triethylamine or pyridine, at a temperature in the range of 0° C. to the boiling point of the solvent used.

Compounds of Formula 9 may also be synthesised by reaction of a compound of Formula 8, in which $R^{N2}$ is H, with a compound of formula $R^{C15}CO_2H$, in the presence of a coupling reagent system, for example (dimethylaminopropyl)ethylcarbodiimide hydrochloride/hydroxybenzotriazole or O-benzotriazol-1-yl-N,N,N'N'-tetramethyluronium tetrafluoroborate, in the presence of a solvent, for example dichloromethane, dimethylformamide or dimethylacetamide, in the presence of a base, for example diisopropylethylamine, at a temperature in the range of 0° C. to the boiling point of the solvent used.

Compounds of Formula 8 in which $R^{N2}$ is H may be synthesised by reaction of a compound of Formula 3 with a commercially available or readily accessible compound of formula $EtO_2C.NH.CR^{C13}R^{C14}.CO_2Et$ in which $R^{C13}$ and $R^{C14}$ are as previously defined, optionally in a solvent, for example xylene, at a temperature in the range of 0–200° C.

Compounds of Formula 8 in which $R^{N2}$ is H may also be synthesised by reaction of a compound of Formula 3 with a commercially available or readily accessible compound of formula $OCN.CR^{C13}R^{C14}.CO_2Et$ in which $R^{C13}$ and $R^{C14}$ are as previously defined, optionally in a solvent, for example xylene, at a temperature in the range of 0–200° C.

Compounds of the present invention in which $R_L$ is a $C_{5-7}$ aryl group substituted in the meta-position by the group $R^2$, and optionally further substituted, wherein $R^2$ is the group (b), m is 1 and X is $NR^{N2}$, and which can therefore be represented by Formula 10:

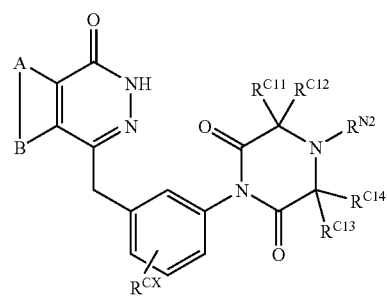

Formula 10 in which $R^{CX}$, $R^{C11}$, $R^{C12}$, $R^{C13}$, $R^{C14}$, A and B are as previously defined and $R^{N2}$ is an optionally substituted $C_{1-10}$ alkyl or optionally substituted $C_{5-7}$ aryl group may be synthesised by reaction of a compound of Formula 10 in which $R^{N2}$ is H with an alkylating agent of formula $R^{N2}Q$, in which Q is a leaving group, for example a halogen such as bromine, in the presence of a base, for example sodium hydride, in a solvent, for example tetrahydrofuran or dimethylformamide, at a temperature in the range of 0° C. to the boiling point of the solvent used. In the case of certain C5–7 aryl groups, palladium catalysts (Buchwald chemistry) may be required to effect the transformation.

Compounds of Formula 10 in which $R^{CX}$, $R^{C11}$, $R^{C12}$, $R^{C13}$, $R^{C14}$, A and B are as previously defined and $R^{N2}$ is an optionally substituted $C_{1-10}$ alkyl group of formula $—CHR^{C20}R^{C21}$ may also be synthesised by reductive alkylation of a compound of Formula 10 in which $R^{N2}$ is H with an aldehyde or ketone of formula $R^{C20}R^{C21}CO$, in which $R^{C20}$ and $R^{C21}$ are H, a $C_{1-9}$ alkyl or $C_{5-9}$ cycloalkyl, heterocyclyl, aryl or arylalkyl group or together with the atom to which they are attached form an optionally further substituted $C_{5-10}$ cycloalkyl or heterocyclyl ring, in the presence of a reducing agent, for example sodium cyanoborohydride or sodium triacetoxyborohydride, in a solvent, for example methanol or 1,2-dichloroethane, optionally in the presence of an acidic catalyst, for example acetic acid, at a temperature in the range of 0° C. to the boiling point of the solvent used.

Compounds of formula 10 in which $R^{CX}$, $R^{C11}$, $R^{C12}$, $R^{C13}$, $R^{C14}$, A and B are as previously defined and $R^{N2}$ is an optionally substituted $C_{1-10}$ alkylacyl group, and which may therefore be represented by Formula 11:

Formula 11

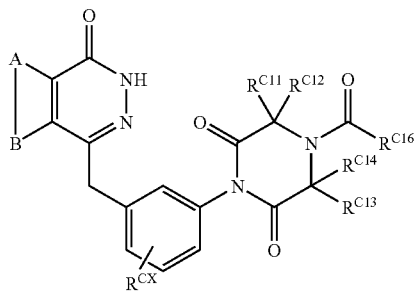

in which $R^{CX}$, $R^{C11}$, $R^{C12}$, $R^{C13}$, $R^{C14}$, A and B are as previously defined and $R^{C16}$ is optionally substituted $C_{1-10}$ alkyl may be synthesised by reaction of a compound of Formula 10 in which $R^{N2}$ is H with a compound of formula $R^{C16}COQ$, in which Q is a leaving group, for example an alkoxy group or a halogen such as chlorine, optionally in the presence of a solvent, for example dioxane, optionally in the presence of a base, for example triethylamine or pyridine, at a temperature in the range of 0° C. to the boiling point of the solvent used. They may also be synthesised by reaction of a compound of Formula 10, in which $R^{N2}$ is H, with a compound of formula $R^{C16}CO_2H$, in the presence of a coupling reagent system, for example (dimethylaminopropyl)ethylcarbodiimide hydrochloride/hydroxybenzotriazole or O-benzotriazol-1-yl-N,N,N'N'-tetramethyluronium tetrafluoroborate, in the presence of a solvent, for example dichloromethane, dimethylformamide or dimethylacetamide, in the presence of a base, for example diisopropylethylamine, at a temperature in the range of 0° C. to the boiling point of the solvent used.

Compounds of Formula 10 in which $R^{C8}$ is H may be synthesised by deprotection of a compound of Formula 12:

Formula 12

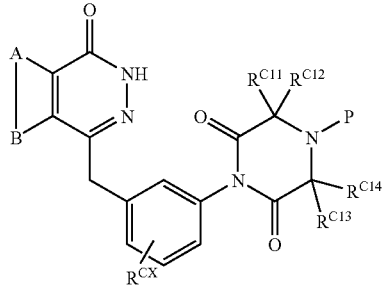

in which $R^{C11}$, $R^{C12}$, $R^{C13}$, $R^{C14}$, $R^{CX}$, A and B are as previously defined and P is an amine protecting group, for example a benzyl or tert-butoxycarbonyl group, under reaction conditions appropriate for the removal of the protecting group, for example catalytic hydrogenolysis using gaseous hydrogen or an in situ source of hydrogen, for example ammonium formate, and a catalyst, for example palladium-on-carbon, or an acid such as trifluoroacetic acid.

Compounds of Formula 12 may be synthesised by reaction of a compound of Formula 13:

Formula 13

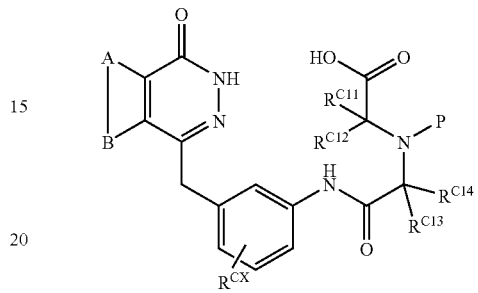

or a compound of Formula 14:

Formula 14

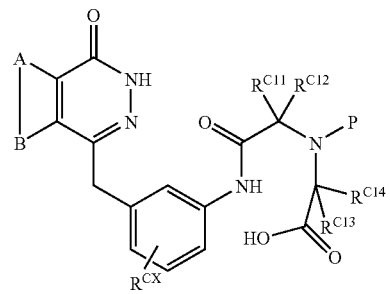

or mixtures thereof, in which $R^{C11}$, $R^{C12}$, $R^{C13}$, $R^{C14}$, $R^{CX}$, A and B are as previously defined, with a coupling reagent system, for example (dimethylaminopropyl)ethylcarbodiimide hydrochloride/hydroxybenzotriazole or O-benzotriazol-1-yl-N,N,N'N'-tetramethyluronium tetrafluoroborate, in the presence of a solvent, for example dichloromethane, dimethylformamide or dimethylacetamide, in the presence of a base, for example diisopropylethylamine, at a temperature in the range of 0° C. to the boiling point of the solvent used.

Compounds of Formula 13, 14 or mixtures thereof, may be synthesised by reaction of a compound of Formula 3 with a commercially available or readily accessible compound of Formula 15:

Formula 15

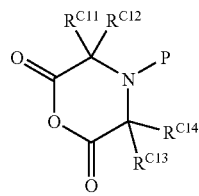

in which $R^{C11}$, $R^{C}_{12}$, $R^{C13}$, $R^{C14}$ and P are as previously defined, in the presence of a solvent, for example toluene or acetonitrile, at a temperature in the range of 0° C. to the boiling point of the solvent used.

Compounds of Formula 12 may also be synthesised directly by reaction of a compound of Formula 3 with a compound of Formula 15 in the presence of a solvent, for example acetic acid, at a temperature in the range of 0° C. to the boiling point of the solvent used.

Compounds of Formula 12 may also be synthesised directly by reaction of a compound of Formula 3 with a commercially available or readily accessible compound of formula $HO_2C.CR^{C11}R^{C12}.NP.CR^{C13}R^{C14}.CO_2H$, in which $R^{C11}$, $R^{C12}$, $R^{C13}$, $R^{C14}$ and P are as previously defined, optionally in the presence of a coupling reagent system, for example (dimethylaminopropyl)ethylcarbodiimide hydrochloride/hydroxybenzotriazole or O-benzotriazol-1-yl-N,N,N'N'-tetramethyluronium tetrafluoroborate, optionally in the presence of a solvent, for example dichloromethane, dimethylformamide or dimethylacetamide, optionally in the presence of a base, for example diisopropylethylamine, at a temperature in the range of 0° C. to the boiling point of the solvent used or, in the absence of solvent, in the range of 0° C. to 250° C.

Where the substituents are compatible with the chosen methodologies, compounds of Formula 10 and 11 may also be synthesised using the methodologies described above for the synthesis of compounds of Formula 12.

Compounds of the present invention in which $R^L$ is a $C_{5-7}$ aryl group substituted in the meta-position by the group $R^2$, and optionally further substituted, wherein $R^2$ is the group (b) and X is $CR^{C9}R^{C10}$, and which can therefore be represented by Formula 16:

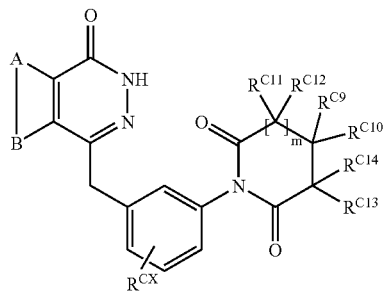

Formula 16 in which $R^{C9}$, $R^{C10}$, $R^{C11}$, $R^{C12}$, $R^{C13}$, $R^{C14}$, $R^{CX}$, A, B and m are as previously defined, may be synthesised by reaction of a compound of Formula 17:

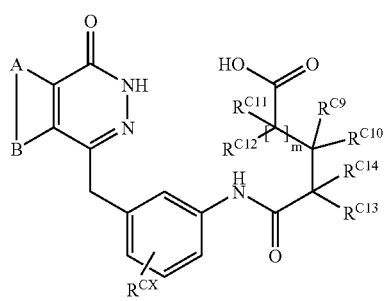

Formula 17 or a compound of Formula 18:

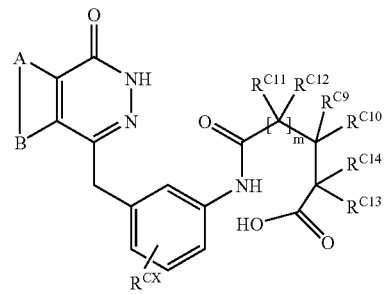

Formula 18 or mixtures thereof, in which $R^{C9}$, $R^{C10}$, $R^{C11}$, $R^{C12}$, $R^{C13}$, $R^{C14}$, $R^{CX}$, A, B and m are as previously defined, with a coupling reagent system, for example (dimethylaminopropyl)ethylcarbodiimide hydrochloride/hydroxybenzotriazole or O-benzotriazol-1-yl-N,N,N'N'-tetramethyluronium tetrafluoroborate, in the presence of a solvent, for example dichloromethane, dimethylformamide or dimethylacetamide, in the presence of a base, for example diisopropylethylamine, at a temperature in the range of 0° C. to the boiling point of the solvent used.

Compounds of Formula 17, 18 or mixtures thereof may be synthesised by reaction of a compound of Formula 3 with a commercially available or readily accessible compound of Formula 19:

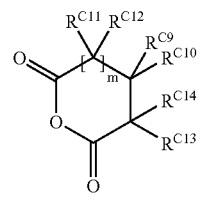

Formula 19 in which $R^{C9}$, $R^{C10}$, $R^{C11}$, $R^{C12}$, $R^{C13}$, $R^{C14}$, $R^{CX}$, A, B and m are as previously defined, in a solvent, for example toluene, at a temperature in the range of 0° C. to the boiling point of the solvent used.

Compounds of Formula 16 may also be synthesised directly by reaction of a compound of Formula 3 with a compound of Formula 19 in the presence of a solvent, for example acetic acid, at a temperature in the range of 0° C. to the boiling point of the solvent used.

Compounds of Formula 16 may also be synthesised directly by reaction of a compound of Formula 3 with a commercially available or readily accessible compound of Formula 20:

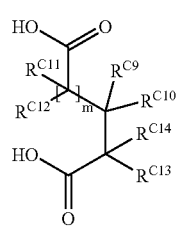

Formula 20 in which $R^{C9}$, $R^{C10}$, $R^{C11}$, $R^{C12}$, $R^{C13}$, $R^{C14}$ and m are as previously defined, optionally in the presence of a coupling reagent system, for example (dimethylaminopropyl)ethylcarbodiimide hydrochloride/hydroxybenzotriazole or O-benzotriazol-1-yl-N,N,N'N'-tetramethyluronium tetrafluoroborate, optionally in the presence of a solvent, for example dichloromethane, dimethylformamide or dimethylacetamide, optionally in the presence of a base, for example diisopropylethylamine, at a temperature in the range of 0° C. to the boiling point of the solvent used or, in the absence of solvent, in the range of 0° C. to 250° C.

Compounds of Formula 17 or 18 may also be synthesised using the above methodology, but employing a monoprotected analogue of a compound of Formula 20, for example a monoester, then deprotecting the resulting intermediate amidoester.

Compounds of Formula 3 may be synthesised by reaction of a compound of Formula 21:

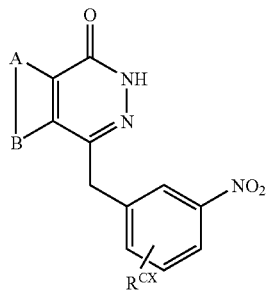

Formula 21 in which $R^{CX}$, A and B are as previously defined, with a reducing agent, for example stannous chloride, titanium trichloride, iron powder/ammonium chloride, or hydrogen in the presence of an appropriate hydrogenation catalyst, for example palladium-on-carbon, in the presence of a solvent, for example ethanol and/or water, at a temperature in the range of 0° C. to the boiling point of the solvent used, optionally at a pressure above 1 atmosphere.

Where the nature of the substituent, $R^{CX}$, is compatible with the methodologies used, compounds of Formula 21 may be synthesised by reaction of a compound of Formula 22:

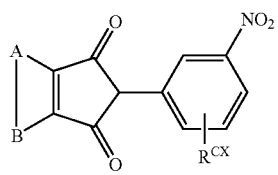

Formula 22 in which $R^{CX}$, A and B are as previously defined, with hydrazine hydrate, optionally in the presence of a solvent, for example ethanol, at a temperature in the range of 0° C. to the boiling point of the solvent or reagent used.

Where the nature of the substituent, $R^{CX}$, is compatible with the methodologies used, compounds of Formula 3 may also be synthesised directly from a compound of Formula 22 by reaction with hydrazine hydrate, optionally in the presence of a solvent, for example ethanol, at a temperature in the range of 0° C. to the boiling point of the solvent or reagent used.

Compounds of Formula 22 may be synthesised by reaction of a compound of Formula 23:

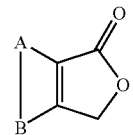

Formula 23 in which A and B are as previously defined, with a commercially available or readily accessible compound of Formula 24:

Formula 24

$$\underset{R^{CX}}{\overset{H}{\bigcirc}} \overset{O}{\underset{NO_2}{}}$$

in the presence of a base, for example sodium methoxide, lithium hexamethyldisilazide or triethylamine, in the presence of a solvent, for example methanol or tetrahydrofuran, at a temperature in the range of –80° C. to the boiling point of the solvent used.

Compounds of Formula 3 may also be synthesised by reaction of a compound of Formula 25:

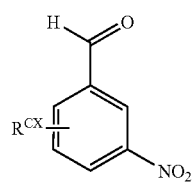

Formula 25 in which $R^{CX}$, A and B are as previously defined, with hydrazine hydrate, optionally in the presence of a solvent, for example ethanol, at a temperature in the range of 0° C. to the boiling point of the solvent or reagent used.

Compounds of Formula 25 may be synthesised by reaction of a compound of Formula 26:

Formula 26 in which $R^{CX}$, A and B are as previously defined, with a reducing agent, for example stannous chloride, titanium trichloride, iron powder/ammonium chloride, or hydrogen in the presence of an appropriate hydrogenation catalyst, for example palladium-on-carbon, in the presence of a solvent, for example ethanol and/or water, at a temperature in the range of 0° C. to the boiling point of the solvent used, optionally at a pressure above 1 atmosphere.

Compounds of Formula 26 may be synthesised by reaction of a compound of Formula 27:

Formula 27

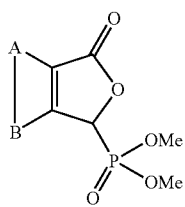

in which A and B are as previously defined, with a compound of Formula 24, in the presence of a base, for example sodium methoxide, lithium hexamethyldisilazide or triethylamine, in the presence of a solvent, for example methanol or tetrahydrofuran, at a temperature in the range of −80° C. to the boiling point of the solvent used.

Compounds of Formula 27 may be synthesised by reaction of a commercially available or readily accessible compound of Formula 28:

Formula 28

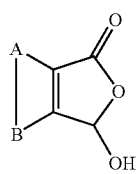

in which A and B are as previously defined, with dimethyl phosphite and a base, for example sodium methoxide, in a solvent, for example methanol, at a temperature in the range of −10° C. to the boiling point of the solvent used.

Compounds of the present invention in which $R_L$ is a phenyl group bearing additional substituents or in which the phenyl ring is replaced by a heteroaromatic moiety may be synthesised by methods analogous to those described above by use of appropriate alternative starting materials.

In addition, in the circumstance in which a compound of the present invention contains a functional group suitable for commonly employed "Functional Group Interconversion" chemistry, then the invention also claims the products of such chemistry. Relevant examples are shown below in Scheme 1:

Scheme 1

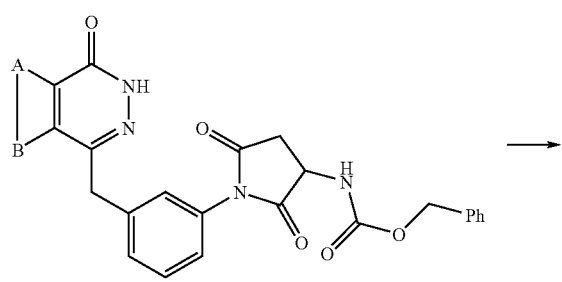

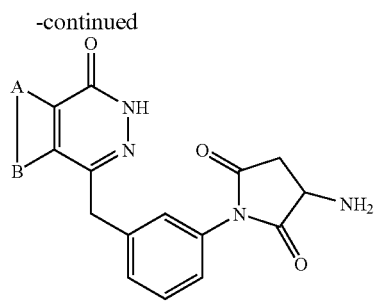

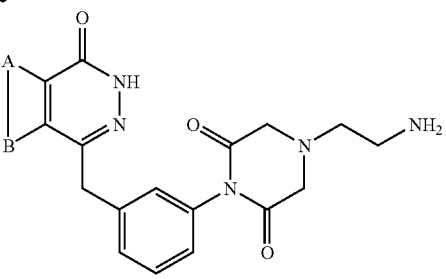

Use

The present invention provides active compounds, specifically, active in inhibiting the activity of PARP.

The term "active," as used herein, pertains to compounds which are capable of inhibiting PARP activity, and specifically includes both compounds with intrinsic activity (drugs) as well as prodrugs of such compounds, which prodrugs may themselves exhibit little or no intrinsic activity.

One assay which may conveniently be used in order to assess the PARP inhibition offered by a particular compound is described in the examples below.

The present invention further provides a method of inhibiting the activity of PARP in a cell, comprising contacting said cell with an effective amount of an active compound, preferably in the form of a pharmaceutically acceptable composition. Such a method may be practised in vitro or in vivo.

For example, a sample of cells may be grown in vitro and an active compound brought into contact with said cells, and the effect of the compound on those cells observed. As examples of "effect," the amount of DNA repair effected in a certain time may be determined. Where the active compound is found to exert an influence on the cells, this may be used as a prognostic or diagnostic marker of the efficacy of the compound in methods of treating a patient carrying cells of the same cellular type.

The term "treatment," as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "adjunct" as used herein relates to the use of active compounds in conjunction with known therapeutic means. Such means include cytotoxic regimes of drugs and/or ionising radiation as used in the treatment of different cancer types.

Active compounds may also be used as cell culture additives to inhibit PARP, for example, in order to radiosensitize cells to known chemotherapeutic or ionising radiation treatments in vitro.

Active compounds may also be used as part of an in vitro assay, for example, in order to determine whether a candidate host is likely to benefit from treatment with the compound in question.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

Formulations

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example *Remington's Pharmaceutical Sciences*, 18$^{th}$ edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

$^1$H NMR spectra were recorded using a Bruker Avance 250 spectrometer. Chemical shifts are reported in parts per million (ppm) on the δ scale relative to tetramethylsilane internal standard. Analytical LC-MS was carried out on a Micromass Platform LC-MS using a Phenomenex Luna C18 5 μm—50×2.1 mm column, mobile phase—10–90% acetonitrile/water (containing 0.4% formic acid) over 3 minutes, hold for 2 minutes, return to 10% acetonitrile over 1 minute and re-equilibrate over 4 minutes, diode array detection at 220–350 nm, cone voltage set at 30V, scan range 100–750 Daltons over 1.5s—interscan delay 0.3s, detection—+/− switching capturing positive and negative spectra.

Example 1

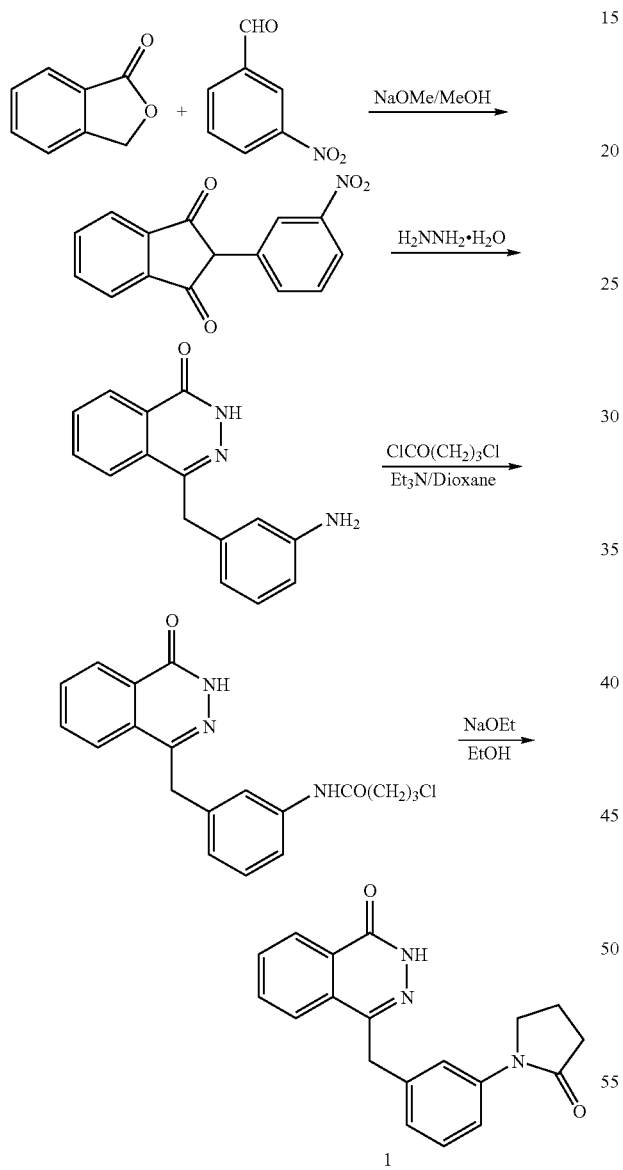

Sodium methoxide solution (27% in methanol, 400 g, 2 mol) was added over 40 minutes at 20–30° C. to a stirred mixture of phthalide (67 g, 0.5 mol), 3-nitrobenzaldehyde (75.5 g, 0.5 mol), ethyl propionate (250 ml) and methanol (150 ml). The mixture was stirred at ambient temperature for 15 minutes then it was heated under reflux for 2.5 hours, cooled to ambient temperature and poured into water (2300 ml). The aqueous mixture was washed with ether (5×500 ml) then acetic acid (60 ml) was added. The resulting solid was collected by filtration, washed with water (200 ml) and dried in vacuo to give 2-(3-nitrophenyl)indan-1,3-dione (87.92 g) as a dark red-brown solid, m.pt. 216–226° C., which was used without further purification.

A stirred mixture of 2-(3-nitrophenyl)indan-1,3-dione (85 g, 0.318 mol) and hydrazine hydrate (450 ml) was heated under reflux for 2 hours then cooled to 0° C. The resulting solid was collected by filtration, washed with water (500 ml), ground to a fine powder, mixed with sufficient cold ethanol to give a thick paste, collected by filtration and dried in vacuo at 55° C. The crude solid was then recrystallised from ethanol to give 4-(3-aminobenzyl)-2H-phthalazin-1-one (32.6 g) as a pale brown solid, m.pt. 175–177° C.

4-Chlorobutyryl chloride (5.42 g, 38.4 mmol) was added dropwise at ambient temperature to a stirred mixture of 4-(3-aminobenzyl)-2H-phthalazin-1-one (8 g, 32 mmol; prepared in a manner similar to that described above), triethylamine (5.35 ml, 38.4 mmol) and 1,4-dioxane (40 ml), the mixture was stirred at ambient temperature for 1 hour, then it was poured into ice-water (100 ml). The resulting solid was collected by filtration, washed with water (30 ml) and dried in vacuo to give 4-chloro-N-[3-(4-oxo-3,4-dihydrophthalazin-1-ylmethyl)phenyl]butyramide (12.34 g) as an off-white solid, m.pt. 180–184° C.

4-Chloro-N-[3-(4-oxo-3,4-dihydrophthalazin-1-ylmethyl)phenyl]butyramide (1 g, 2.8 mmol) was added in portions at 0° C. to a stirred solution of sodium ethoxide [from sodium (0.15 g, 6.7 mmol)] in ethanol (10 ml), then the mixture was heated under reflux for 3 hours, cooled to ambient temperature and added to ice-water (50 ml). The resulting solid was collected by filtration, washed with water (10 ml) and dried in vacuo to give 4-[3-(2-oxopyrrolidin-1-yl)benzyl]-2H-phthalazin-1-one (0.77 g) as an off-white solid, m.pt. 206–207° C.; 250 MHz $^1$H-nmr (d$_6$-DMSO) δ (ppm): 2.00 (m, 2H) (—CH$_2$CH$_2$CH$_2$—), 2.55 (m-partially obscured by DMSO peak, 2H) (—NCH$_2$—), 3.75 (t, 2H) (—COCH$_2$—), 4.3 (s, 2H) (ArCH$_2$—), 7.05 (d, 1H) (ArH), 7.25 (t, 1H) (ArH), 7.5 (d, 1H) (ArH), 7.7 (s, 1H) (ArH), 7.75–8.0 (m, 3H) (3×ArH), 8.25 (d, 1H) (ArH); m/z (M+H)$^+$ 320, 100% purity.

Example 2

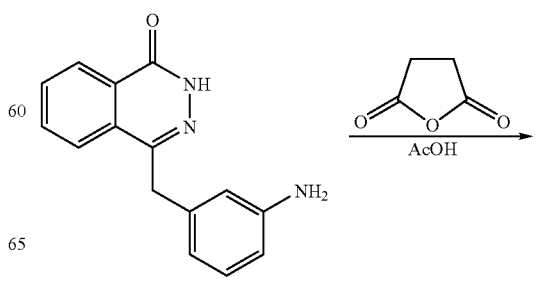

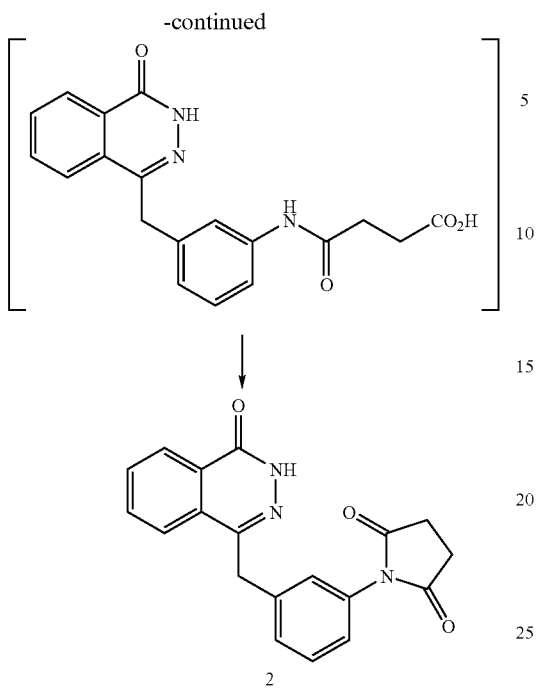

A solution of 4-(3-aminobenzyl)-2H-phthalazin-1-one (2 g, 8 mmol; prepared in a manner similar to that described in Example 1) in acetic acid (15 ml) was added to a stirred solution of succinic anhydride (0.96 g, 9.6 mmol) in acetic acid (15 ml), the mixture was heated under reflux for 4 hours, then it was allowed to stand at ambient temperature for 65 hours. Lc-ms analysis of the reaction mixture indicated it contained a mixture of the required product and the uncyclised amidoacid. The stirred mixture was heated under reflux for a further 9.25 hours and allowed to stand at ambient temperature overnight. The resulting solid was collected by filtration, washed with water (60 ml) and hexane (20 ml), and dried in vacuo to give 1-[3-(4-oxo-3,4-dihydrophthalazin-1-ylmethyl)phenyl]pyrrolidine-2,5-dione (1.142 g) as an off-white solid, 250 MHz $^1$H-nmr (d$_6$-DMSO) δ (ppm): 2.75 (s, 4H) (—CH$_2$CH$_2$—), 4.4 (s, 2H) (ArCH$_2$—), 7.15 (t, 1H) (ArH), 7.25 (s, 1H) (ArH), 7.5 (d, 2H) (2×ArH), 7.8–8.05 (m, 3H) (3×ArH), 8.3 (d, 1H) (ArH), 12.7 (s, 1H) (CONH); m/z (M+H)$^{+.}$ 334, 100% purity.

Example 3

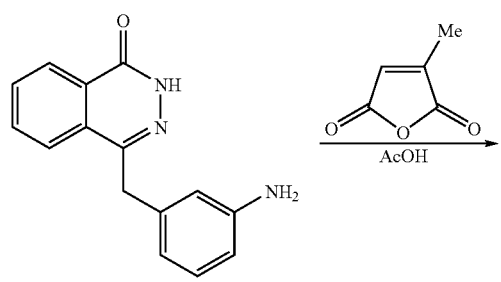

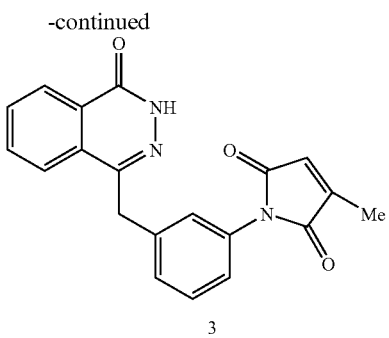

A stirred mixture of 4-(3-aminobenzyl)-2H-phthalazin-1-one (0.1 g, 0.4 mmol; prepared in a manner similar to that described in Example 1), 3-methylfuran-2,5-dione (0.045 g, 0.4 mmol) and acetic acid (4 ml) was heated under reflux for 8.25 hours and allowed to stand at ambient temperature for 65 hours, then it was diluted with water (10 ml). The resulting solid was collected by filtration, washed with water (10 ml) and dried in vacuo to give 3-methyl-1-[3-(4oxo-3,4-dihydrophthalazin-1-ylmethyl)phenyl]pyrrole-2,5-dione (0.068 g) as an off-white solid, 250 MHz $^1$H-nmr (d$_6$-DMSO) δ (ppm): 1.95 (s, 3H) (CH$_3$), 4.3 (s, 2H) (ArCH$_2$—), 6.7 (s, 1H) (—COCH=CMeCO—), 7.15 (d, 1H) (ArH), 7.2 (s, 1H) (ArH), 7.25–7.35 (m, 2H) (2×ArH), 7.7–7.9 (m, 3H) (3×ArH), 8.2 (d, 1H) (ArH), 12.55 (s, 1H) (CONH); m/z (M+H)$^{+.}$ 346, 100% purity.

The following Examples 3–14 were synthesised in a manner analogous to that described in Example 4, using appropriate starting materials, and heating under reflux until tlc indicated the reaction had progressed through the open chain amidoacid stage to the desired cyclised product (2 to 60 hours required). Any substantial variations in methodology are noted below.

Example 4

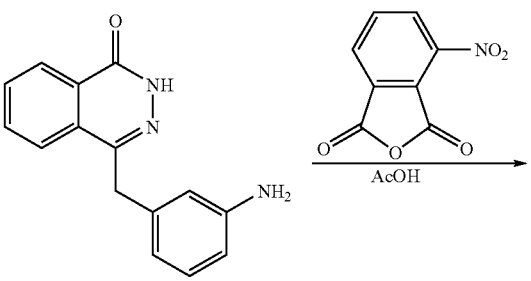

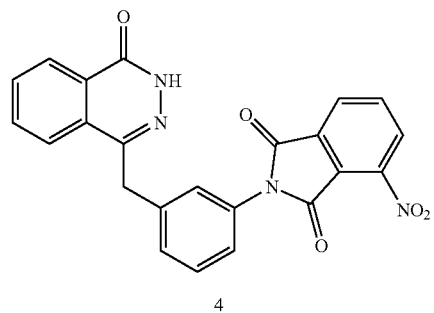

The solid product was triturated with dichloromethane (20 ml), collected by filtration and dried in vacuo to give 4-nitro-2-[3-(4-oxo-3,4-dihydrophthalazin-1-ylmethyl)phenyl]isoindole-1,3-dione (0.025 g) as a pale yellow solid, 250 MHz $^1$H-nmr (d$_6$-DMSO) δ (ppm): 4.45 (s, 2H) (ArCH$_2$—), 7.35 (t, 1H) (ArH), 7.45 (s, 1H) (ArH), 7.55 (d, 2H) (2×ArH), 7.8–8.4 (m, 7H) (7×ArH), 12.7 (s, 1H) (CONH); m/z (M+H)$^{+\cdot}$ 427, 100% purity.

Example 5

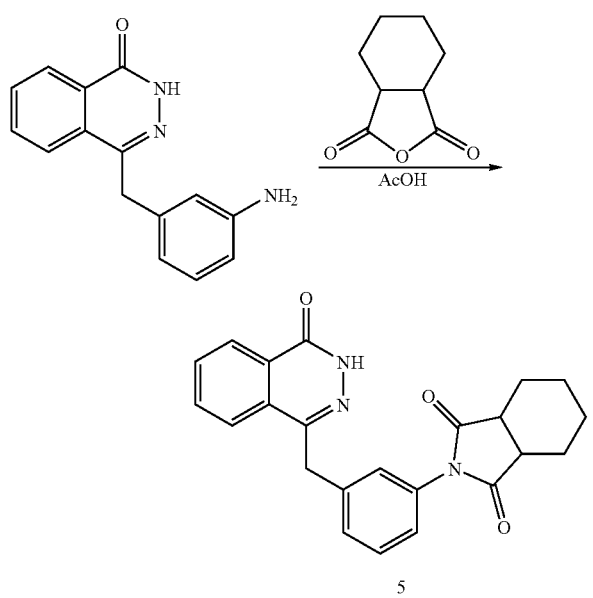

5

The product was 2-[3-(4-oxo-3,4-dihydrophthalazin-1-ylmethyl)phenyl]-3a,4,5,6,7,7a-hexahydroisoindole-1,3-dione (0.076 g), obtained as an off-white solid, 250 MHz $^1$H-nmr (d$_6$-DMSO) δ (ppm): 1.3–1.55 (m, 4H) (2×ring CH$_2$), 1.65–1.9 (m, 4H) (2×ring CH$_2$), 3.05–3.15 (m, 2H) (2×ring CH), 4.4 (s, 2H) (ArCH$_2$—), 7.2 (d, 1H) (ArH), 7.3 (s, 1H) (ArH), 7.4–7.5 (m, 2H) (2×ArH), 7.8–8.05 (m, 3H) (3×ArH), 8.3 (d, 1H) (ArH), 12.7 (s, 1H) (CONH); m/z (M+H)$^{+\cdot}$ 388, 94.7% purity.

Example 6

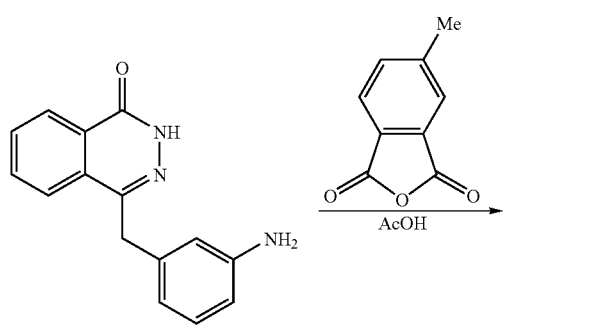

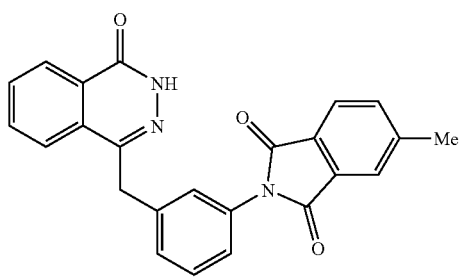

6

The product was dissolved in dichloromethane (30 ml), the solution was washed with saturated aqueous sodium hydrogencarbonate solution (10 ml) and water (10 ml), then it was dried (MgSO$_4$) and the solvent was removed in vacuo to give 5-methyl-2-[3-(4-oxo-3,4-dihydrophthalazin-1-ylmethyl)phenyl]isoindole-1,3-dione (0.055 g) as an off-white solid, 250 MHz $^1$H-nmr (d$_6$-DMSO) δ (ppm): 2.5 (s—partially obscured by DMSO peak, 3H) (CH$_3$), 4.4 (s, 2H) (ArCH$_2$—), 7.3 (d, 1H) (ArH), 7.4–7.5 (m, 3H) (3×ArH), 7.7–8.05 (m, 6H) (6×ArH), 8.3 (d, 1H) (ArH), 12.65 (s, 1H) (CONH); m/z (M+H)$^{+\cdot}$ 396, 97.1% purity.

Example 7

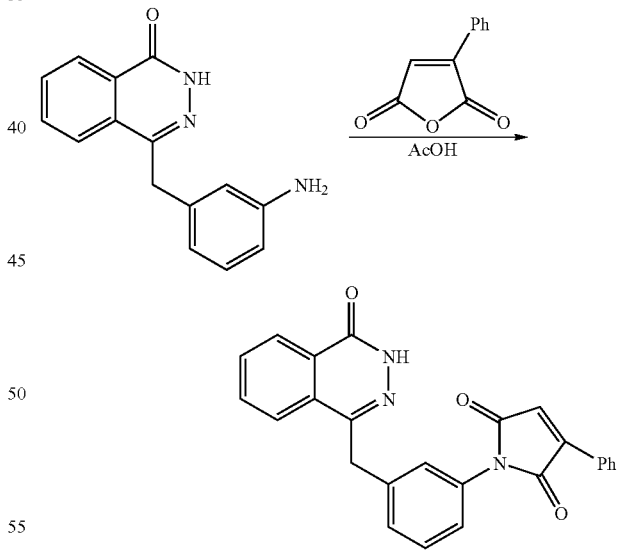

7

The product was 1-[3-(4-oxo-3,4-dihydrophthalazin-1ylmethyl)phenyl]-3-phenylpyrrole-2,5-dione (0.074 g), obtained as a tan solid, 250 MHz $^1$H-nmr (d$_6$-DMSO) δ (ppm): 4.4 (s, 2H) (ArCH$_2$—), 7.3 (d, 1H) (ArH), 7.4–7.7 (m, 7H) (6×ArH+—COCH=CPhCO), 7.85–8.15 (m, 5H) (5×ArH), 8.35 (d, 1H) (ArH), 12.7 (s, 1H) (CONH); m/z (M+H)$^{+\cdot}$ 408, 100% purity.

Example 8

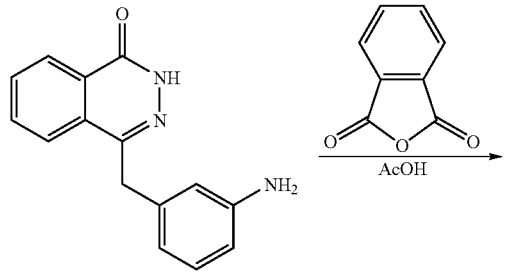

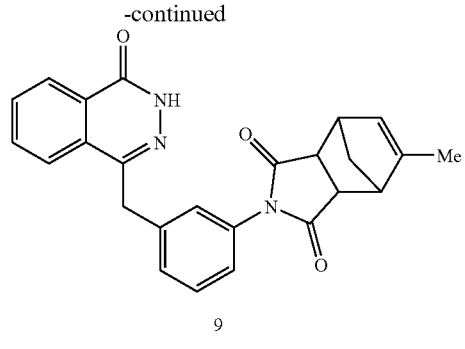

The product was dissolved in dichloromethane (20 ml), the solution was washed with saturated aqueous sodium hydrogencarbonate solution (10 ml) and water (10 ml), then it was decanted from some insoluble material, dried (MgSO$_4$) and the solvent was removed in vacuo to give 2-[3-(4-oxo-3,4-dihydrophthalazin-1-ylmethyl)phenyl]isoindole-1,3-dione (0.03 g) as a yellow solid, 250 MHz $^1$H-nmr (d$_6$-DMSO) δ (ppm): 4.45 (s, 2H) (ArCH$_2$—), 7.35 (m, 1H) (ArH), 7.4–7.55 (m, 3H) (3×ArH), 7.8–8.05 (m, 7H) (7×ArH), 8.3 (dd, 1H) (ArH), 12.7 (s, 1H) (CONH); m/z (M+H)$^+$ 382, 94.1% purity.

Example 9

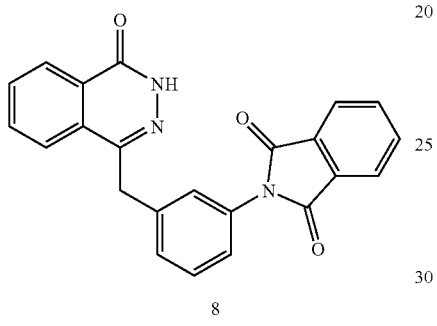

The product was purified by flash chromatography over silica using an 85:15 mixture of ethyl acetate and hexane as eluant. Appropriate fractions were combined and the solvents were removed in vacuo to give 8-methyl-4-[3-(4-oxo-3,4-dihydrophthalazin-1-ylmethyl)phenyl]-4-azatricyclo [5.2.1.0$^{2,6}$]dec-8-ene-3,5-dione (0.012 g) as a beige solid, m/z (M+H)$^+$ 412, 91.5% purity.

Example 10

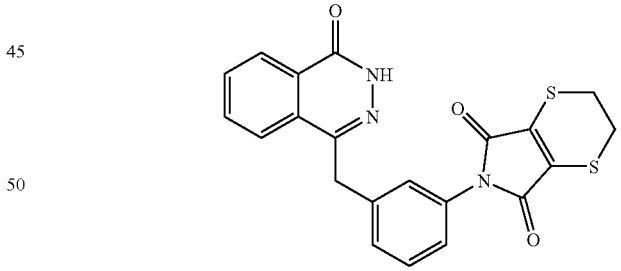

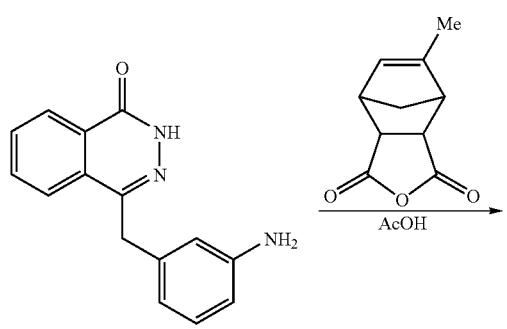

The product was dissolved in dichloromethane (30 ml), the solution was washed with saturated aqueous sodium hydrogencarbonate solution (10 ml) and water (10 ml), dried (MgSO$_4$) and the solvent was removed in vacuo to give 6-[3-(4-oxo-3,4-dihydrophthalazin-1-ylmethyl)phenyl]-2,3-dihydro[1,4]dithiino[2,3-c]pyrrole-5,7-dione (0.054 g) as a yellow solid, 250 MHz $^1$H-nmr (d$_6$-DMSO) δ (ppm): 3.6 (s, 4H) (—SCH$_2$CH$_2$S—). 4.5 (s, 2H) (ArCH$_2$—), 7.35 (m, 1H) (ArH), 7.45–7.6 (m, 3H) (3×ArH), 7.9–8.15 (m, 3H) (3×ArH), 8.4 (d, 1H) (ArH), 12.8 (s, 1H) (CONH); m/z (M+H)$^+$ 422, 100% purity.

Example 11

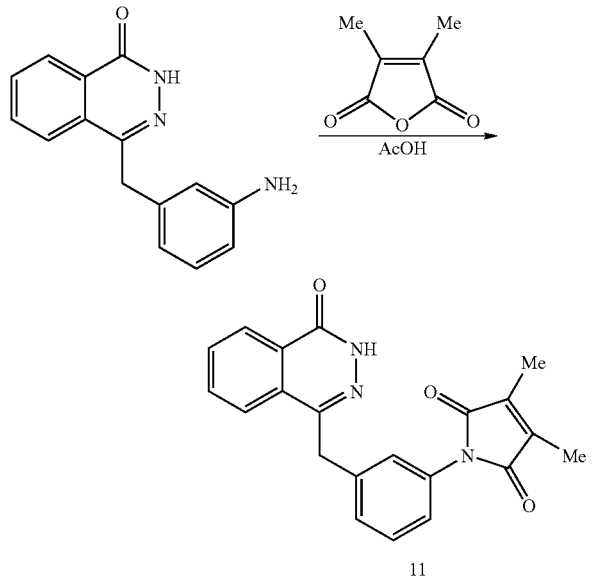

The product was 3,4-dimethyl-1-[3-(4-oxo-3,4-dihydrophthalazin-1-ylmethyl)phenyl]pyrrole-2,5-dione (0.045 g), obtained as a beige solid, 250 MHz $^1$H-nmr (d$_6$-DMSO) δ (ppm): 2.0 (s, 6H) (2×CH$_3$) 4.4 (s, 2H) (ArCH$_2$—), 7.25 (d, 1H) (ArH), 7.35 (s, 1H) (ArH), 7.4–7.55 (m, 2H) (2×ArH), 7.8–8.05 (m, 3H) (3×ArH), 8.3 (d, 1H) (ArH), 12.7 (s, 1H) (CONH); m/z (M+H)$^+$ 360, 90.3% purity.

Example 12

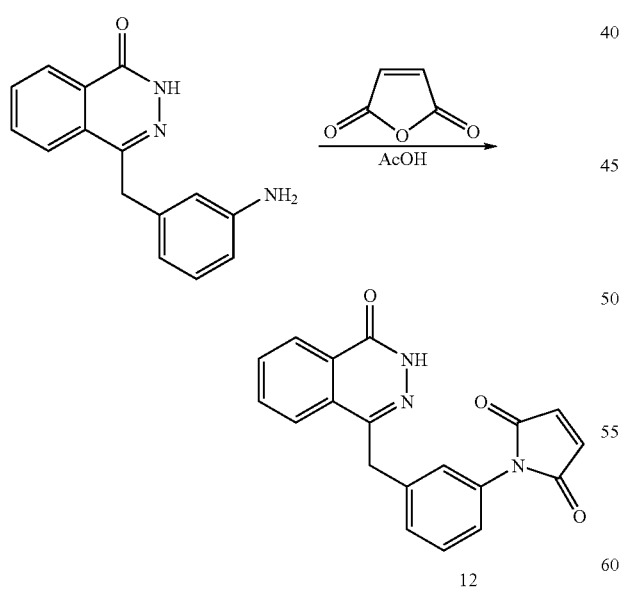

The product was 1-[3-(4-oxo-3,4-dihydrophthalazin-1-ylmethyl)phenyl]pyrrole-2,5-dione (0.026 g), obtained as a brown solid, 250 MHz $^1$H-nmr (d$_6$-DMSO) δ (ppm): 4.3 (s, 2H) (ArCH$_2$—), 7.05 (s, 2H) (—COCH=CHCO—), 7.1 (d, 1H) (ArH), 7.2 (s, 1H) (ArH), 7.25–7.4 (m, 2H) (2×ArH), 7.75–7.9 (m, 3H) (3×ArH), 8.2 (d, 1H) (ArH), 12.55 (s, 1H) (CONH); m//z (M+H)$^+$ 332, 88% purity.

Example 13

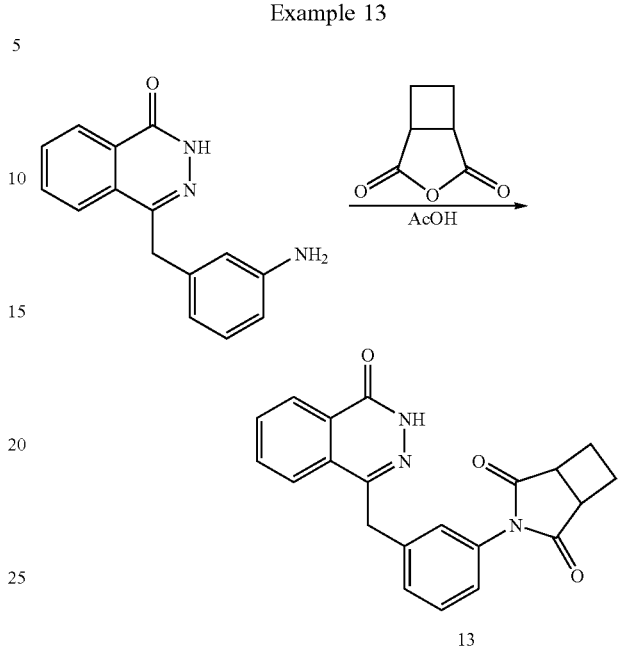

The product was 3-[3-(4-oxo-3,4-dihydrophthalazin-1-ylmethyl)phenyl]-3-azabicyclo[3.2.0]heptane-2,4-dione (0.071 g), obtained as a beige solid, 250 MHz $^1$H-nmr (d$_6$-DMSO) δ (ppm): 2.2 (m, 2H) (2×ring CH), 2.65 (m, 2H) (2×ring CH), 3.4 (m—obscured by water peak, 2H) (2×ring COCH), 4.4 (s, 2H) (ArCH$_2$—), 7.25 (d, 1H) (ArH), 7.35 (s, 1H) (ArH), 7.45–7.55 (m, 2H) (2×ArH), 7.85–8.05 (m, 3H) (3×ArH), 8.35 (d, 1H) (ArH), 12.65 (s, 1H) (CONH); m/z (M+H)$^+$ 360, 96.3% purity.

Example 14

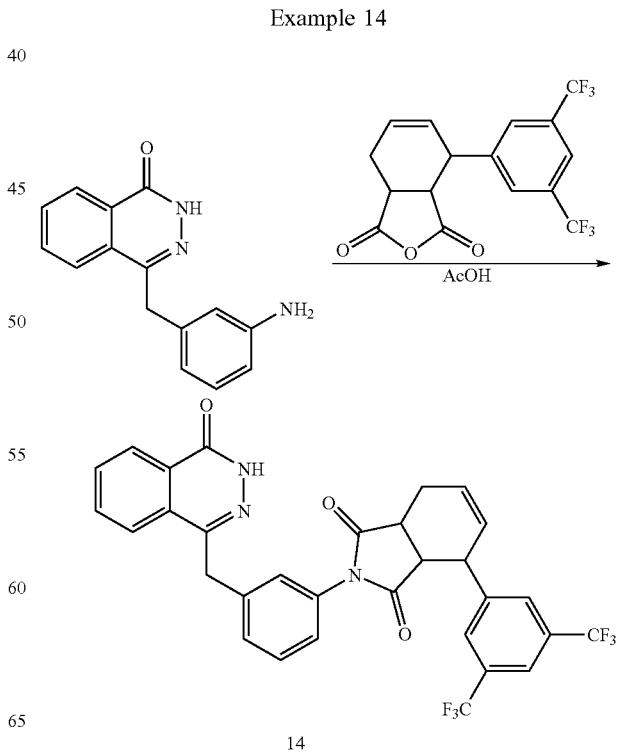

The product was dissolved in dichloromethane (20 ml), the solution was washed with saturated aqueous sodium hydrogencarbonate solution (10 ml) and water (10 ml), dried (MgSO$_4$) and the solvent was removed in vacuo to give 4-[3,5-bis-(trifluoromethyl)phenyl]-2-[3-(4-oxo-3,4-dihydrophthalazin-1-ylmethyl)phenyl]-3a,4,7,7a-tetrahydroisoindole-1,3-dione (0.073 g) as a brown solid, m/z (M+H)$^+$ 598, 79% purity.

Example 15

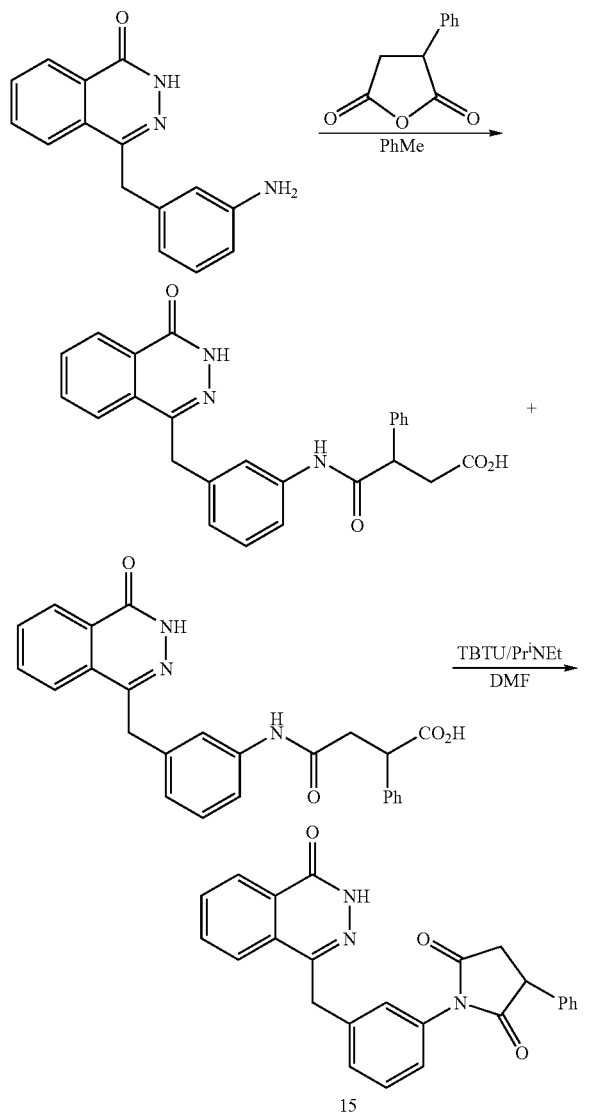

A stirred mixture of 4-(3-aminobenzyl)-2H-phthalazin-1-one (0.126 g, 0.5 mmol; prepared in a manner similar to that described in Example 1), 3-phenyldihydrofuran-2,5-dione (0.088 g, 0.5 mmol) and toluene (8 ml) was heated under reflux for 3 hours then allowed to cool to ambient temperature. The resulting solid was collected by filtration, washed with hexane (20 ml) and dried in vacuo to give a mixture of N-[3-(4-oxo-3,4-dihydrophthalazin-1ylmethyl)phenyl]-2-phenylsuccinamic acid and N-[3-(4-oxo-3,4-dihydrophthalazin-1-ylmethyl)phenyl]-3-phenylsuccinamic acid (0.142 g) as a beige solid which was used without further purification.

O-Benzotriazol-1-yl-N,N,N'N'-tetramethyluronium tetrafluoroborate (0.139 g, 0.429 mmol) and diisopropylethylamine (0.095 g, 0.726 mmol) were added sequentially at ambient temperature to a stirred solution of the above mixture of N-[3-(4-oxo-3,4-dihydrophthalazin-1-ylmethyl)phenyl]-2-phenylsuccinamic acid and N-[3-(4-oxo-3,4-dihydrophthalazin-1-ylmethyl)phenyl]-3-phenylsuccinamic acid (0.142 g, 0.33 mmol) in dimethylformamide (2 ml), the mixture was stirred at ambient temperature for 3.25 hours and allowed to stand at ambient temperature for 18 hours, then it was added dropwise to water (10 ml). The mixture was stirred at ambient temperature for 30 minutes, then the resulting solid was collected by filtration, washed with water (5 ml) and hexane (10 ml), and dried in vacuo to give 1-[3-(4-oxo-3,4-dihydrophthalazin-1-ylmethyl)phenyl]-3-phenylpyrrolidine-2,5-dione (0.097 g) as an off-white solid, 250 MHz $^1$H-nmr (d$_6$-DMSO) δ (ppm): 3.0 (m, 1H) (ring CH), 3.4 (m partially obscured by water peak, 1H) (ring CH), 4.4–4.55 (m, 3H) (ArCH$_2$—+ring CH), 7.25–7.65 (m, 9H) (9×ArH), 7.9–8.15 (m, 3H) (3×ArH), 8.4 (d, 1H) (ArH), 12.8 (s, 1H) (CONH); m/z (M+H)$^+$ 410, 94.2% purity.

The following Examples 16–20 were synthesised in a manner analogous to that described in Example 15, using appropriate starting materials, and following both reaction stages by tlc until starting materials were consumed. Any substantial variations in methodology are noted below.

Example 16

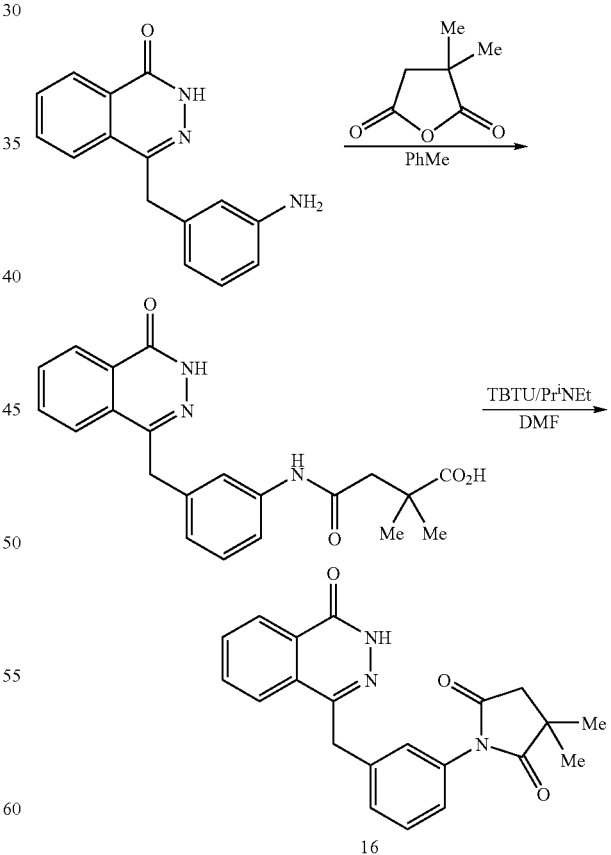

The product was 3,3-dimethyl-1-[3-(4-oxo-3,4-dihydrophthalazin-1-ylmethyl)phenyl]pyrrolidine-2,5-dione (0.066 g), obtained as an off-white solid, 250 MHz $^1$H-nmr (d$_6$-DMSO) δ (ppm): 1.55 (s, 6H) (2×CH$_3$), 3.45 (s, 2H) (ring CH$_2$), 4.4 (s, 2H) (ArCH$_2$—), 7.15 (d, 1H) (ArH), 7.3 (s, 1H) (ArH), 7.5 (m, 2H) (2×ArH), 7.8–8.05 (m, 3H) (3×ArH), 8.3 (d, 1H) (ArH), 12.65 (s, 1H) (CONH); m/z (M+H)$^+$ 362, 97.4% purity.

Example 17

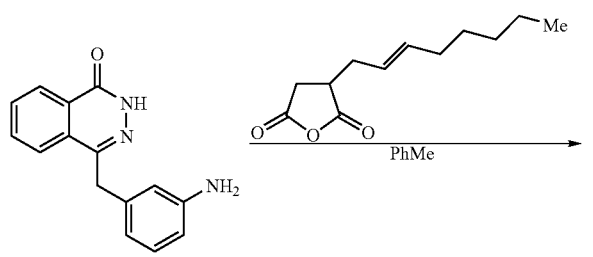

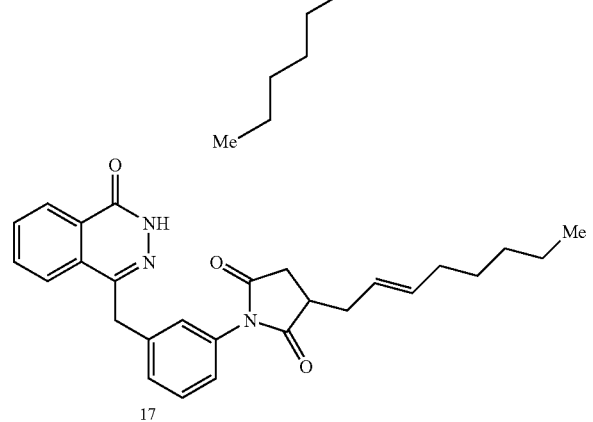

The cyclisation reaction mixture was added to water (10 ml), stirred at ambient temperature for 6 hours and allowed to stand at ambient temperature for 18 hours. The resulting solid was collected by filtration, washed with water (5 ml) and hexane (10 ml), and dried in vacuo to give 3-oct-2-enyl-1-[3-(4-oxo-3,4-dihydrophthalazin-1-ylmethyl)phenyl]pyrrolidine-2,5-dione (0.056 g) as a brown solid, 250 MHz $^1$H-nmr (d$_6$-DMSO) δ (ppm): 0.9 (m, 3H) (CH$_3$), 1.15–1.35 (m, 6H) (3×CH$_2$), 1.9–2.1 (m, 2H) (CH$_2$), 2.25–2.6 (m partially obscured by DMSO peak, 3H) (CH$_2$+ ring CH), 2.8–3.2 (m, 2H) (2 ring CH), 4.45 (s, 2H) (ArCH$_2$—), 5.35–5.7 (m, 2H) (—CH═CH—), 7.15–7.35 (m, 2H) (2×ArH), 7.5 (m, 2H) (2×ArH), 7.8–8.05 (m, 3H) (3×ArH), 8.3 (d, 1H) (ArH), 12.7 (s, 1H) (CONH); m/z (M+H)$^+$ 444, 98.0% purity.

Example 18

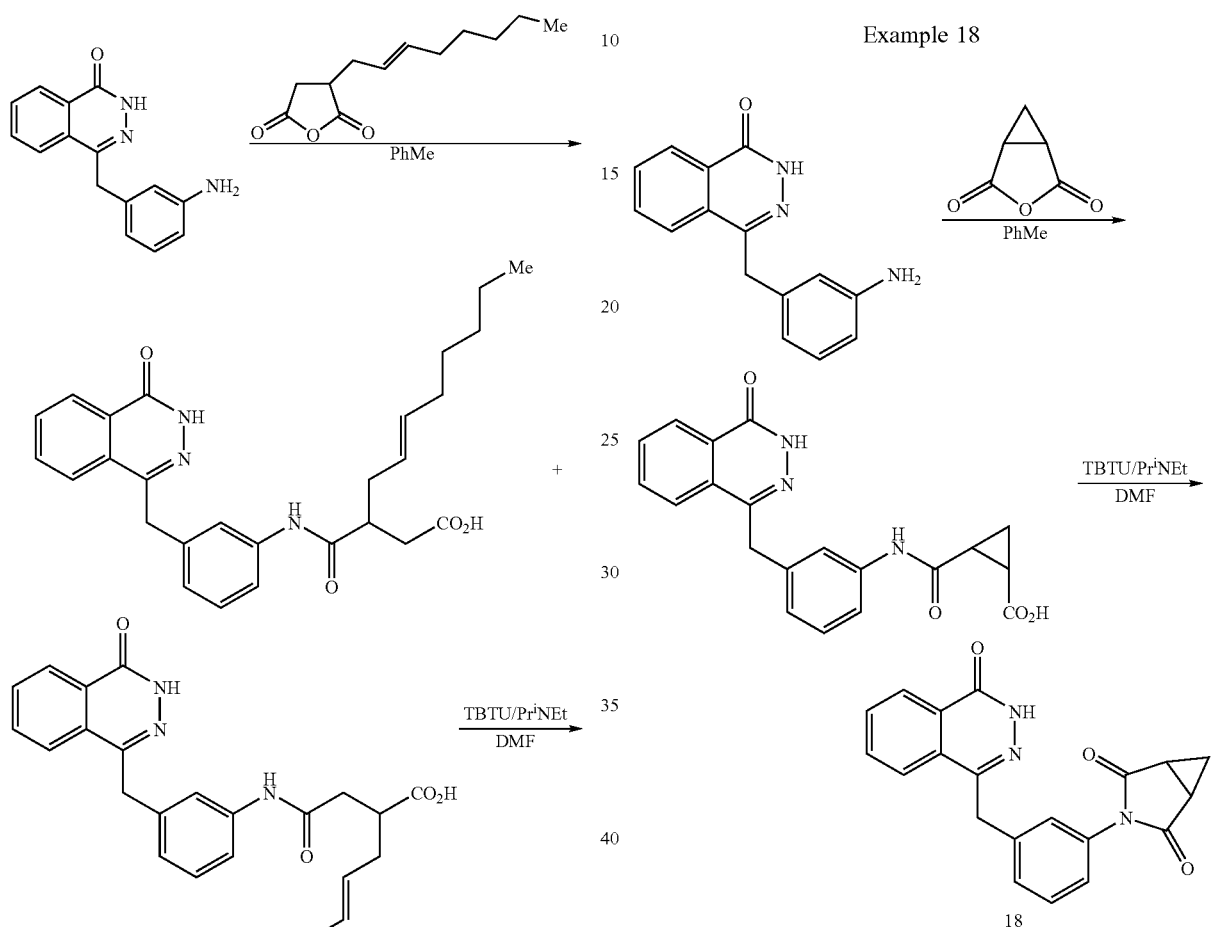

The product was 3-[3-(4-oxo-3,4-dihydrophthalazin-1-ylmethyl)phenyl]-3-azabicyclo[3.1.0]hexane-2,4-dione (0.053 g), obtained as a beige solid, 250 MHz $^1$H-nmr (d$_6$-DMSO) δ (ppm): 1.65 (m, 1H) (ring CH), 1.85 (m, 1H) (ring CH), 2.75 (m, 2H) (2×ring CH), 4.4 (s, 2H) (ArCH$_2$—), 7.15 (m, 1H) (ArH), 7.25 (s, 1H) (ArH), 7.4 (m, 2H) (2×ArH), 7.85–8.05 (m, 3H) (3×ArH), 8.3 (d, 1H) (ArH), 12.65 (s, 1H) (CONH); m/z (M+H)$^+$ 346, 95.4% purity.

Example 19

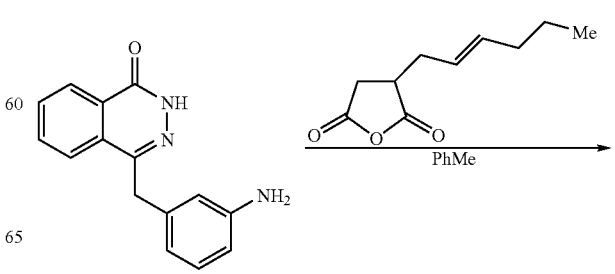

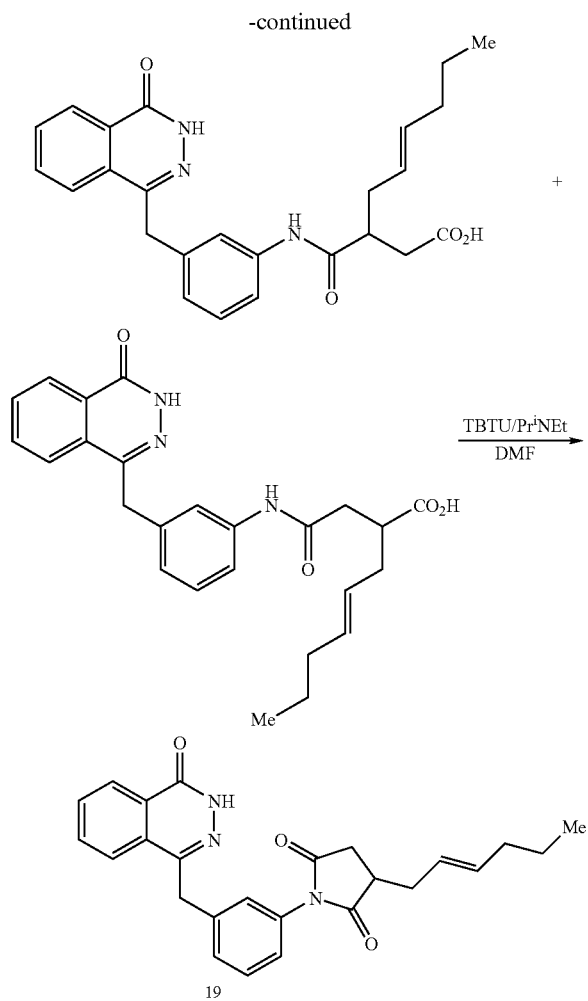

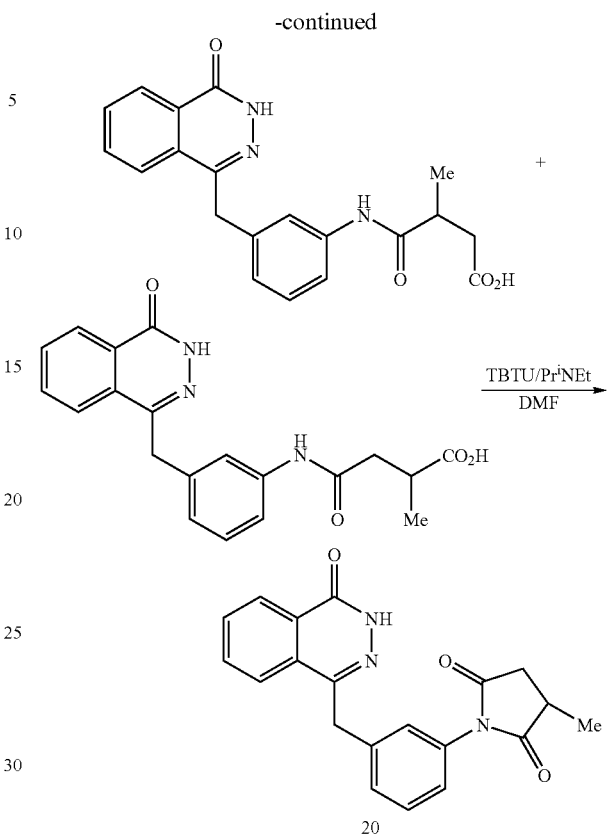

The cyclisation product was dissolved in dichloromethane (10 ml) and filtered through a short column of silica using dichloromethane as eluant. Appropriate fractions were combined and the solvent was removed in vacuo to give 3-hex-2-enyl-1-[3-(4-oxo-3,4-dihydrophthalazin-1-ylmethyl)phenyl]pyrrolidine-2,5-dione (0.04 g) as a pale brown solid, 250 MHz $^1$H-nmr (d$_6$-DMSO) δ (ppm): 0.9 (t, 3H) (CH$_3$), 1.3–1.45 (m, 2H) (CH$_2$), 1.95–2.05 (m, 2H) (CH$_2$), 2.35–2.6 (m partially obscured by DMSO peak, 2H) (CH$_2$), 2.85–3.2 (m, 3H) (3×ring CH), 4.4 (s, 2H) (ArCH$_2$—), 5.35–5.7 (m, 2H) (—CH=CH—), 7.1–7.3 (m, 2H) (2×ArH), 7.5 (m, 2H) (2×ArH), 7.85–8.05 (m, 3H) (3×ArH), 8.35 (d, 1H) (ArH), 12.7 (s, 1H) (CONH); m/z (M+H)$^+$ 416, 89.1% purity.

Example 20

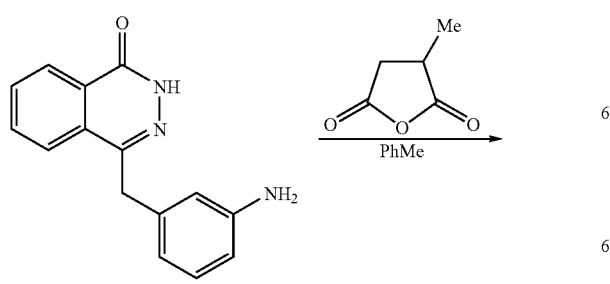

The product was 3-methyl-1-[3-(4-oxo-3,4-dihydrophthalazin-1-ylmethyl)phenyl]pyrrolidine-2,5-dione (0.086 g), obtained as a brown solid, 250 MHz $^1$H-nmr (d$_6$-DMSO) δ (ppm): 1.2 (d, 3H) (CH$_3$), 2.35–2.5 (m partially obscured by DMSO peak, 1H) (ring CH), 2.8–3.0 (m, 2H) (2×ring CH), 4.3 (s, 2H) (ArCH$_2$—), 7.05 (m, 2H) (2×ArH), 7.15 (s, 1H) (ArH), 7.35 (m, 2H) (2×ArH), 7.75–7.95 (m, 3H) (3×ArH), 8.2 (d, 1H) (ArH), 12.6 (s, 1H) (CONH); m/z (M+H)$^+$ 348, 100% purity.

Example 21

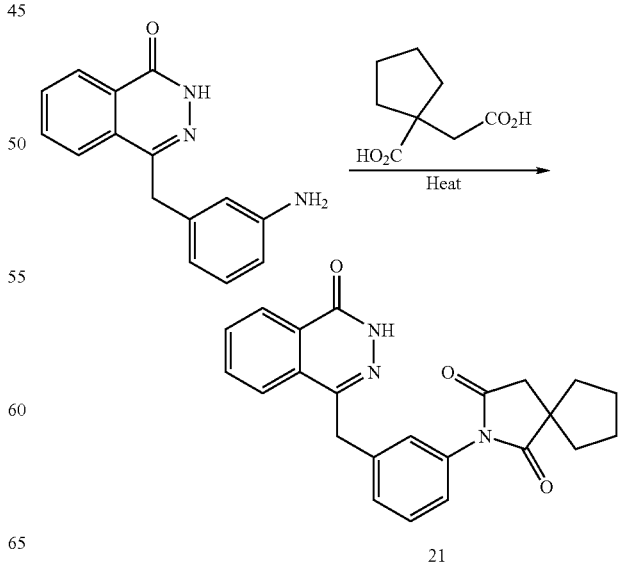

A stirred mixture of 4-(3-aminobenzyl)-2H-phthalazin-1-one (0.1 g, 0.4 mmol; prepared in a manner similar to that described in Example 1) and 1-(carboxymethyl)cyclopentanecarboxylic acid (0.0685 g, 0.4 mmol) was heated at 200° C. for 2.5 hours then it was allowed to cool to ambient temperature. Methanol (1 ml) was added and the mixture was heated under reflux for 5 minutes. No solid precipitated, so the mixture was concentrated in vacuo and the residue was triturated with water (5 ml). The resulting solid was collected by filtration and dried in vacuo to give 2-[3-(4-oxo-3,4-dihydrophthalazin-1-ylmethyl)phenyl]-2-azaspiro[4.4]nonane-1,3-dione (0.108 g) as a brown solid, m/z (M+H)$^+$ 388, 89.1% purity.

Example 22

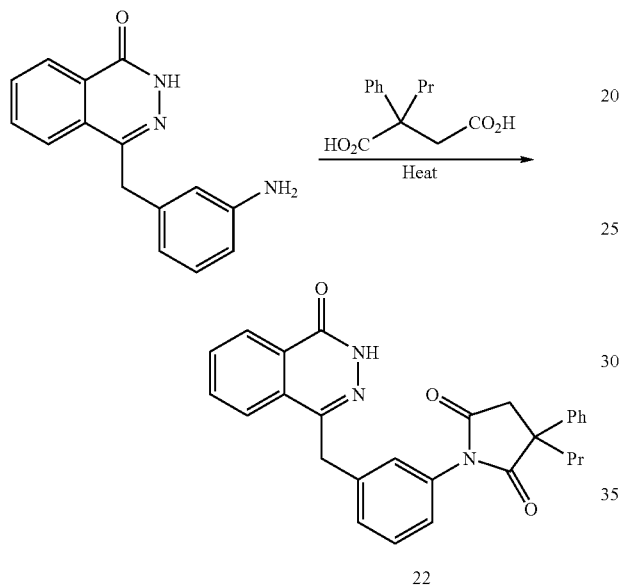

22

A stirred mixture of 4-(3-aminobenzyl)-2H-phthalazin-1-one (0.1 g, 0.4 mmol; prepared in a manner similar to that described in Example 1) and 2-phenyl-2-propylsuccinic acid (0.094 g, 0.4 mmol) was heated at 200° C. for 1.5 hours then it was allowed to stand at ambient temperature for 18 hours. Methanol (1 ml) was added, the mixture was heated under reflux for 5 minutes, then it was filtered and the collected solid was washed with hot methanol (3 ml). The combined filtrate and washings were concentrated in vacuo and the residue was triturated with water (5 ml). The resulting solid was collected by filtration and dried in vacuo to give 1-[3-(4-oxo-3,4-dihydrophthalazin-1-ylmethyl)phenyl]-3-phenyl-3-propylpyrrolidine-2,5-dione (0.061 g) as a beige solid, 250 MHz $^1$H-nmr (d$_6$-DMSO) δ (ppm): 0.95 (t, 3H) (CH$_3$), 1.25 (m, 2H) (—CH$_2$CH$_2$CH$_3$), 2.1 (m, 2H) (—CH$_2$CH$_2$CH$_3$), 3.3 (d, 2H) (ring CH$_2$), 4.4 (s, 2H) (ArCH$_2$—), 7.2 (d, 1H) (ArH), 7.3–7.65 (m, 8H) (8×ArH), 7.85–8.1 (m, 3H) (3×ArH), 8.35 (d, 1H) (ArH), 12.7 (s, 1H) (CONH); m/z (M+H)$^+$ 452, 93.6% purity.

Example 23

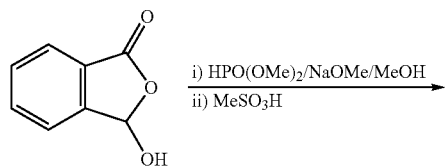

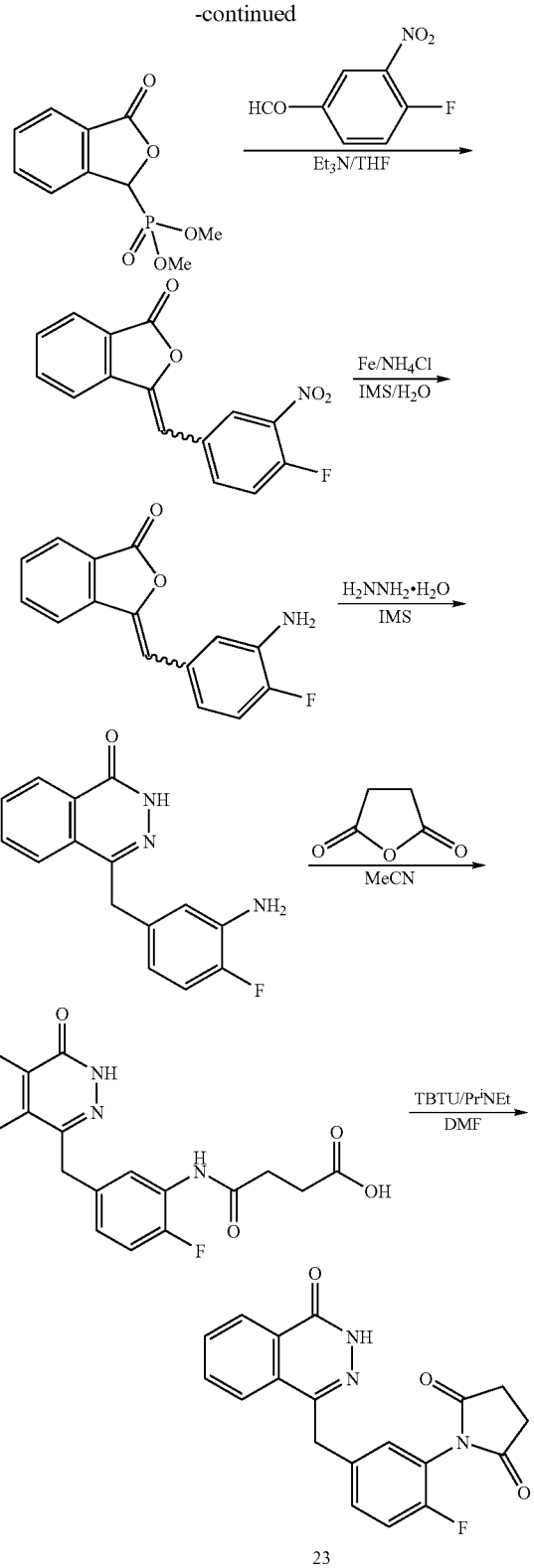

23

Dimethyl phosphite (100 g, 0.909 mol) was added dropwise at 0° C. under nitrogen to a stirred solution of sodium methoxide [from sodium (20.9 g, 0.909 gatom)] in methanol (730 ml), the mixture was stirred for 5 minutes, and 2-carboxybenzaldehyde (95.45 g, 0.64 mol) was added in portions. The stirred mixture was allowed to warm to ambient temperature, then it was stirred for 30 minutes and cooled in ice. Methanesulfonic acid (96 g, 1 mol) was added in portions at 5–10° C., then the solvent was removed in vacuo. The residue was partitioned between dichloromethane (1800 ml) and water (450 ml), and the organic layer was separated, washed with water (2×450 ml) and dried (MgSO$_4$) The solvent was removed in vacuo, the residue was triturated with ether (150 ml), and the resulting solid was collected by filtration, washed with ether (30 ml) and dried in vacuo to give dimethyl 3-oxo-1,3-dihydroisobenzofuran-1-ylphosphonate (139.94 g) as a white crystalline solid, m.pt 95–96.5° C.; 250 MHz $^1$H-nmr (d$_6$-DMSO) δ (ppm): 3.65 (d, 3H) (—OCH$_3$), 3.85 (d, 3H) (—OCH$_3$), 6.4 (d, 1H) (—CH—P), 7.75 (m, 2H) (2×ArH), 7.85–8.05 (m, 2H) (2×ArH); m/z (M+H)$^{+\cdot}$ 243, 100% purity.

A stirred solution of dimethyl 3-oxo-1,3-dihydroisobenzofuran-1-ylphosphonate (20 g, 0.083 mol) and 4-fluoro-3-nitrobenzaldehyde (13.97 g, 0.083 mol) in tetrahydrofuran (120 ml) was cooled to 15° C. and triethylamine (11.5 ml, 0.083 mol) was added dropwise at <25° C. The mixture thickened at this point, so further tetrahydrofuran (50 ml) was added to aid stirring. The mixture was stirred at ambient temperature for 65 hours and the resulting solid was collected by filtration. The filtrate was concentrated in vacuo, the residue was triturated with water (30 ml) and the resulting solid was collected by filtration. The two crops of solid were combined and suspended in water (120 ml). The mixture was stirred at ambient temperature for 30 minutes and the resulting solid was collected by filtration and dried in vacuo for 24 hours to give crude 3-(4-fluoro-3-nitrobenzylidene)-3H-isobenzofuran-1-one, still slightly wet with water, which was used directly in the next stage.

A stirred mixture of the above crude 3-(4-fluoro-3nitrobenzylidene)-3H-isobenzofuran-1-one (23.5 g), industrial methylated spirit (400 ml), water (300 ml) and ammonium chloride (8.81 g, 0.165 mol) was heated to 70° C., and iron powder (46.0 g, 0.824 gatom) was added in portions. When the addition was complete, the stirred mixture was heated at 70° C. for a further 2 hours, then it was filtered while hot through Celite. The collected inorganic solids were washed with hot industrial methylated spirit (6×200 ml), then the filtrate and washings were combined and the solvent was removed in vacuo. The residue was triturated with water (300 ml) and the resulting solid was collected by filtration and dried in vacuo for 24 hours to give crude 3-(3-amino-4-fluorobenzylidene)-3H-isobenzofuran-1-one as a yellow solid, m/z (M+H)$^{+\cdot}$ 256, 100% purity, which was used directly in the next stage.

A stirred mixture of the above crude 3-(3-amino-4-fluorobenzylidene)-3H-isobenzofuran-1-one (21 g), industrial methylated spirit (250 ml) and hydrazine monohydrate (4 ml, 0.082 mol) was heated under reflux for 1 hour then cooled to 0° C. The resulting solid was collected by filtration, washed with water (2×50 ml) and industrial methylated spirit (30 ml), and dried in vacuo to give a pale brown solid. The filtrate was concentrated in vacuo, the residue was dissolved in the minimum volume of hot industrial methylated spirit, then water was added until a solid precipitated. The resulting solid was collected by filtration and dried in vacuo. The overall yield of 4-(3-amino-4-fluorobenzyl)-2H-phthalazin-1-one was 14.5 g, m.pt. 189–191° C.; 250 MHz $^1$H-nmr (d$_6$-DMSO) δ (ppm): 4.2 (s, 2H) (ArCH$_2$—), 5.2 (s, 2H) (—NH$_2$), 6.5–6.6 (m, 1H) (ArH), 6.65–6.75 (m, 1H) (ArH), 6.9–7.05 (m, 1H) (ArH), 7.85–8.0 (m, 3H) (3×ArH), 8.3–8.4 (m, 1H) (ArH), 12.7 (s, 1H) (CONH); m/z (M+H)$^{+\cdot}$ 270, 100% purity.

A solution of 4-(3-amino-4-fluorobenzyl)-2H-phthalazin-1-one (1.62 g, 6 mmol) in acetonitrile (40 ml) was filtered to remove a trace of insoluble material. A solution of succinic anhydride (0.7 g, 7 mmol) in acetonitrile (10 ml) was filtered to remove traces of succinic acid impurity, and the two filtered solutions were combined. The stirred mixture was heated under reflux for 4 hours, allowed to stand at ambient temperature for 18 hours and heated under reflux for a further 2 hours. The resulting solid was collected by filtration from the hot mixture, washed with acetonitrile (10 ml) and dried in vacuo. The solid was suspended in dichloromethane (60 ml), the mixture was heated under reflux for 2 hours, then the resulting solid was collected by filtration from the hot mixture, washed with dichloromethane (20 ml) and dried in vacuo to give N-[2-fluoro-5-(4-oxo-3,4-dihydrophalazin-1-ylmethyl)phenyl]succinamic acid (1.73 g) as an off-white solid, m.pt. 210–213° C.; 250 MHz $^1$H-nmr (d$_6$-DMSO) δ (ppm): 2.4–2.7 (m, 4H) (—CH$_2$CH$_2$—) 4.4 (s, 2H) (ArCH$_2$—), 7.0–7.25 (m, 2H) (2×ArH), 7.7–8.0 (m, 4H) (4×ArH), 8.2–8.3 (m, 1H) (ArH), 9.7 (s, 1H) (chain CONH), 12.15 (br s, 1H) (—CO$_2$H), 12.65 (s, 1H) (ring CONH); m/z (M+H)$^{+\cdot}$ 370, 96% purity.

O-Benzotriazol-1-yl-N,N,N'N'-tetramethyluronium tetrafluoroborate (0.834 g, 2.6 mmol) and diisopropylethylamine (0.569 g, 4.4 mmol) were added sequentially at ambient temperature to a stirred solution of N-[2-fluoro-5-(4-oxo-3,4-dihydrophalazin-1-ylmethyl)phenyl]succinamic acid (0.703 g, 2 mmol) in dimethylformamide (2 ml), and the mixture was stirred at ambient temperature for 100 hours. Tlc indicated that starting material remained, so further O-benzotriazol-1-yl-N,N,N'N'-tetramethyluronium tetrafluoroborate (0.3 g) was added and stirring was continued for 24 hours. The resulting suspension was added dropwise to water (40 ml), the mixture was stirred at ambient temperature for 1 hour, and the resulting solid was collected by filtration, washed with water (20 ml) and hexane (20 ml), and dried in vacuo to give 1-[2-fluoro-5-(4-oxo-3,4-dihydrophalazin-1-ylmethyl)phenyl]pyrrolidine-2,5-dione (0.476 g) as an off-white solid, 258–262° C.; 250 MHz $^1$H-nmr (d$_6$-DMSO) δ (ppm): 2.75–2.9 (m, 4H) (—CH$_2$CH$_2$—) 4.25 (s, 2H) (ArCH$_2$—), 7.25 (m, 1H) (ArH), 7.35 (t, 1H) (ArH), 7.5–7.6 (m, 1H) (ArH), 7.8–8.05 (m, 3H) (3×ArH), 8.25 (d, 1H) (ArH), 12.65 (s, 1H) (CONH).

Example 24

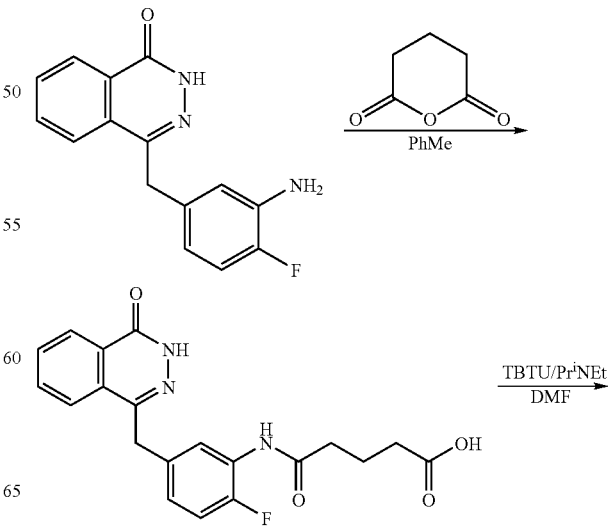

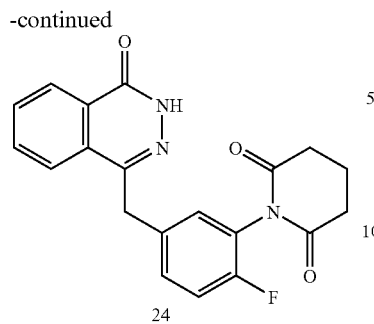

24

A stirred mixture of 4-(3-amino-4-fluorobenzyl)-2H-phthalazin-1-one (0.1 g, 0.37 mmol; prepared in a manner similar to that described in Example 23), glutaric anhydride (0.042 g, 0.37 mmol) and toluene (10 ml) was heated under reflux until the starting materials were consumed (the reaction was followed by tlc using a 3:1 mixture of ethyl acetate and ethanol as eluant), then it was allowed to cool to ambient temperature. The resulting solid was collected by filtration and recrystallised from ethanol to give 4-[2-fluoro-5-(4-oxo-3,4-dihydrophthalazin-1-ylmethyl)phenylcarbamoyl]butyric acid (0.08 g) as a white solid, mpt. 190–194° C.; 250 MHz $^1$H-nmr (d$_6$-DMSO) δ (ppm): 1.5–1.65 (m, 2H) (—CH$_2$CH$_2$CH$_2$—), 2.0–2.25 (m, 4H) (—CH$_2$CH$_2$CH$_2$—) 4.1 (s, 2H) (ArCH$_2$—), 6.8–7.0 (m, 2H) (2×ArH), 7.5–7.8 (m, 4H) (4×ArH), 8.05 (d, 1H) (ArH), 9.45 (s, 1H) (chain CONH), 12.85 (br s, 1H) (—CO$_2$H), 12.4 (s, 1H) (ring CONH); m/z (M–H)$^{+\cdot}$ 382, 100% purity.

O-Benzotriazol-1-yl-N,N,N'N'-tetramethyluronium tetrafluoroborate (0.087 g, 0.27 mmol) and diisopropylethylamine (0.079 ml, 0.46 mmol) were added sequentially at ambient temperature to a stirred solution of 4-[2-fluoro-5-(4-oxo-3,4-dihydrophthalazin-1-ylmethyl)phenylcarbamoyl]butyric acid (0.08 g, 0.21 mmol) in dimethylformamide (2 ml), the mixture was stirred at ambient temperature for 50 hours, then it was added dropwise to ice-cold water (10 ml). The resulting solid was collected by filtration and dried in vacuo to give 1-[2-Fluoro-5-(4-oxo-3,4-dihydrophthalazin-1-ylmethyl)phenyl]piperidine-2,6-dione (0.05 g) as a white solid, m.pt. 259–263° C.; 250 MHz $^1$H-nmr (d$_6$-DMSO) δ (ppm): 1.8–2.1 (m, 2H) (—CH$_2$CH$_2$CH$_2$—), 2.7–2.9 (m, 4H) (—CH$_2$CH$_2$CH$_2$—) 4.35 (s, 2H) (ArCH$_2$—), 7.1–7.35 (m, 2H) (2×ArH), 7.4–7.5 (m, 1H) (ArH), 7.8–8.05 (m, 3H) (3×ArH), 8.3 (d, 1H) (ArH), 12.65 (s, 1H) (CONH); m/z (M+H)$^+$ 366, 100% purity.

Example 25

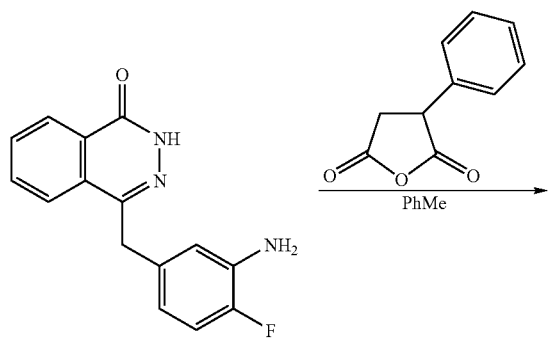

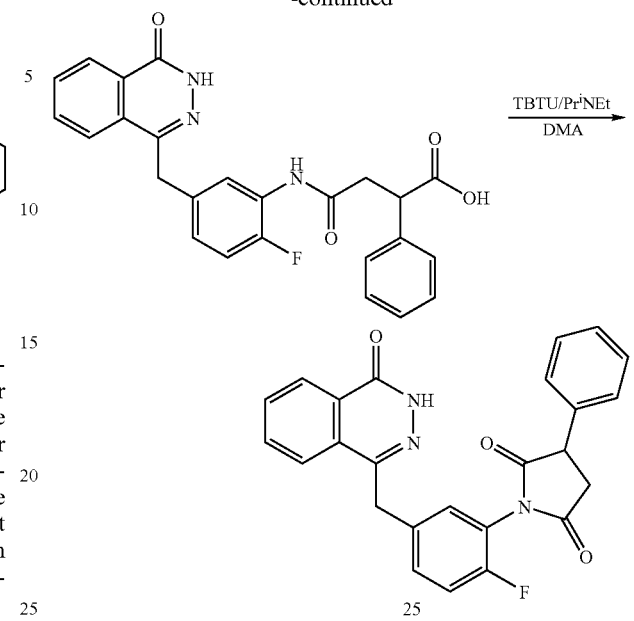

25

A stirred mixture of 4-(3-amino-4-fluorobenzyl)-2H-phthalazin-1-one (0.7 g, 2.6 mmol; prepared in a manner similar to that described in Example 23), 3-phenyldihydrofuran-2,5-dione (0.458 g, 2.6 mmol) and toluene (35 ml) was heated under reflux for 2 hours then allowed to cool to ambient temperature. The resulting solid was collected by filtration, washed with ethyl acetate (3 ml) and dried in vacuo to give N-[2-fluoro-5-(4-oxo-3,4-dihydrophthalazin-1-ylmethyl)phenyl]-2-phenylsuccinamic acid (0.775 g) as an off-white solid, m.pt. 180–183° C.; 250 MHz $^1$H-nmr (d$_6$-DMSO) δ (ppm): 2.7–2.9 (m, 1H) (—CHHCHPh—), 3.1–3.3 (m, 1H) (—CHHCHPh—), 4.0–4.1 (m, 1H) (—CHPh—) 4.3 (s, 2H) (ArCH$_2$—), 7.1–7.3 (m, 2H) (2×ArH), 7.3–7.5 (m, 5H) (5×ArH), 7.8–8.0 (m, 4H) (4×ArH), 8.3 (d, 1H) (ArH), 9.75 (s, 1H) (chain CONH), 12.5 (br s, 1H) (—CO$_2$H), 12.65 (s, 1H) (ring CONH) ; m/z (M+H)$^{+\cdot}$ 446, 100% purity.

O-Benzotriazol-1-yl-N,N,N'N'-tetramethyluronium tetrafluoroborate (0.726 g, 2.26 mmol) and diisopropylethylamine (0.494 g, 3.8 mmol) were added sequentially at ambient temperature to a stirred solution of N-[2-fluoro-5-(4-oxo-3,4-dihydrophthalazin-1-ylmethyl)phenyl]-2-phenylsuccinamic acid (0.775 g, 1.7 mmol) in dimethylacetamide (4 ml), the mixture was stirred at ambient temperature for 65 hours, then it was added dropwise to ice-cold water (40 ml). The resulting solid was collected by filtration, washed with water (3 ml), then dried in vacuo. The crude product was dissolved in hot methanol (8 ml), the solution was filtered through a small plug of cotton wool, then the filtrate was added to water (30 ml). The resulting solid was collected by filtration and dried in vacuo to give 1-[2-fluoro-5-(4-oxo-3,4-dihydrophthalazin-1-ylmethyl)phenyl]-3-phenylpyrrolidine-2,5-dione (0.555 g) as an off-white solid, m.pt. 114–120° C.; 250 MHz $^1$H-nmr (CDCl$_3$) δ (ppm): 2.8–3.0 (m, 1H) (—CHHCHPh), 3.2–3.4 (m, 1H) (—CHHCHPh), 4.1–4.3 (m, 1H+2H) (—CHPh- and ArCH$_2$—), 7.0–7.4 (m, 8H) (8×ArH), 7.6–7.8 (m, 3H) (3×ArH), 8.4 (d, 1H) (ArH), 10.65 (s, 1H) (CONH); m/z (M+H)$^{+\cdot}$ 428, 92.1% purity.

Example 26

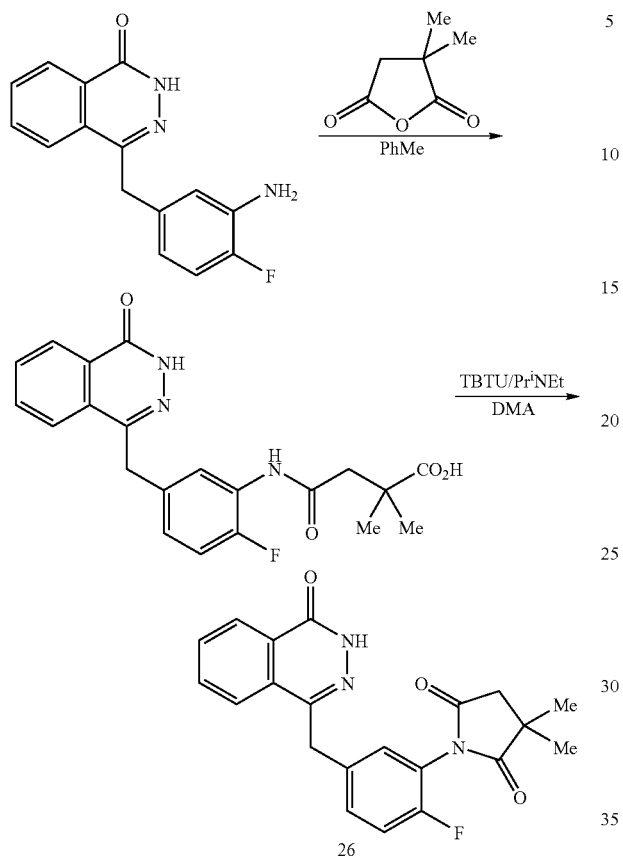

A stirred mixture of 4-(3-amino-4-fluorobenzyl)-2H-phthalazin-1-one (0.808 g, 3 mmol; prepared in a manner similar to that described in Example 23), 3,3-dimethyldihydrofuran-2,5-dione (0.384 g, 3 mmol) and toluene (50 ml) was heated under reflux for 8 hours, then the resulting solid was collected by filtration from the hot mixture, washed with toluene (20 ml) and dried in vacuo to give N-[2-fluoro-5-(4-oxo-3,4-dihydrophalazin-1-ylmethyl)phenyl]-2,2-dimethylsuccinamic acid (0.893 g) as an off-white solid, m.pt. 154–159° C.; 250 MHz $^1$H-nmr ($d_6$-DMSO) δ (ppm): 1.25 (s, 6H) (2×CH$_3$), 2.65 (s, 2H) (—CMe$_2$CH$_2$—) 4.3 (s, 2H) (ArCH$_2$—), 7.1–7.25 (m, 2H) (2×ArH), 7.8–8.0 (m, 4H) (4×ArH), 8.3 (m, 1H) (ArH), 9.65 (s, 1H) (chain CONH), 12.1 (br s, 1H) (—CO$_2$H), 12.65 (s, 1H) (ring CONH); m/z (M+H)$^+$ 398, 100% purity.

O-Benzotriazol-1-yl-N,N,N'N'-tetramethyluronium tetrafluoroborate (0.942 g, 2.9 mmol) and diisopropylethylamine (0.641 g, 5 mmol) were added sequentially at ambient temperature to a stirred solution of N-[2-fluoro-5-(4-oxo-3,4-dihydrophalazin-1-ylmethyl)phenyl]-2,2-dimethysuccinamic acid (0.896 g, 2.3 mmol) in dimethylacetamide (5 ml), the mixture was stirred at ambient temperature for 2 hours, then it was added dropwise to ice-cold water (50 ml). The resulting solid was collected by filtration, washed with water (3 ml) and dried in vacuo. The product was crystallised from industrial methylated spirit to give 1-[2-fluoro-5-(4-oxo-3,4-dihydrophalazin-1-ylmethyl) phenyl]-3,3-dimethylpyrrolidine-2,5-dione (0.4 g) as an off-white solid, m.pt. 228–231° C.; 250 MHz $^1$H-nmr ($d_6$-DMSO) δ (ppm): 1.2 (s, 6H) (2×CH$_3$), 2.7 (s, 2H) (—CMe$_2$CH$_2$—) 4.3 (s, 2H) (ArCH$_2$—), 7.25–7.35 (m, 2H) (2×ArH), 7.4–7.7.5 (m, 1H) (ArH), 7.7–7.95 (m, 3H) (3×ArH), 8.2 (m, 1H) (ArH), 12.55 (s, 1H) (CONH); m/z (M+H)$^+$ 380, 100% purity.

Example 27

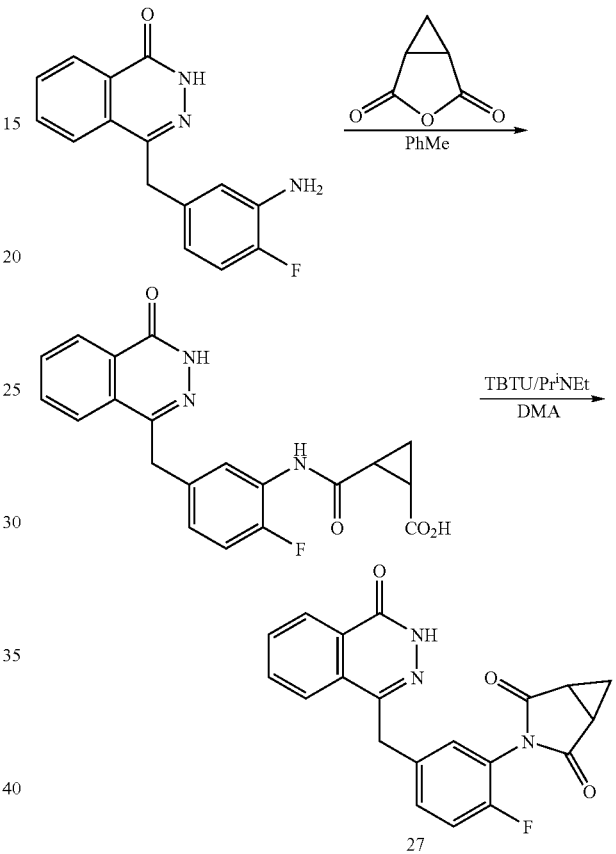

A stirred mixture of 4-(3-amino-4-fluorobenzyl)-2H-phthalazin-1-one (1 g, 3.7 mmol; prepared in a manner similar to that described in Example 23), 3-oxabicyclo[3.1.0]hexane-2,4-dione (0.416 g, 3.7 mmol) and toluene (50 ml) was heated under reflux for 1.5 hours, then the resulting solid was collected by filtration from the hot mixture, washed with ethyl acetate (3 ml) and dried in vacuo to give 2-[2-fluoro-5-(4-oxo-3,4-dihydrophalazin-1-ylmethyl)phenylcarbamoyl]cyclopropanecarboxylic acid (1.3 g) as an off-white solid, m.pt. 219–221° C.; 250 MHz $^1$H-nmr ($d_6$-DMSO) δ (ppm): 1.1–1.25 (m, 1H) (cyclopropane CH), 1.35–1.45 (m, 1H) (cyclopropane CH), 1.95–2.1 (m, 1H) (cyclopropane CH), 2.25–2.35 (m, 1H) (cyclopropane CH), 4.3 (s, 2H) (ArCH$_2$—), 7.05–7.2 (m, 2H) (2×ArH), 7.75–8.0 (m, 4H) (4×ArH), 8.25 (m, 1H) (ArH), 9.95 (s, 1H) (chain CONH), 12.15 (br s, 1H) (—CO$_2$H), 12.65 (s, 1H) (ring CONH); m/z (M+H)$^+$ 382, 100% purity.

O-Benzotriazol-1-yl-N,N,N'N'-tetramethyluronium tetrafluoroborate (1.419 g, 4.4 mmol) and diisopropylethylamine (0.965 g, 7.5 mmol) were added sequentially at ambient temperature to a stirred solution of 2-[2-fluoro-5-(4-oxo-3,4-dihydrophalazin-1-ylmethyl)phenylcarbamoyl] cyclopropanecarboxylic acid (1.3 g, 3.4 mmol) in dimethylacetamide (7 ml), the mixture was stirred at ambient temperature for 2 hours, then it was added dropwise to ice-cold water (70 ml). The resulting solid was collected by filtration, washed with water (3 ml) and dried in vacuo to give 3-[2-fluoro-5-(4-oxo-3,4-dihydrophalazin-1-ylmethyl) phenyl]-3-azabicyclo[3.1.0]hexane-2,4-dione (1.209 g) as an off-white solid, m.pt. 228–231° C.; 250 MHz $^1$H-nmr (d6-DMSO) δ (ppm): 1.4–1.55+1.9–2.05 (2×br m, 1H) (cyclopropane CH), 1.6–1.75 (m, 1H) (cyclopropane CH), 2.7–2.85 (m, 2H) (cyclopropane CH), 4.35 (s, 2H) (ArCH$_2$—), 7.25–7.35 (m, 2H) (2×ArH), 7.4–7.5 (m, 1H) (ArH), 7.75–8.0 (m, 3H) (3×ArH), 8.3 (m, 1H) (ArH), 12.65 (s, 1H) (CONH); m/z (M+H)$^{+\cdot}$ 364, 100% purity.

Example 28

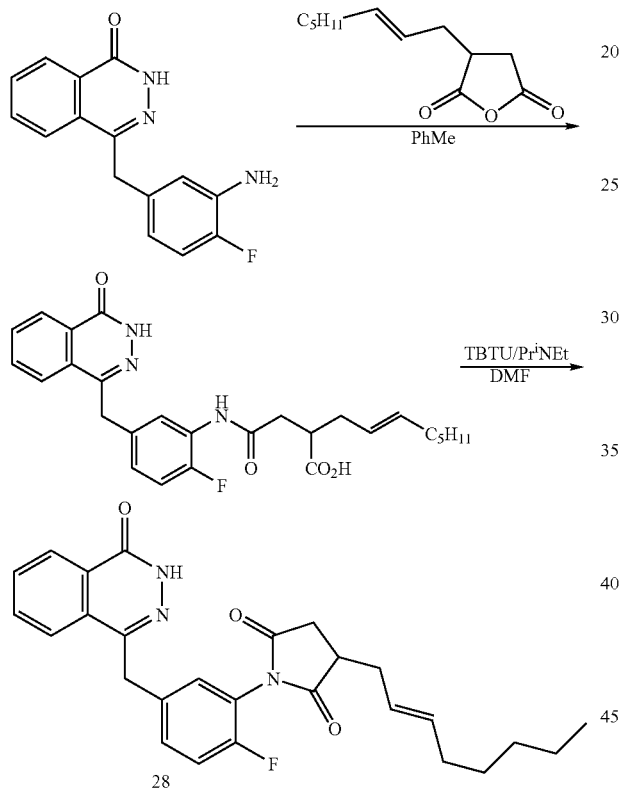

A stirred mixture of 4-(3-amino-4-fluorobenzyl)-2H-phthalazin-1-one (0.1 g, 0.37 mmol; prepared in a manner similar to that described in Example 23), 3-oct-2-enyldihydrofuran-2,5-dione (0.078 g, 0.37 mmol) and toluene (10 ml) was heated under reflux for 20 hours, then the solvent was removed in vacuo to give crude 2-{[2-fluoro-5-(4-oxo-3,4-dihydrophthalazin-1-ylmethyl)phenylcarbamoyl] methyl}dec-4-enoic acid (0.133 g) as an oil which was used without further purification.

O-Benzotriazol-1-yl-N,N,N′N′-tetramethyluronium tetrafluoroborate (0.107 g, 0.33 mmol) and diisopropylethylamine (0.098 ml, 0.56 mmol) were added sequentially at ambient temperature to a stirred solution of 2-{[2-fluoro-5-(4-oxo-3,4-dihydrophthalazin-1-ylmethyl)phenylcarbamoyl]methyl}-dec-4-enoic acid (0.123 g, 0.26 mmol) in dimethylformamide (2 ml), the mixture was stirred at ambient temperature for 48 hours, then it was added dropwise to ice-cold water (10 ml). The product was extracted into ethyl acetate (2×5 ml), the extracts were combined, dried (MgSO$_4$) and the solvent was removed in vacuo. The residue was triturated with hexane (3 ml) and the resulting solid was collected by filtration and dried in vacuo to give 1-[2-fluoro-5-(4-oxo-3,4-dihydrophthalazin-1-ylmethyl)phenyl]-3-oct-2-enylpyrrolidine-2,5-dione (0.055 g) as an off-white solid, m.pt 138–141° C.; 250 MHz $^1$H-nmr (d$_6$-DMSO) δ (ppm): 0.7–0.9 (m, 3H) (CH$_3$), 1.1–1.4 (m, 6H) (—CH$_2$CH$_2$CH$_2$CH$_3$) 1.9–2.1 (m, 2H) (—CH$_2$-$^n$Bu), 2.3–2.6 (m, 1H+2H) (—CHCH$_2$CH=CH—), 2.8–3.2 (m, 2H) (ring CH$_2$), 4.4 (s, 2H) (ArCH$_2$—), 5.25–5.45 and 5.45–5.7 (2×m, 2×1H) (—CH=CH—) 7.2–7.3 (m, 1H) (ArH), 7.3–7.5 (m, 1H) (ArH), 7.5–7.6 (m, 1H) (ArH), 7.8–8.05 (m, 3H)(3×ArH), 8.3 (d, 1H) (ArH), 12.65 (s, 1H) (CONH); m/z (M+H)$^{+\cdot}$ 462, 90% purity.

Example 29

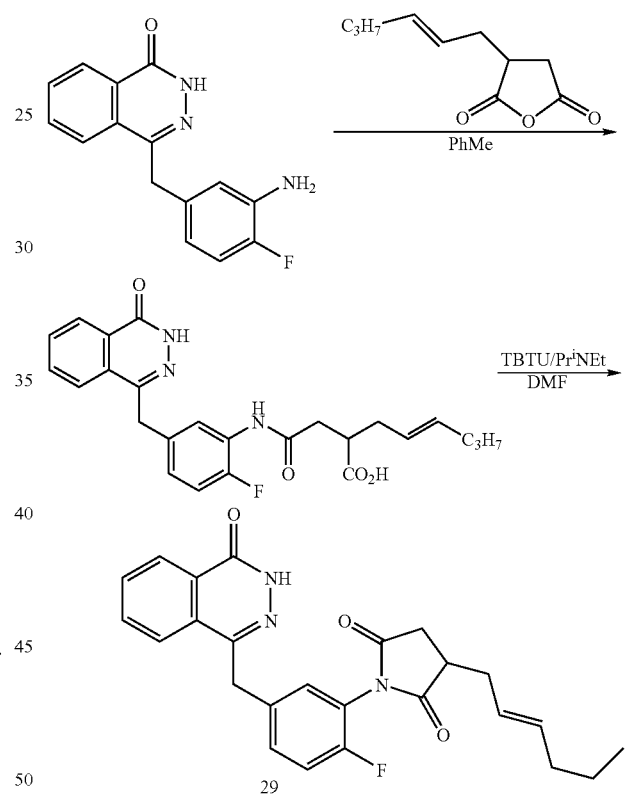

A stirred mixture of 4-(3-amino-4-fluorobenzyl)-2H-phthalazin-1-one (0.1 g, 0.37 mmol; prepared in a manner similar to that described in Example 23), 3-hex-2-enyldihydrofuran-2,5-dione (0.068 g, 0.37 mmol) and toluene (10 ml) was heated under reflux for 20 hours, then the resulting solid was collected by filtration from the hot mixture, washed with ethyl acetate (3 ml) and dried in vacuo to give 2-{[2-fluoro-5-(4-oxo-3,4-dihydrophthalazin-1-ylmethyl) phenylcarbamoyl]methyl}oct-4-enoic acid (0.061 g) as an off-white solid, m.pt. 179–181° C.; 250 MHz $^1$H-nmr (d$_6$-DMSO) δ (ppm): 0.7–0.9 (t, 3H) (CH$_3$), 1.1–1.35 (m, 2H) (—CH$_2$CH$_3$), 1.75–2.0 (m, 2H) (—CH$_2$CH$_2$CH$_3$), 2.0–2.3 (m, 2H) (—CH$_2$CH=CH—), 2.3–2.8 (2×m obscured by DMSO signal, 2H+1H) (—CH$_2$CH(CO$_2$H)CH$_2$—), 4.2 (s, 2H) (ArCH$_2$—), 5.15–5.5 (m, 2H) (—CH=CH—) 6.9–7.2

(m, 2H) (2×ArH), 7.65–8.0 (m, 4H) (4×ArH), 8.2 (d, 1H) (ArH), 12.1 (br s, 1H) (CO$_2$H), 12.6 (s, 1H) (CONH); m/z (M+H)$^{+\cdot}$ 452, 93.7% purity.

O-Benzotriazol-1-yl-N,N,N'N'-tetramethyluronium tetrafluoroborate (0.047 g, 0.15 mmol) and diisopropylethylamine (0.043 g, 0.25 mmol) were added sequentially at ambient temperature to a stirred solution 2-{[2-fluoro-5-(4-oxo-3,4-dihydrophthalazin-1-ylmethyl)phenylcarbamoyl]methyl}oct-4-enoic acid (0.051 g, 0.11 mmol) in dimethylformamide (2 ml), the mixture was stirred at ambient temperature for 48 hours, then it was added dropwise to ice-cold water (10 ml). The resulting solid was collected by filtration and dried in vacuo to give 1-[2-fluoro-5-(4-oxo-3,4-dihydrophthalazin-1-ylmethyl)phenyl]-3-hex-2-enylpyrrolidine-2,5-dione (0.029 g) as an off-white solid, m.pt. 146–149° C.; 250 MHz $^1$H-nmr (d$_6$-DMSO) δ (ppm): 0.8–1.0 (m, 3H) (CH$_3$), 1.2–1.4 (m, 2H) (—CH$_2$CH$_3$), 1.9–2.1 (m, 2H) (—CH$_2$CH$_2$CH$_3$), 2.3–2.5 (m, 2H) (—CH$_2$CH═CH—), 2.5–2.6 (m, 1H) (ring CH), 2.8–3.0 and 3.0–3.2 (2×m, 2H) (ring CH$_2$), 4.4 (s, 2H) (ArCH$_2$—), 5.25–5.45 and 5.45–5.7 (2×m, 2×1H) (—CH═CH—) 7.2–7.3 (m, 1H) (ArH), 7.3–7.5 (m, 1H) (ArH), 7.5–7.6 (m, 1H) (ArH), 7.8–8.05 (m, 3H) (3×ArH), 8.3 (d, 1H) (ArH), 12.65 (s, 1H) (CONH); m/z (M+H)$^{+\cdot}$ 434, 95.8% purity.

Example 30

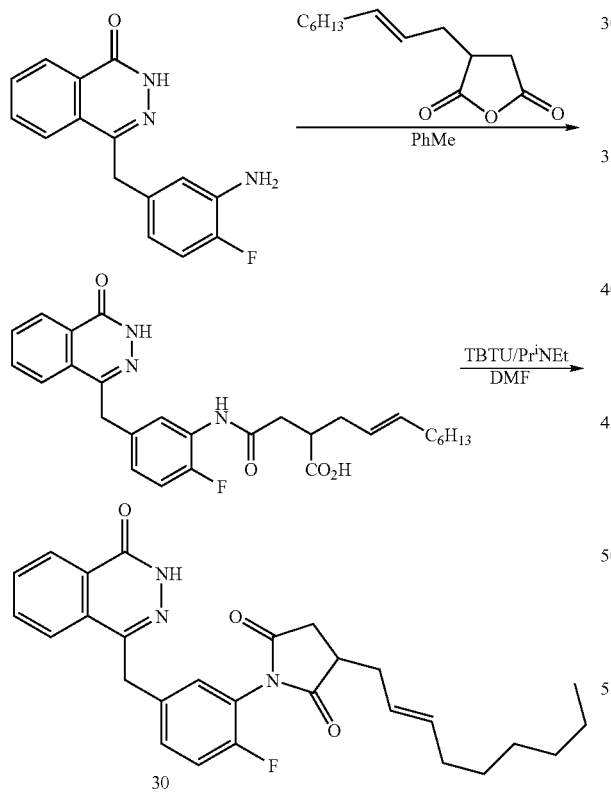

1-[2-Fluoro-5-(4-oxo-3,4-dihydrophthalazin-1-ylmethyl)phenyl]-3-non-2-enylpyrrolidine-2,5-dione (0.041 g) was synthesised in a manner similar to that described in Example 28. It was isolated as an off-white solid, m.pt. 146–149° C.; 250 MHz $^1$H-nmr (d$_6$-DMSO) δ (ppm): 0.7–0.9 (m, 3H) (CH$_3$), 1.1–1.4 (m, 8H) (CH$_2$CH$_2$CH$_2$CH$_2$CH$_3$), 1.9–2.1 (m, 2) (—CH$_2$-"Pentyl), 2.3–2.5 (m, 2H) (—CH$_2$CH═CH—), 2.5–2.6 (m, 1H) (ring CH), 2.8–3.0 and 3.0–3.2 (2×m, 2H) (ring CH$_2$), 4.4 (s, 2H) (ArCH$_2$—), 5.25–5.45 and 5.45–5.7 (2×m, 2×1H) (—CH═CH—) 7.2–7.3 (m, 1H) (ArH), 7.3–7.5 (m, 1H) (ArH), 7.5–7.6 (m, 1H) (ArH), 7.8–8.05 (m, 3H) (3×ArH), 8.3 (d, 1H) (ArH), 12.65 (s, 1H) (CONH).

Example 31

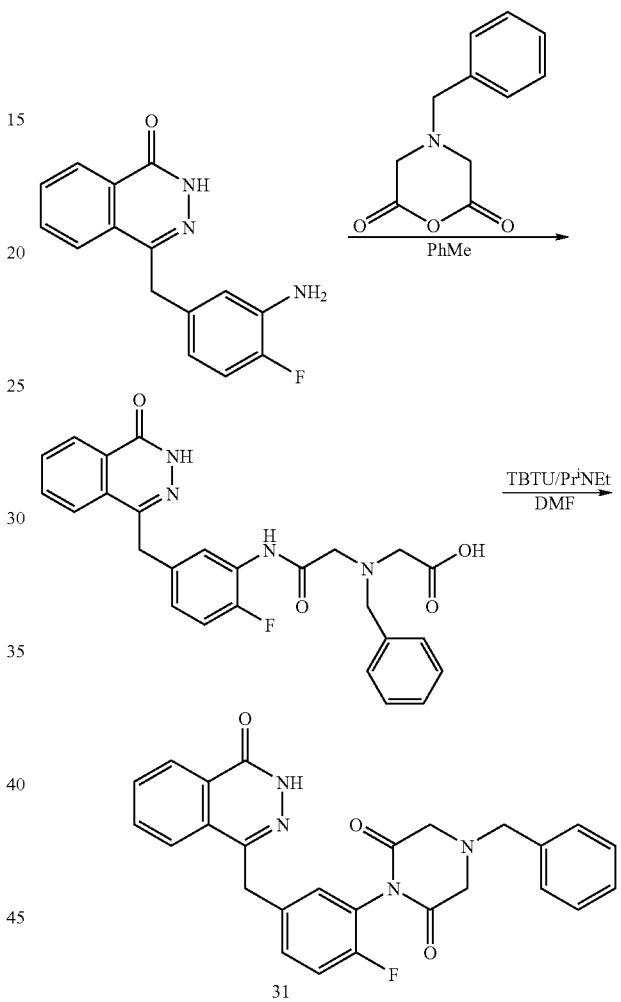

A stirred mixture of 4-(3-amino-4-fluorobenzyl)-2H-phthalazin-1-one (2.51 g, 9.3 mmol; prepared in a manner similar to that described in Example 23), 4-benzylmorpholin-2,6-dione (2.3 g, 11.2 mmol) and toluene (15 ml) was heated under reflux for 20 hours, then the solvent was removed in vacuo. The residue was dissolved in dimethylacetamide (15 ml) and O-benzotriazol-1-yl-N,N,N'N'-tetramethyluronium tetrafluoroborate (3 g, 9.3 mmol) and diisopropylethylamine (1.63 ml, 9.3 mmol) were added sequentially. The mixture was stirred at ambient temperature for 2 hours, then it was added dropwise to stirred, ice-cold water (300 ml). The resulting solid was collected by filtration and dried in vacuo to give 4-benzyl-1-[2-fluoro-5-(4-oxo-3,4-dihydrophthalazin-1-ylmethyl)phenyl]piperazine-2,6-dione (4.01 g) as an off-white solid, 250 MHz $^1$H-nmr (d$_6$-DMSO) δ (ppm): 3.6 (s, 4H) (2×ring CH$_2$) 3.75 (s, 2H) (NCH$_2$Ph), 4.35 (s, 2H) (ArCH$_2$—), 7.17–7.5 (m, 8H)

(8×ArH), 7.75–8.0 (m, 3H) (3×ArH), 8.25 (d, 1H) (ArH), 12.6 (s, 1H) (CONH); m/z (M+H)+ 457, 100% purity.

Example 32

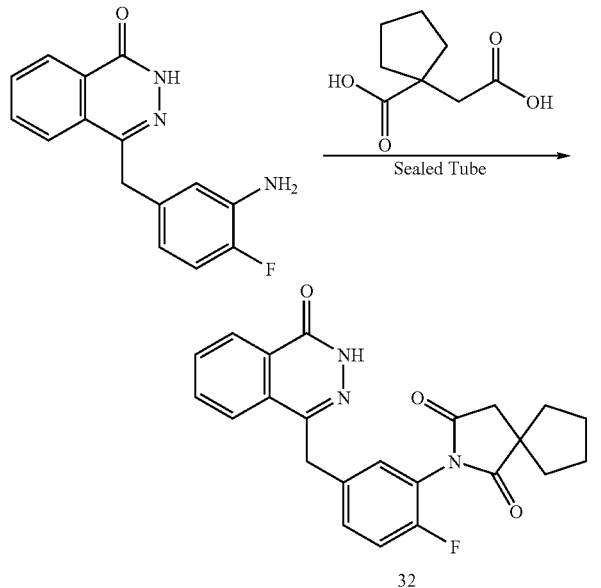

32

A stirred mixture of 4-(3-amino-4-fluorobenzyl)-2H-phthalazin-1-one (0.1 g, 0.37 mmol; prepared in a manner similar to that described in Example 23) and 1-(carboxymethyl)cyclopentane-1-carboxylic acid (0.064 g, 0.37 mmol) was heated at 200° C. in a sealed tube until the starting materials had been consumed (the reaction was followed by tlc using a 1:1 mixture of ethyl acetate and hexane as eluant). The warm mixture was poured into an ice/water mixture (10 ml) and the resulting solid was collected by filtration. The crude product was recrystallised from ethyl acetate/hexane (the hot solution required filtration to remove traces of undissolved solids) to give 2-[2-fluoro-5-(4-oxo-3,4-dihydrophthalazin-1-ylmethyl)phenyl]-2-azaspiro[4.4]nonane-1,3-dione (0.03 g) as an off-white solid, m.pt. 215–220° C.; 250 MHz $^1$H-nmr (d$_6$-DMSO) δ (ppm): 1.7–2.2 (m, 8H) (4× cyclopentyl CH$_2$), 2.9 (s, 2H) (—COCH$_2$—), 4.35 (s, 2H) (ArCH$_2$—), 7.3–7.45 (m, 2H) (2×ArH), 7.5–7.6 (m, 1H) (ArH), 7.8–8.1 (m, 3H) (3×ArH), 8.3 (d, 1H) (ArH), 12.7 (s, 1H) (CONH); m/z (M+H)+ 406, 91.4% purity.

Example 33

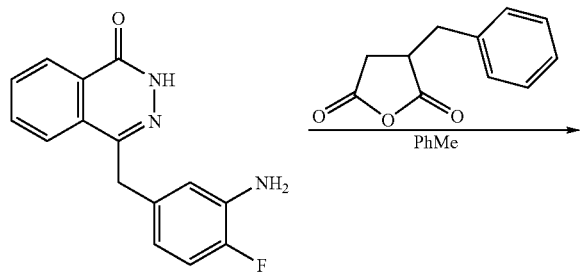

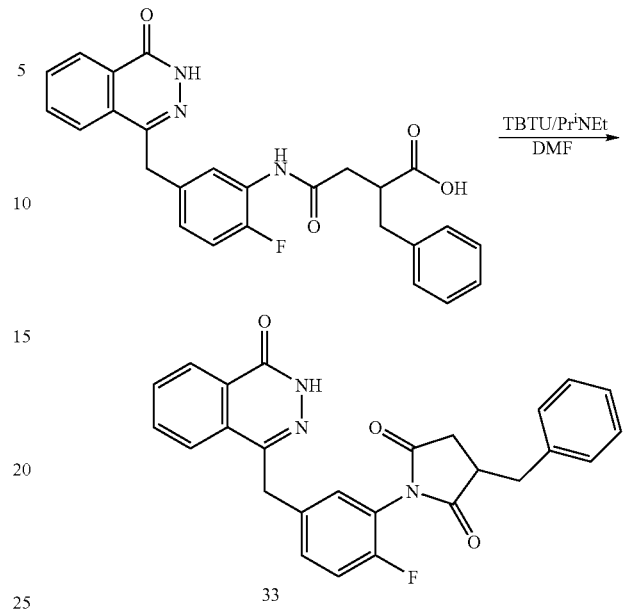

33

A stirred mixture of 4-(3-amino-4-fluorobenzyl)-2H-phthalazin-1-one (0.135 g, 0.5 mmol; prepared in a manner similar to that described in Example 23), 3-benzyldihydrofuran-2,5-dione (0.095 g, 0.5 mmol) and toluene (8 ml) was heated under reflux for 1 hour, allowed to stand at ambient overnight, then heated under reflux for a further 6.5 hours and allowed to cool to ambient temperature. The resulting solid was collected by filtration, washed with hexane (10 ml) and dried in vacuo to give 2-benzyl-N-[2-fluoro-5-(4-oxo-3,4-dihydrophthalazin-1-ylmethyl)phenyl]succinamic acid (0.156 g) as an off white solid, 250 MHz $^1$H-nmr (d$_6$-DMSO) δ (ppm): 2.2–2.95 (m 5H) (—CH$_2$CH(CO$_2$H) CH$_2$Ph), 4.2 (s, 2H) (ArCH$_2$—), 6.9–7.25 (m, 7H) (7×ArH), 7.6–7.9 (m, 4H) (4×ArH), 8.15 (d, 1H) (ArH), 9.65 (s, 1H) (chain CONH), 12.2 (s, 1H) (—CO$_2$H), 12.5 (s, 1H) (ring CONH).

O-Benzotriazol-1-yl-N,N,N'N'-tetramethyluronium tetrafluoroborate (0.14 g, 0.44 mmol) and diisopropylethylamine (0.097 g, 0.44 mmol) were added sequentially at ambient temperature to a stirred solution of 2-benzyl-N-[2-fluoro-5-(4-oxo-3,4-dihydrophthalazin-1-ylmethyl)phenyl] succinamic acid (0.156 g, 0.34 mmol) in dimethylformamide (2 ml), the mixture was stirred at ambient temperature for 3 hours, then it was added dropwise to ice-cold water (10 ml). The mixture was stirred for 30 minutes, then the resulting solid was collected by filtration, washed with water (5 ml) and dried in vacuo to give 3-benzyl-1-[2-fluoro-5-(4-oxo-3,4-dihydrophthalazin-1-ylmethyl)phenyl]pyrrolidine-2,5-dione (0.120 g) as a white solid, 250 MHz $^1$H-nmr (d$_6$-DMSO) δ (ppm): 2.6–3.4 (m 5H) (—CH$_2$CH(CO$_2$H) CH$_2$Ph), 4.5 (s, 2H) (ArCH$_2$—), 7.3–7.6 (m, 7H) (7×ArH), 7.6–7.7 (m, 1H) (ArH), 7.9–8.2 (m, 3H) (3×ArH), 8.4 (m, 1H) (ArH), 12.8 (br s, 1H) (CONH); m/z (M+H)+ 442, 96.8% purity.

Example 34

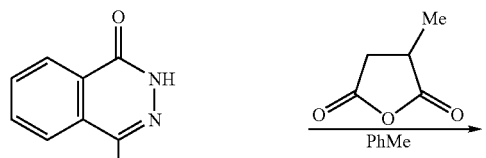

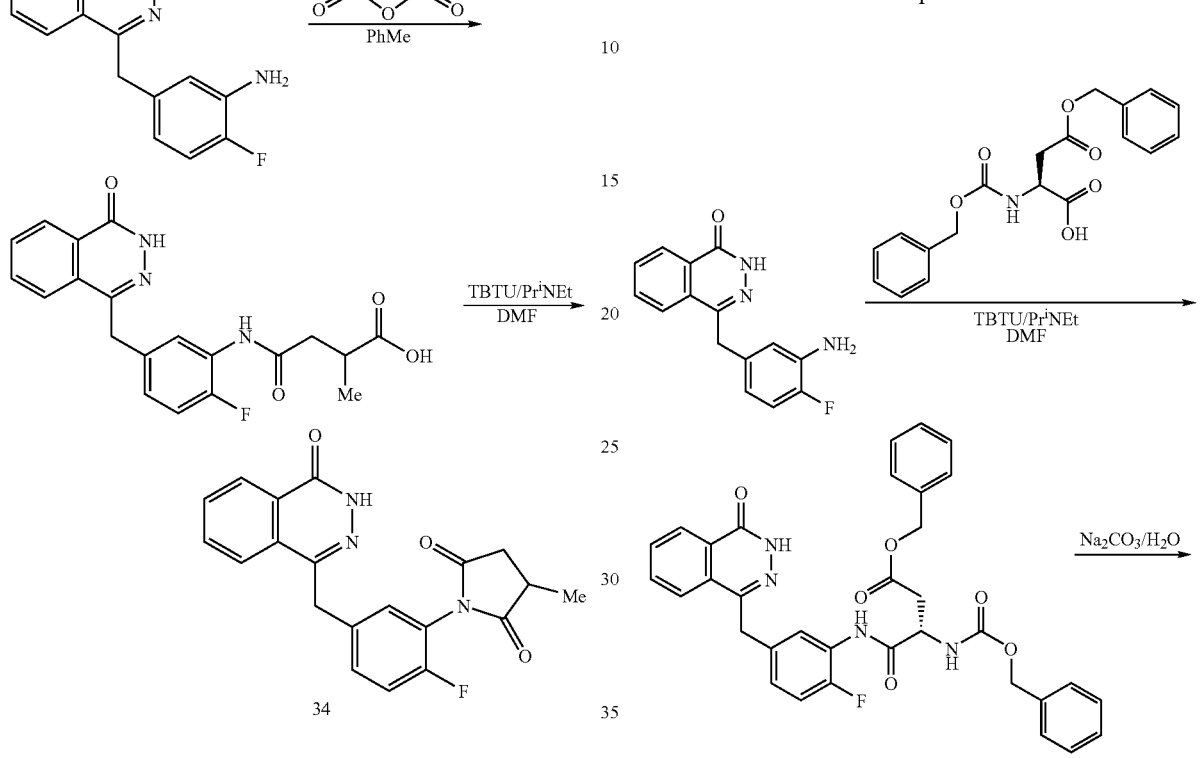

A stirred mixture of 4-(3-amino-4-fluorobenzyl)-2H-phthalazin-1-one (2.02 g, 7.5 mmol; prepared in a manner similar to that described in Example 23), 3-methyldihydrofuran-2,5-dione (0.856 g, 7.5 mmol) and toluene (100 ml) was heated under reflux for 2.5 hours (for the first 30 minutes of this period, traces of water in the mixture were removed by azeotropic distillation). The resulting solid was collected by filtration from the hot mixture, washed with toluene (20 ml) and dried in vacuo to give N-[2-fluoro-5-(4-oxo-3,4-dihydrophthalazin-1-ylmethyl)phenyl]-2-methylsuccinamic acid (1.91 g) as an off-white solid, m.pt. 140–144° C.; 250 MHz $^1$H-nmr ($d_6$-DMSO) δ (ppm): 0.95 (d, 3H) (CH$_3$), 2.2–2.6 (m, 3H) (—CH$_2$CHMe-), 4.1 (s, 2H) (ArCH$_2$—), 6.9–7.2 (m, 2H) (2×ArH), 7.6–7.9 (m, 4H) (4×ArH), 8.1 (d, 1H) (ArH), 9.55 (s, 1H) (chain CONH), 12.0 (br s, 1H) (CO$_2$H), 12.5 (s, 1H) (ring CONH); m/z (M+H)$^+$ 384, 100% purity.

O-Benzotriazol-1-yl-N,N,N'N'-tetramethyluronium tetrafluoroborate (1.09 g, 3.4 mmol) and diisopropylethylamine (0.98 g, 5.7 mmol) were added sequentially to a stirred solution of N-[2-fluoro-5-(4-oxo-3,4-dihydrophthalazin-1-ylmethyl)phenyl]-2-methylsuccinamic acid (1 g, 2.6 mmol) in dimethylacetamide (5 ml), the mixture was stirred at ambient temperature for 15 minutes, then it was poured onto water (50 ml) and allowed to stand at ambient temperature for 20 hours. The resulting solid was collected by filtration, washed with hexane (20 ml) and dried in vacuo to give 1-[2-fluoro-5-(4-oxo-3,4-dihydrophthalazin-1-ylmethyl)phenyl]-3-methylpyrrolidine-2,5-dione (0.654 g) as a beige solid, m.pt. 171–172° C.; 250 MHz $^1$H-nmr ($d_6$-DMSO) δ (ppm): 1.4 (d, 3H) (CH$_3$), 2.6–2.7 (m, obscured by DMSO signal, 1H) (—CHMe-), 3.05–3.3 (m, 2H) (—CH$_2$CHMe-), 4.5 (s, 2H) (ArCH$_2$—), 7.3–7.55 (m, 2H) (2×ArH), 7.6–7.7 (m, 1H) (ArH), 7.9–8.2 (m, 3H) (3×ArH), 8.4 (d, 1H) (ArH), 12.8 (s, 1H) (CONH); m/z (M+H)$^+$ 366, 98% purity.

Example 35

O-Benzotriazol-1-yl-N,N,N'N'-tetramethyluronium tetrafluoroborate (0.417 g, 1.3 mmol), diisopropylethylamine (0.284 g, 2.2 mmol) and 4-(3-amino-4-fluorobenzyl)-2H-phthalazin-1-one (0.269 g, 1 mmol; prepared in a manner similar to that described in Example 23) were added sequentially to a stirred solution of N-α-CBZ-L-aspartic acid β-benzyl ester (0.357 g, 1 mmol) in dimethylformamide (2 ml), the mixture was stirred at ambient temperature for 50 hours, then it was poured into ice-cold water (20 ml). The resulting solid was collected by filtration and dried in vacuo to give (S)-3-benzyloxycarbonylamino-N-[2-fluoro-5-(4-oxo-3,4-dihydrophthalazin-1-ylmethyl)phenyl]succinamic acid benzyl ester (0.57 g) as a beige solid, m.pt. 76–80° C.; m/z (M+H)⁺ 607, 82% purity, which was used without further purification.

A mixture of the above crude (S)-3-benzyloxycarbonylamino-N-[2-fluoro-5-(4-oxo-3,4-dihydrophthalazin-1-ylmethyl)phenyl]succinamic acid benzyl ester (0.57 g) and saturated aqueous sodium carbonate solution (pH 9; 10 ml) was stirred at ambient temperature for 72 hours. The pH of the mixture was adjusted to pH10 by the addition of further saturated aqueous sodium carbonate solution, then the mixture was stirred at 70° C. for 4 hours until a clear solution was obtained. The cooled solution was washed with ethyl acetate (2×5 ml) and the aqueous layer was acidified by the addition of 10% hydrochloric acid. The resulting solid was collected by filtration and dried in vacuo to give (S)-3-benzyloxycarbonylamino-N-[2-fluoro-5-(4-oxo-3,4-dihydrophthalazin-1-ylmethyl)phenyl]succinamic acid (0.35 g) as an off-white solid, m.pt. 188–190° C., which was used without further purification.

O-Benzotriazol-1-yl-N,N,N'N'-tetramethyluronium tetrafluoroborate (0.289 g, 0.9 mmol) and diisopropylethylamine (0.193 g, 1.5 mmol) were added sequentially to a stirred solution of (S)-3-benzyloxycarbonylamino-N-[2-fluoro-5-(4-oxo-3,4-dihydrophthalazin-1-ylmethyl)phenyl]succinamic acid (0.35 g, 0.68 mmol) in dimethylacetamide (3 ml), the mixture was stirred at ambient temperature for 24 hours, then it was added dropwise to stirred, ice-cold water (30 ml). The mixture was stirred for 1 hour, then the resulting solid was collected by filtration and dried in vacuo to give (S)-3-benzyloxycarbonylamino-1-[2-fluoro-5-(4-oxo-3,4-dihydrophthalazin-1-ylmethyl)phenyl]pyrrolidine-2,5-dione (0.238 g) as an off white solid, m.pt. 121–127° C. (softens 102° C.); m/z (M+H)⁺ 501, 96% purity.

Example 36

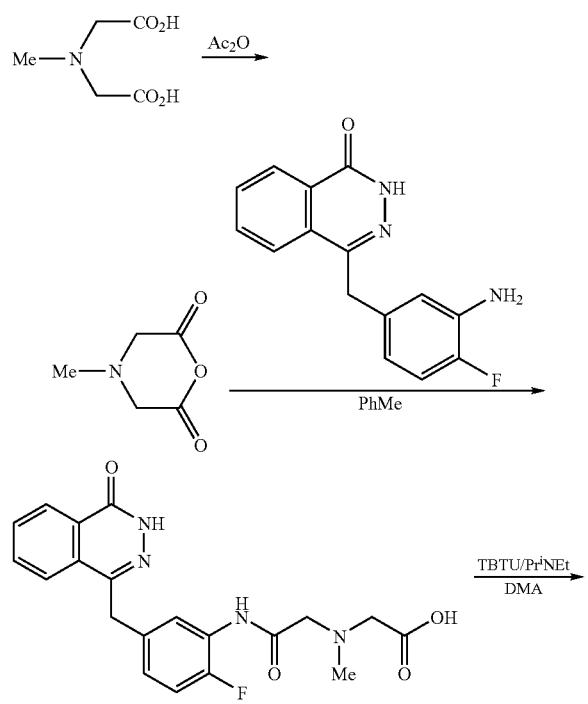

-continued

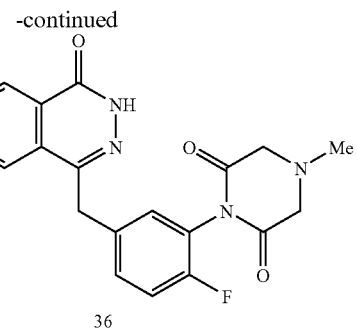

36

A stirred mixture of N-methyliminodiacetic acid (0.06 g, 0.4 mmol) and acetic anhydride (1 ml) was heated under reflux under nitrogen for 20 minutes, until a clear solution was obtained. The excess of acetic anhydride and the acetic acid produced in the reaction were removed in vacuo and the residual 4-methylmorpholine-2,6-dione was dissolved in toluene (7 ml) and used without purification.

4-(3-Amino-4-fluorobenzyl)-2H-phthalazin-1-one (0.108 g, 0.4 mmol; prepared in a manner similar to that described in Example 23) was added to the above toluene solution, the stirred mixture was heated under reflux for 2 hours and allowed to stand at ambient temperature for 20 hours, then the resulting solid was collected by filtration and dried in vacuo to give N-[2-fluoro-5-(4-oxo-3,4-dihydrophthalazin-1-ylmethyl)phenylcarbamoylmethyl]-N-methylglycine (0.125 g) as a beige solid, m.pt. 194–198° C.; m/z (M+H)⁺ 399, 92.6% purity, which was used without further purification.

O-Benzotriazol-1-yl-N,N,N'N'-tetramethyluronium tetrafluoroborate (0.108 g, 0.34 mmol) and diisopropylethylamine (0.074 g, 0.57 mmol) were added sequentially at ambient temperature to a stirred solution of N-[2-fluoro-5-(4-oxo-3,4-dihydrophthalazin-1-ylmethyl)phenylcarbamoylmethyl]-N-methylglycine (0.103 g, 0.26 mmol) in dimethylacetamide (1 ml), the mixture was stirred at ambient temperature for 1 hour, then it was diluted with water (10 ml). Sodium chloride (1 g) was added, the mixture was stirred at ambient temperature for 30 minutes, then the resulting solid was collected by filtration, washed with water (1 ml) and dried in vacuo to give 1-[2-fluoro-5-(4-oxo-3,4-dihydrophthalazin-1-ylmethyl)phenyl]-4-methylpiperazine-2,6-dione (0.071 g) as a beige solid, m.pt. 205–208° C.; 250 MHz ¹H-nmr (CDCl₃) δ (ppm): 2.4 (s, 3H) (CH₃), 3.5 (q, 4H) (2×CH₂), 4.25 (s, 2H) (ArCH₂—), 7.1 (m, 2H) (2×ArH), 7.25 (m, 1H) (ArH), 7.7–7.85 (m, 3H) (3×ArH), 8.4 (m, 1H) (ArH), 10.35 (s, 1H) (CONH); m/z (M+H)⁺ 381, 100% purity.

Example 37

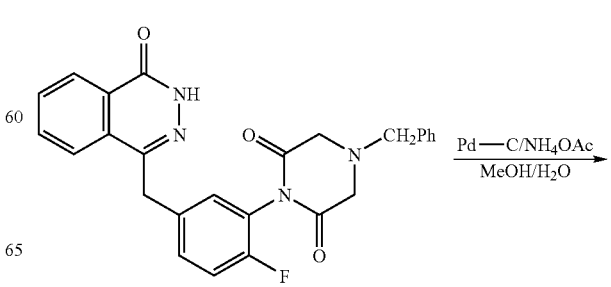

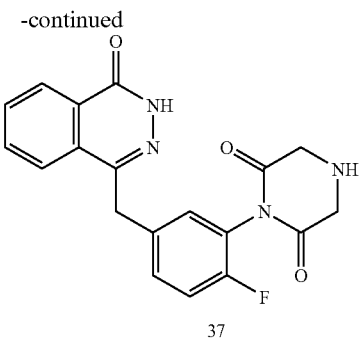

A solution of ammonium formate (0.55 g, 8.8 mmol) in water (5 ml) was added to a stirred mixture of 4-benzyl-1-[2-fluoro-5-(4-oxo-3,4-dihydrophthalazin-1-ylmethyl)phenyl]piperazine-2,6-dione (1 g, 2.2 mmol; prepared in a manner similar to that described in Example 31), 10% palladium on carbon catalyst (0.33 g) and methanol (15 ml), the mixture was heated under reflux for 1 hour, then it was cooled to ambient temperature and filtered through a pad of Celite filter aid. The filter pad was washed with methanol (50 ml), then the combined filtrate and washings were concentrated in vacuo. The residue was diluted with water (20 ml), the product was extracted into ethyl acetate (4×20 ml), the combined extracts were dried (MgSO$_4$) and the solvent was removed in vacuo to give 1-[2-fluoro-5-(4-oxo-3,4-dihydrophthalazin-1-ylmethyl)phenyl]piperazine-2,6-dione (0.8 g) as a pale brown solid, 250 MHz $^1$H-nmr (d$_6$-DMSO) δ (ppm): 3.3 (2× overlapping d, 4H) (2×ring CH$_2$), 4.25 (s, 2H) (ArCH$_2$—), 6.95–7.2 (m, 2H) (2×ArH), 7.7–7.9 (m, 3H) (3×ArH), 7.95 (d, 1H) (ArH), 8.2 (d, 1H) (ArH), 9.7 (s, 1H) (piperazine NH), 12.6 (s, 1H) (CONH).

Example 38

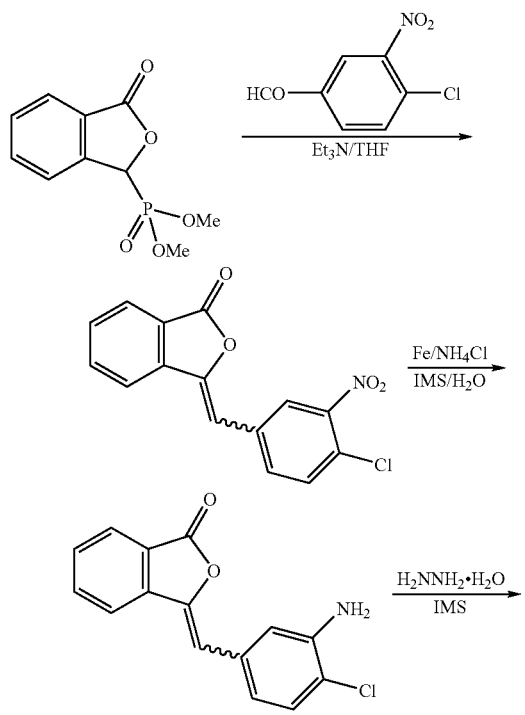

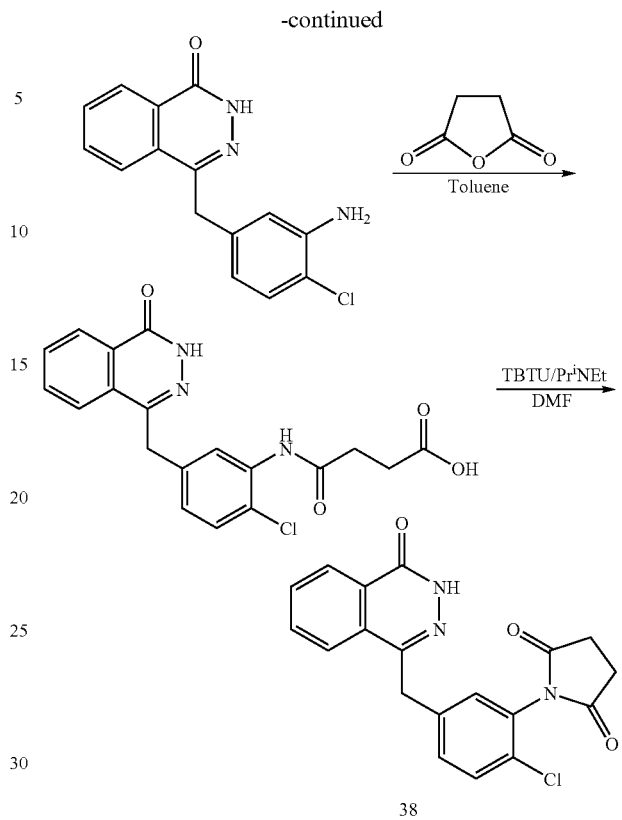

A stirred solution of dimethyl 3-oxo-1,3-dihydroisobenzofuran-1-ylphosphonate (4.84 g, 0.02 mol; prepared in a manner similar to that described in Example 23) and 4-chloro-3-nitrobenzaldehyde (3.71 g, 0.02 mol) in tetrahydrofuran (30 ml) was cooled to 15° C. and a solution of triethylamine (2.02 g, 0.02 mol) in tetrahydrofuran (3 ml) was added dropwise at <25° C. The mixture was stirred at ambient temperature for 1 hour, allowed to stand at this temperature for a further 16 hours and the resulting solid was collected by filtration. The filtrate was concentrated in vacuo, the residue was triturated with water (5 ml) and the resulting solid was collected by filtration. The two crops of solid were combined and suspended in water (30 ml). The mixture was stirred at ambient temperature for 30 minutes and the resulting solid was collected by filtration and dried in vacuo for 24 hours to give crude 3-(4-chloro-3-nitrobenzylidene)-3H-isobenzofuran-1-one as a pale yellow solid, m.pt. 198–204° C., still slightly wet with water, which was used directly in the next stage.

A stirred mixture of the above crude 3-(4-chloro-3-nitrobenzylidene)-3H-isobenzofuran-1-one (6.2 g), industrial methylated spirit (80 ml), water (60 ml) and ammonium chloride (2.14 g, 0.04 mol) was heated to 70° C., and iron powder (11.2 g, 0.2 gatom) was added in portions. When the addition was complete, the stirred mixture was heated under reflux for a further 2 hours, then it was filtered while hot through Celite. The collected inorganic solids were washed with hot industrial methylated spirit (3×150 ml), then the filtrate and washings were combined and the solvent was removed in vacuo. The residue was triturated with water (60 ml) and the resulting sticky solid was collected by filtration and triturated with industrial methylated spirit (80 ml). The resulting solid was collected by filtration, washed with industrial methylated spirit (2×1 ml) and dried in vacuo for 24 hours to give 3-(3-amino-4-chlorobenzylidene)-3H-isobenzofuran-1-one (3.58 g) as a yellow solid, m.pt.

148–153° C.; m/z (M+H)⁺ 272/274, 100% purity, which was used directly in the next stage.

A stirred mixture of the above 3-(3-amino-4-chlorobenzylidene)-3H-isobenzofuran-1-one (0.815 g, 3 mmol), industrial methylated spirit (10 ml) and hydrazine monohydrate (0.15 g, 3 mmol) was heated under reflux for 1 hour then cooled to ambient temperature. The resulting solid was collected by filtration, washed with industrial methylated spirit (5 ml) and water (5 ml), and dried in vacuo to give a pale grey solid. The crude material was recrystallised from acetonitrile (140 ml) and the resulting solid was collected by filtration and dried in vacuo to give 4-(3-amino-4-chlorobenzyl)-2H-phthalazin-1-one (0.607 g) as an off-white solid, m.pt. 227–228° C.; 250 MHz ¹H-nmr (d₆-DMSO) δ (ppm): 4.05 (s, 2H) (ArCH₂—), 5.2 (s, 2H) (—NH₂), 6.4–6.5 (m, 1H) (ArH), 6.6–6.7 (m, 1H) (ArH), 6.95–7.05 (m, 1H) (ArH), 7.65–7.85 (m, 3H) (3×ArH), 8.1–8.2 (m, 1H) (ArH), 12.5 (s, 1H) (CONH) ; m/z (M+H)⁺ 286/288, 100% purity.

A stirred mixture of 4-(3-amino-4-chlorobenzyl)-2H-phthalazin-1-one (0.171 g, 0.6 mmol), succinic anhydride (0.06 g, 0.6 mmol) and toluene (60 ml) was heated under reflux for 2 hours, then cooled to ambient temperature. The precipitated solid was collected by filtration and recrystallised from industrial methylated spirit (20 ml). The resulting solid was collected by filtration and dried in vacuo to give N-[2-chloro-5-(4-oxo-3,4-dihydrophalazin-1-ylmethyl)phenyl]succinamic acid (0.149 g) as an off-white solid, m.pt. 215–217° C.; m/z (M+H)⁺ not detected, 100% purity. This material was used without further purification.

O-Benzotriazol-1-yl-N,N,N'N'-tetramethyluronium tetrafluoroborate (0.150 g, 0.47 mmol) and diisopropylethylamine (0.102 g, 0.8 mmol) were added sequentially at ambient temperature to a stirred solution of N-[2-chloro-5-(4-oxo-3,4-dihydrophalazin-1-ylmethyl)phenyl]succinamic acid (0.139 g, 0.36 mmol) in dimethylformamide (2 ml), and the mixture was stirred at ambient temperature for 20 hours. Tlc indicated that starting material remained, so the stirred mixture was heated to 100° C. for 1 hour then allowed to cool to ambient temperature. The resulting mixture was added dropwise to water (20 ml), the mixture was stirred at ambient temperature for 1 hour, and the resulting solid was collected by filtration, triturated with a mixture of industrial methylated spirit (1 ml) and ethyl acetate (2 ml), collected by filtration and dried in vacuo to give 1-[2-chloro-5-(4-oxo-3,4-dihydrophalazin-1-ylmethyl)phenyl]pyrrolidine-2,5-dione (0.07 g) as an off-white solid, m.pt. 260–263° C.; 250 MHz ¹H-nmr (d₆-DMSO) δ (ppm): 2.75–2.95 (m, 4H) (—CH₂CH₂—) 4.4 (s, 2H) (ArCH₂—), 7.3 (s, 1H) (ArH), 7.5–7.65 (m, 2H) (2×ArH), 7.8–8.05 (m, 3H) (3×ArH), 8.3 (d, 1H) (ArH), 12.65 (s, 1H) (CONH); m/z (M+H)⁺ 368/370, 93.1% purity.

The following Examples 39–42 were synthesised in a manner analogous to the final two stages described in Example 38, using appropriate starting materials, and following both reaction stages by tlc until starting materials were consumed. Any substantial variations in methodology are noted below.

Example 39

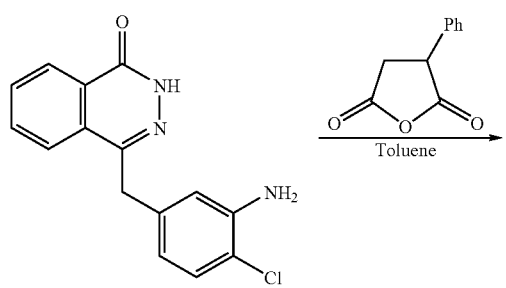

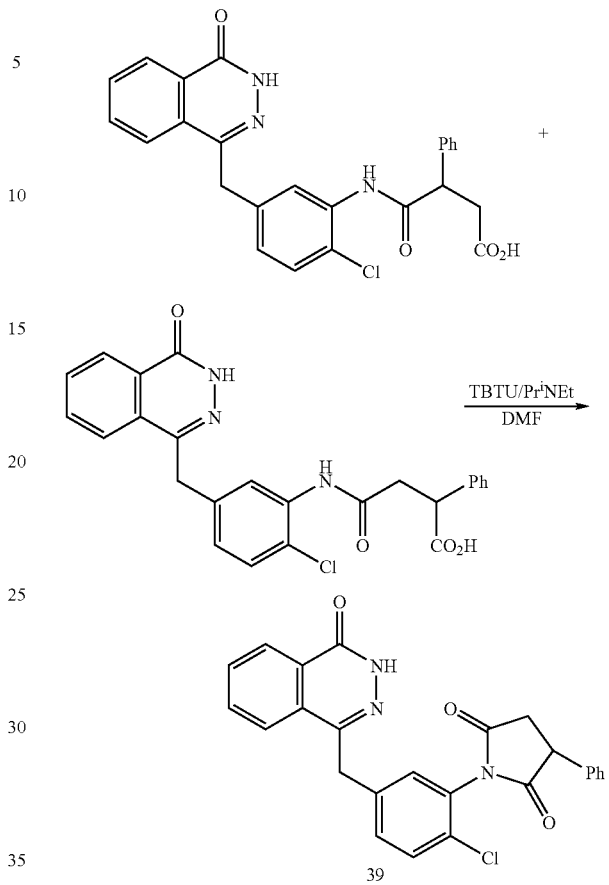

The open chain intermediate was a mixture of N-[2-chloro-5-(4-oxo-3,4-dihydrophalazin-1-ylmethyl)phenyl]-2-phenylsuccinamic acid and N-[2-chloro-5-(4-oxo-3,4-dihydrophalazin-1-ylmethyl)phenyl]-3-phenylsuccinamic acid, obtained as an off-white solid, m.pt. 195–197° C.

The cyclisation reaction mixture was stirred for 2 hours at ambient temperature, then allowed to stand for a further 16 hours before work-up, without further heating, to give 1-[2-chloro-5-(4-oxo-3,4-dihydrophalazin-1-ylmethyl)phenyl]-3-phenylpyrrolidine-2,5-dione (0.073 g) as a white powder, m.pt. 131–135° C.; m/z (M+H)⁺ 444/446, 91.3% purity.

Example 40

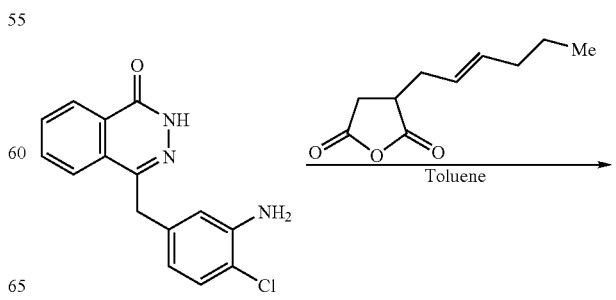

Example 41

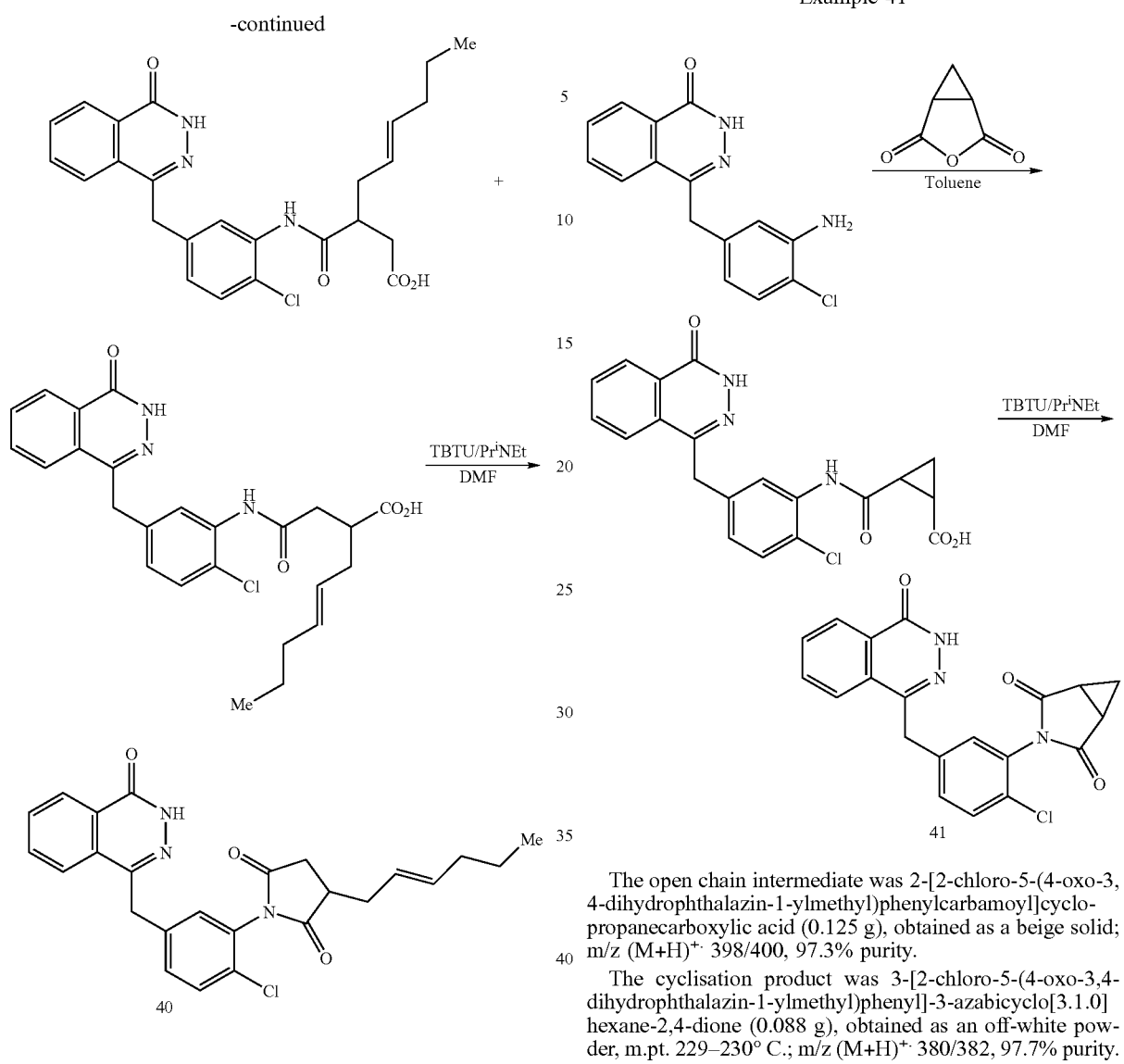

The open chain intermediate was 2-[2-chloro-5-(4-oxo-3,4-dihydrophthalazin-1-ylmethyl)phenylcarbamoyl]cyclopropanecarboxylic acid (0.125 g), obtained as a beige solid; m/z (M+H)$^+$ 398/400, 97.3% purity.

The cyclisation product was 3-[2-chloro-5-(4-oxo-3,4-dihydrophthalazin-1-ylmethyl)phenyl]-3-azabicyclo[3.1.0]hexane-2,4-dione (0.088 g), obtained as an off-white powder, m.pt. 229–230° C.; m/z (M+H)$^+$ 380/382, 97.7% purity.

The open chain intermediate required purification by suspension in 0.75 M aqueous sodium hydrogencarbonate solution (20 ml) and washing with dichloromethane (2×10 ml). The aqueous layer was reacidified by the addition of 5 M hydrochloric acid and the resulting solid was collected by filtration and dried in vacuo to give a mixture of N-[2-chloro-5-(4-oxo-3,4-dihydrophalazin-1-ylmethyl)phenyl]-2-hexen-2-ylsuccinamic acid and N-[2-chloro-5-(4-oxo-3,4-dihydrophalazin-1-ylmethyl)phenyl]-3-hexen-2-ylsuccinamic acid (0.089 g) as a beige solid, m/z (M+H)$^+$ 468/470, 93.3% purity.

The cyclisation reaction mixture was stirred for 48 hours at ambient temperature before work-up, without further heating, to give a sticky solid. The solid was dissolved in hot toluene (3 ml), the clear solution was decanted from insoluble residues, then it was diluted with hexane (20 ml). The resulting solid was collected by filtration and dried in vacuo to give 1-[2-chloro-5-(4-oxo-3,4-dihydrophalazin-1-ylmethyl)phenyl]-3-hexen-2-ylpyrrolidine-2,5-dione (0.034 g) as a beige solid, m/z (M+H)$^+$ 450/452, 96.2% purity.

Example 42

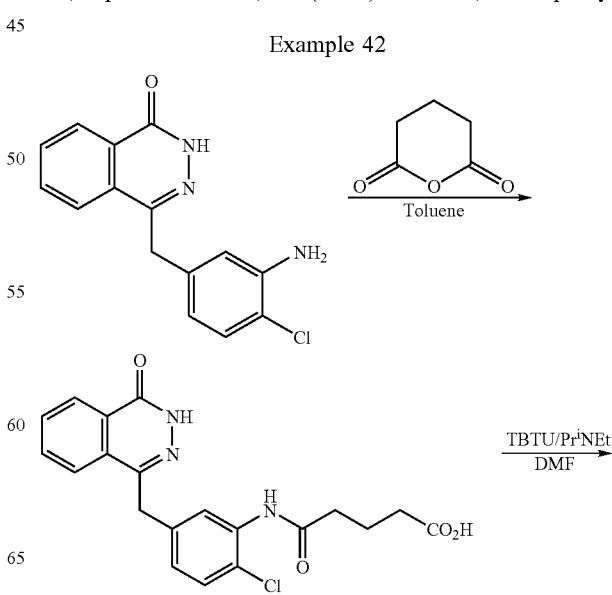

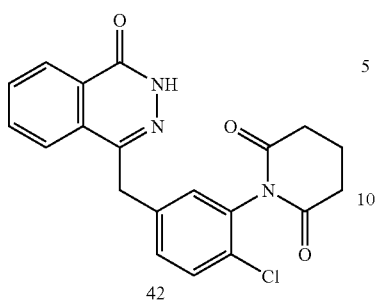

The open chain intermediate was 4-[2-chloro-5-(4-oxo-3,4-dihydrophthalazin-1-ylmethyl)phenylcarbamoyl]butyric acid (0.115 g), obtained as a white powder, m.pt. 238–241° C.; 250 MHz $^1$H-nmr (d$_6$-DMSO) δ (ppm): 1.7–1.9 (m, 2H) (—CH$_2$CH$_2$CH$_2$—), 2.25–2.5 (m, 4H) (—CH$_2$CH$_2$CH$_2$—), 4.4 (s, 1H) (ArCH$_2$—), 7.15–7.2 (m, 1H) (ArH), 7.4–7.50 (m, 1H) (ArH), 7.65–7.7 (s, 1H) (ArH), 7.8–8.05 (m, 3H) (3×ArH), 8.3 (d, 1H) (ArH), 9.5 (s, 1H) (chain CONH), 12.2 (s, 1H) (—CO$_2$H), 12.7 (s, 1H) (ring CONH); m/z (M+H)$^+$ 400/402, 100% purity.

The cyclisation reaction mixture was stirred for 3 hours at ambient temperature before work-up, without further heating, to give 1-[2-chloro-5-(4-oxo-3,4-dihydrophalazin-1-ylmethyl)phenyl]piperidine-2,5-dione (0.017 g) as an off-white powder, m/z (M+H)$^+$ 382/384, 98.0% purity.

Example 43

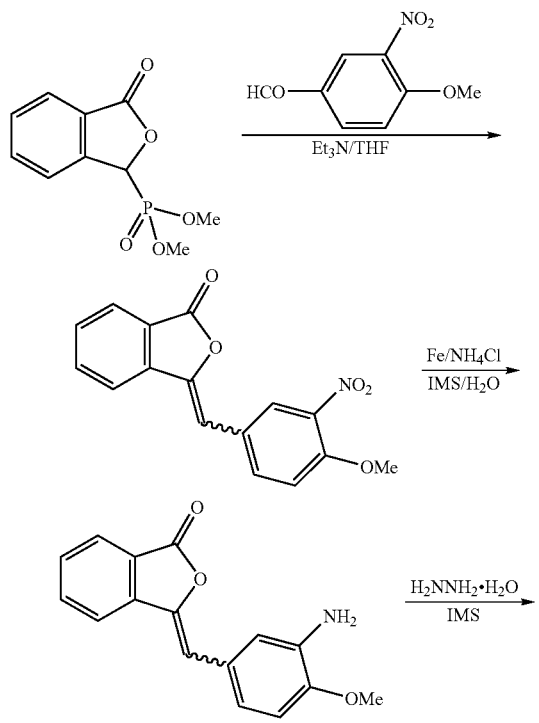

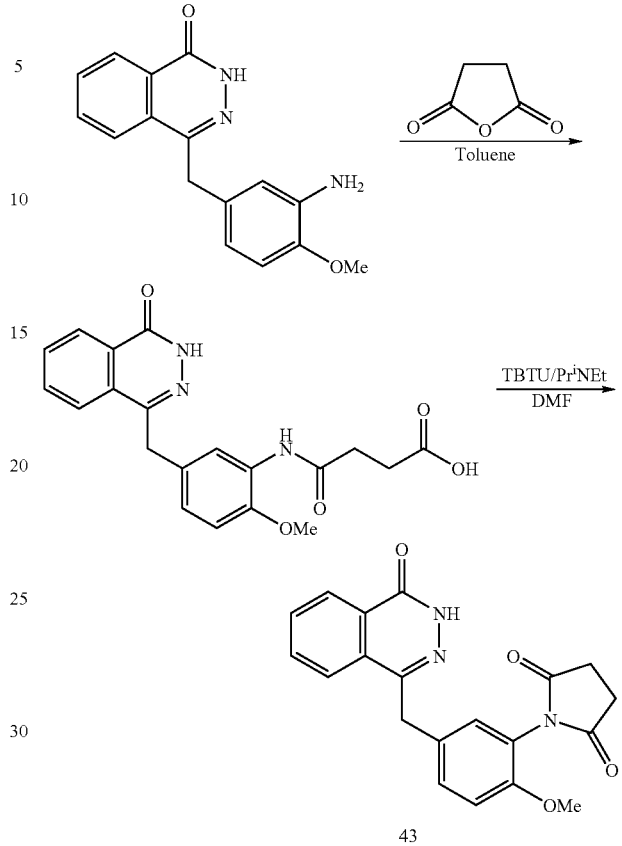

A stirred solution of dimethyl 3-oxo-1,3,-dihydroisobenzofuran-1-ylphosphonate (2.42 g, 0.01 mol; prepared in a manner similar to that described in Example 23) and 4-methoxy-3-nitrobenzaldehyde (1.81 g, 0.01 mol) in tetrahydrofuran (15 ml) was cooled to 15° C. and a solution of triethylamine (1.01 g, 0.01 mol) in tetrahydrofuran (1.5 ml) was added dropwise at <25° C. The mixture was stirred at ambient temperature for 4 hours, allowed to stand at this temperature for a further 16 hours and the resulting mixture was concentrated in vacuo. The residue was triturated with water (50 ml) and stirred at ambient temperature for 2 hours before the resulting solid was collected by filtration and dried in vacuo for 24 hours to give crude 3-(4-methoxy-3-nitrobenzylidene)-3H-isobenzofuran-1-one (2.53 g) as a yellow solid, m.pt. 173–181° C., which was used directly in the next stage.

A stirred mixture of the above crude 3-(4-methoxy-3-nitrobenzylidene)-3H-isobenzofuran-1-one (2.5 g, 0.0085 mol), industrial methylated spirit (40 ml), water (30 ml) and ammonium chloride (0.91 g, 0.017 mol) was heated to 70° C., and iron powder (4.76 g, 0.085 gatom) was added in portions. When the addition was complete, the stirred mixture was heated under reflux for a further 2 hours, then it was filtered while hot through Celite. The collected inorganic solids were washed with hot industrial methylated spirit (3×80 ml), then the filtrate and washings were combined and the solvent was removed in vacuo. The residue was triturated with water (50 ml) and the resulting solid was collected by filtration and dissolved in ethyl acetate (300 ml). The solution was filtered, the filtrate was concentrated in vacuo and the residue was triturated with industrial methylated spirit (10 ml). The resulting solid was collected by filtration and dried in vacuo for 24 hours to give 3-(3-amino-4-methoxybenzylidene)-3H-isobenzofuran-1-one (1.49 g) as a yellow solid, m.pt. 148–153° C.; m/z (M+H)$^{+\cdot}$ 268, 100% purity.

A stirred mixture of the above 3-(3-amino-4-methoxybenzylidene)-3H-isobenzofuran-1-one (1.336 g, 0.005 mol), industrial methylated spirit (20 ml) and hydrazine monohydrate (0.25 g, 0.005 mol) was heated under reflux for 1.5 hours then cooled to ambient temperature. The resulting solid was collected by filtration, washed with water (5 ml), and dried in vacuo to give 4-(3-amino-4-methoxybenzyl)-2H-phthalazin-1-one (1.15 g) as a beige solid, m.pt. 211.5–214.5° C.; 250 MHz $^1$H-nmr (d$_6$-DMSO) δ (ppm): 3.75 (s, 3H) (—OCH$_3$), 4.15 (s, 2H) (ArCH$_2$—), 4.75 (s, 2H) (—NH$_2$) 6.5–6.6 (m, 2H) (2×ArH), 6.7–6.75 (m, 1H) (ArH) 7.8–8.0 (m, 3H)(3×ArH), 8.3 (d, 1H) (ArH), 12.65 (s, 1H) (CONH); m/z (M+H)$^{+\cdot}$ 282, 100% purity.

A stirred mixture of 4-(3-amino-4-methoxybenzyl)-2H-phthalazin-1-one (0.281 g, 1 mmol), succinic anhydride (0.1 g, 1 mmol) and toluene (20 ml) was heated under reflux for 10 hours, then cooled to ambient temperature. The solvent was removed in vacuo, the residue was diluted with water (30 ml), and the mixture was heated under reflux for 30 minutes. The resulting solid was collected by filtration from the hot mixture and crystallised from glacial acetic acid (20 ml) to give N-[2-methoxy-5-(4-oxo-3,4-dihydrophalazin-1-ylmethyl)phenyl]succinamic acid (0.244 g) as an off-white solid, m.pt. 247–251° C.; 250 MHz $^1$H-nmr (d$_6$-DMSO) δ (ppm): 2.45–2.55 (m, 2H) (—CH$_2$CH$_2$—) 2.6–2.7 (m, 2H) (—CH$_2$CH$_2$—), 3.8 (s, 3H) (—OCH$_3$), 4.25 (s, 2H) (ArCH$_2$—), 6.9–7.1 (m, 2H) (2×ArH), 7.8–8.05 (m, 4H) (4×ArH), 8.3 (d, 1H) (ArH), 9.1 (s, 1H) (chain CONH), 12.15 (br.s, 1H) (—COOH), 12.65 (s, 1H) (ring CONH): m/z (M+H)$^{+\cdot}$ 382, 100% purity.

O-Benzotriazol-1-yl-N,N,N'N'-tetramethyluronium tetrafluoroborate (0.217 g, 0.68 mmol) and diisopropylethylamine (0.148 g, 1.14 mmol) were added sequentially at ambient temperature to a stirred solution of N-[2-methoxy-5-(4-oxo-3,4-dihydrophalazin-1-ylmethyl)phenyl]succinamic acid (0.2 g, 0.52 mmol) in dimethylacetamide (1 ml), the mixture was stirred at ambient temperature for 3 hours, then it was allowed to stand at ambient temperature for 16 hours. The mixture was added dropwise to water (10 ml) and stirred at ambient temperature for 1 hour. The resulting solid was collected by filtration, washed with water (2×1 ml) and dried in vacuo to give 1-[2-methoxy-5-(4-oxo-3,4-dihydrophalazin-1-ylmethyl)phenyl]pyrrolidine-2,5-dione (0.15 g) as an off-white solid, m.pt. 224–228° C.; 250 MHz $^1$H-nmr (d$_6$-DMSO) δ (ppm): 2.7–2.9 (m, 4H) (—CH$_2$CH$_2$—), 3.7 (s, 3H) (—OCH$_3$), 4.3 (s, 2H) (ArCH$_2$—), 7.05–7.2 (m, 2H) (2×ArH), 7.4–7.5 (d, 1H)(ArH), 7.8–8.05 (m, 3H) (3×ArH), 8.3 (d, 1H) (ArH), 12.65 (s, 1H) (CONH); m/z (M+H)$^{+\cdot}$ 364, 100% purity.

Biological Testing

In order to assess the inhibitory action of the compounds, the following assay was used to determine IC$_{50}$ values.

Mammalian PARP, isolated from Hela cell nuclear extract, was incubated with Z-buffer (25 mM Hepes (Sigma); 12.5 mM MgCl$_2$ (Sigma); 50 mM KCl (Sigma); 1 mM DTT (Sigma); 10% Glycerol (Sigma) 0.001% NP-40 (Sigma); pH 7.4) in 96 well FlashPlates (TRADE MARK) (NEN, UK) and varying concentrations of said inhibitors added. All compounds were diluted in DMSO and gave final assay concentrations of between 10 and 0.01 μM, with the DMSO being at a final concentration of 1% per well. The total assay volume per well was 40 μl.

After 10 minutes incubation at 30° C. the reactions were initiated by the addition of a 10 μl reaction mixture, containing NAD (5 μM), $^3$H-NAD and 30 mer double stranded DNA-oligos. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 μl 30% acetic acid to each well. The plates were then shaken for 1 hour at room temperature.

The plates were transferred to a TopCount NXT (TRADE MARK) (Packard, UK) for scintillation counting. Values recorded are counts per minute (cpm) following a 30 second counting of each well.

The % enzyme activity for each compound is then calculated using the following equation:

$$\% \text{ Inhibition} = 100 - \left(100 \times \frac{(cpm \text{ of unknowns} - \text{mean negative } cpm)}{(\text{mean positive } cpm - \text{mean neagative } cpm)}\right)$$

IC$_{50}$ values (the concentration at which 50% of the enzyme activity is inhibited) were calculated, which are determined over a range of different concentrations, normally from 10 μM down to 0.01 μM. Such IC$_{50}$ values are used as comparative values to identify increased compound potencies.

For comparison, the IC$_{50}$ of 100 (1(2H)-phthalazinone) was determined using the above test to be 7.2 μM.

All the compounds of the examples have an IC$_{50}$ of less than 0.30 μM, and the following compounds have an IC$_{50}$ of less than 0.03 μM: 2, 3, 5, 7, 11–13, 15, 18–20, 23–39 and 41–43.

The Potentiation Factor (PF$_{50}$) for compounds is calculated as a ratio of the IC$_{50}$ of control cell growth divided by the IC$_{50}$ of cell growth+PARP inhibitor. Growth inhibition curves for both control and compound treated cells are in the presence of the alkylating agent methyl methanesulfonate (MMS). The test compounds were used at a fixed concentration of 200 nM. The concentrations of MMS were over a range from 0 to 10 μg/ml.

Cell growth was assessed using the sulforhodamine B (SRB) assay (Skehan, P., et al., (1990) New calorimetric cytotoxicity assay for anticancer-drug screening. J. Natl. Cancer Inst. 82, 1107–1112.). 2,000 HeLa cells were seeded into each well of a flat-bottomed 96-well microtiter plate in a volume of 100 μl and incubated for 6 hours at 37° C. Cells were either replaced with media alone or with media containing PARP inhibitor at a final concentration of 200 nM. Cells were allowed to grow for a further 1 hour before the addition of MMS at a range of concentrations (typically 0, 1, 2, 3, 5, 7 and 10 μg/ml) to either untreated cells or PARP inhibitor treated cells. Cells treated with PARP inhibitor alone were used to assess the growth inhibition by the PARP inhibitor.

Cells were left for a further 16 hours before replacing the media and allowing the cells to grow for a further 72 hours at 37° C. The medium was then removed and the cells fixed with 100μl of ice cold 10% (w/v) trichloroacetic acid. The plates were incubated at 4° C. for 20 minutes and then washed four times with water. Each well of cells was then stained with 100 μl of 0.4% (w/v) SRB in 1% acetic acid for 20 minutes before washing four times with 1% acetic acid.

Plates were then dried for 2 hours at room temperature. The dye from the stained cells was solubilized by the addition of 100 μl of 10 mM Tris Base into each well. Plates were gently shaken and left at room temperature for 30 minutes before measuring the optical density at 564 nM on a Microquant microtiter plate reader.

The $PF_{50}$s of the following compounds were determined, and found to be greater than, or equal to 1, when tested at 200 nM: 2, 5, 11, 13 and 15–43.

Assessment of compound stability was made both in vitro microsomal and heptatocyte preparations) and in vivo animal models. Selected compounds were tested and were shown to exhibit beneficial pharmacokinetic profiles.

What is claimed is:

1. A compound of formula

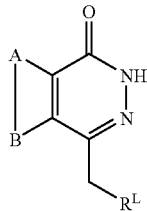

or an optical isomer, enantiomer, diastereomer, stereoisomer, tautomer, salt, chemically protected form, or prodrug ester thereof wherein:

A and B together represent an optionally substituted, fused aromatic ring, wherein the optional substituents are selected from the group consisting of halo, nitro, hydroxy, ether, thiol, thioether, amino, $C_{1-10}$ alkyl, $C_{3-20}$ heterocyclyl, and $C_{5-20}$ aryl, and wherein one or more substituents may together form a ring of formula $-(CH_2)_q-$ or $-O-(CH_2)_r-O-$, wherein q is 2 to 5 and r is 1 to 3;

$R^L$ is a $C_{5-7}$ aryl group substituted in the meta position by the group $R^2$, and optionally further substituted, wherein the optional substituents are selected from the group consisting of halo, nitro, hydroxy, ether, thiol, thioether, amino, $C_{1-10}$ alkyl, $C_{3-20}$ heterocyclyl, and $C_{5-20}$ aryl, and wherein one or more substiutents may together form a ring of formula $-(CH_2)_q-$ or $-O-(CH_2)_r-O-$, wherein q is 2 to 5 and r is 1 to 3; wherein $R^2$ is selected from:

a)

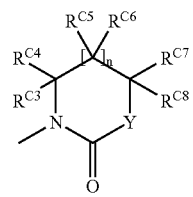

wherein:
n is 0 or 1;
Y is selected from $NR^{N1}$ and $CR^{C1}R^{C2}$;
$R^{N1}$ is selected from H, optionally substituted $C_{1-10}$ alkyl, optionally substituted $C_{5-6}$ aryl and optionally substituted $C_{1-10}$ alkylacyl, wherein the optional substituents are independently selected from halo, hydroxy, $-OR^5$, nitro, cyano, $-C(=O)R^5$, $-COOH$, $-C(=O)OR^5$, $-C(=O)NR^6R^7$, $-NR^5R^7$, $-NR^6C(=O)R^7$, $-OC(=O)R^5$, $-SH$, $-SR^6$, $-S(=O)R^5$, $-S(=O)_2R^5$, wherein $R^5$ is selected from the group consisting of $C_{1-7}$ alkyl, $C_{3-20}$ heterocyclyl, and $C_{5-20}$ aryl, and wherein $R^6$ and $R^7$ are independently selected from hydrogen, $C_{1-7}$ alkyl, $C_{3-20}$ heterocyclyl, and $C_{5-20}$ aryl group;

$R^{C1}$, $R^{C2}$, $R^{C3}$, $R^{C4}$, $R^{C5}$, $R^{C6}$, $R^{C7}$ and $R^{C8}$ are independently selected from H, R, SR and $NHC(=O)OR$, where R is optionally substituted $C_{1-10}$ alkyl or optionally substituted $C_{5-6}$ aryl, wherein the optional substituents are as described above in the definition of $R^{N1}$;

$R^{C4}$ and $R^{C6}$, $R^{C6}$ and $R^{C8}$ or $R^{C8}$ and $R^{C2}$ may optionally together form a double bond; $R^{C1}$ and $R^{C2}$, $R^{C5}$ and $R^{C6}$ or $R^{C7}$ and $R^{C8}$ together with the carbon atom to which they are attached may optionally form a spiro-fused $C_{5-7}$ carbocyclic or heterocyclic ring; and $R^{C5}$ and $R^{C7}$ or $R^{C7}$ and $R^{C1}$ together with the carbon atoms to which they are attached form an optionally substituted ring system, wherein the optional substituents are selected from the group consisting of halo, nitro, hydroxy, ether, thiol, thioether, amino, $C_{1-10}$ alkyl, $C_{3-20}$ heterocyclyl, and $C_{5-20}$ aryl;

b)

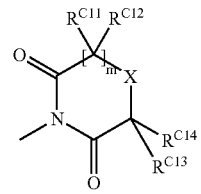

wherein
m is 0 or 1;
X is selected from $NR^{N2}$ and $CR^{C9}R^{C10}$;
$R^{N2}$ is selected from H, optionally substituted $C_{1-10}$ alkyl, optionally substituted $C_{5-6}$ aryl and optionally substituted $C_{1-10}$ alkylacyl, wherein the optional substituents are independently selected from halo, hydroxy, $-OR^5$, nitro, cyano, $-C(=O)R^5$, $-COOH$, $-C(=O)OR^5$, $-C(=O)NR^6R^7$, $-NR^5R^7$, $-NR^6C(=O)R^7$, $-OC(=O)R^5$, $-SH$, $-SR^5$, $-S(=O)R^5$, $-S(=O)_2R^5$, wherein $R^5$ is selected from the group consisting of $C_{1-7}$ alkyl, $C_{3-20}$ heterocyclyl, and $C_{5-20}$ aryl, and wherein $R^6$ and $R^7$ are independently selected from hydrogen, $C_{1-7}$ alkyl, $C_{3-20}$ heterocyclyl, and $C_{5-20}$ aryl group;

$R^{C9}$, $R^{C10}$, $R^{C11}$, $R^{C12}$, $R^{C13}$ and $R^{C14}$ are independently selected from H, R, SR and $NHC(=O)OR$, where R is as defined above;

$R^{C12}$ and $R^{C10}$ or $R^{C10}$ and $R^{C14}$ may optionally together form a double bond;

$R^{C11}$ and $R^{C12}$, $R^{C9}$ and $R^{C10}$ or $R^{C13}$ and $R^{C14}$ together with the carbon atom to which they are attached may optionally form a spiro-fused $C_{5-7}$ carbocyclic or heterocyclic ring; and $R^{C11}$ and $R^{C9}$ or $R^{C9}$ and $R^{C13}$ together with the carbon atom to which they are attached may form an optionally substituted ring system, wherein the optional substituents are selected from the group consisting of halo, nitro, hydroxy, ether, thiol, thioether, amino, $C_{1-10}$ alkyl, $C_{3-20}$ heterocyclyl, and $C_{5-20}$ aryl.

2. A compound according to claim 1, wherein the fused aromatic ring represented by A-B is benzene.

3. A compound according to either claim 1, wherein $R^L$ is a phenyl group.

4. A compound according to claim 3, wherein the phenyl group has one further substituent in addition to $R^2$, wherein the further substituent is selected from the group consisting of halo, nitro, hydroxy, ether, thiol, thioether, amino, $C_{1-10}$ alkyl, $C_{3-20}$ heterocyclyl, and $C_{5-20}$ aryl, and wherein one or more substituents may together form a ring of formula —$(CH_2)_q$— or —O—$(CH_2)_r$—O—, wherein q is 2 to 5 and r is 1 to 3.

5. A compound according to claim 4, wherein the further substituent is selected from halo and $C_{1-4}$ alkoxy.

6. A compound according to claim 5, wherein the further substituent is in the para position.

7. A compound according to claim 1, wherein $R^2$ is a).

8. A compound according to claim 7, wherein n is 0.

9. A compound according to either claim 7, wherein Y is $CR^{C1}R^{C2}$.

10. A compound according to claim 8, wherein $R^{C1}$ and $R^{C2}$ are independently selected from H and R.

11. A compound according to claim 10, wherein $R^{C1}$ and $R^{C2}$ are both H.

12. A compound according to claim 7, wherein none of $R^{C2}$, $R^{C4}$, $R^{C6}$ and $R^{C8}$ form a double bond, there are no spiro-fused rings, and $R^{C5}$ and $R^{C7}$ and $R^{C7}$ and $R^{C1}$ do not form an optionally substituted ring system.

13. A compound according to claim 7, wherein $R^{C3}$, $R^{C4}$, $R^{C5}$, $R^{C6}$, $R^{C7}$ and $R^{C8}$ are independently selected from H and R.

14. A compound according to claim 13, wherein $R^{C3}$, $R^{C4}$, $R^{C5}$, $R^{C6}$, $R^{C7}$ and $R^{C8}$ are all H.

15. A compound according to claim 1, wherein $R^2$ is b).

16. A compound according to claim 15, wherein m is 0.

17. A compound according to claim 15, wherein $R^{N2}$ is selected from H and optionally substituted $C_{1-10}$ alkyl.

18. A compound according to claim 15, wherein X is $CR^{C9}R^{C10}$.

19. A compound according to claim 18, wherein $R^{C9}$ and $R^{C10}$ are independently selected from H and R.

20. A compound according to claim 19, wherein $R^{C9}$ and $R^{C10}$ are both H.

21. A compound according to claim 15, wherein none of $R^{C10}$, $R^{C12}$ and $R^{C14}$ form a double bond, there are no spiro-fused rings, and $R^{C11}$ and $R^{C9}$ and $R^{C9}$ and $R^{C13}$ do not form an optionally substituted ring system.

22. A compound according to claim 15, wherein $R^{C11}$, $R^{C12}$, $R^{C13}$ and $R^{C14}$ are independently selected from H and R.

23. A compound according to claim 22, wherein $R^{C11}$, $R^{C12}$, $R^{C13}$ and $R^{C14}$ are independently selected from H, optionally substituted $C_{1-4}$ alkyl and phenyl.

24. A compound according to claim 15, wherein at least two of $R^{C11}$, $R^{C12}$, $R^{C13}$ and $R^{C14}$ are H.

25. A pharmaceutical composition comprising a compound according to claim 1 and a pharmaceutically acceptable carrier or diluent.

26. A compound according to claim 17, wherein $R^{N2}$ is selected from H and optionally substituted $C_{1-4}$ alkyl.

27. A compound according to claim 17, wherein $R^{N2}$ is selected from H and unsubstituted $C_{1-4}$ alkyl.

28. A method of inhibiting PARP in a cell comprising contacting the cell with an effective amount of a compound according to claim 1, wherein inhibition of PARP treats a disease selected from the group consisting of: haemorraghic shock; ischaemic injury; reperfusion injury, both cerebral and cardiovascular; and the acute treatment of cytotoxicity following cardiovascular surgery.

29. A method of treating cervical cancer of the human or animal body comprising administering an effective amount of a compound according to claim 1 in combination with ionizing radiation or a chemotherapeutic agent.

* * * * *